(12) United States Patent
Ito et al.

(10) Patent No.: US 9,555,001 B2
(45) Date of Patent: Jan. 31, 2017

(54) PHARMACEUTICAL COMPOSITION AND USES THEREOF

(71) Applicants: Masanori Ito, Hyogo (JP); Kenji Egusa, Biberach an der Riss (DE); Kyle Kleinbeck, Brooklyn, NY (US); Roman Messerschmid, Ulm (DE); Peter Schneider, Ulm-Einsingen (DE); Venkata Voleti, Mason, OH (US)

(72) Inventors: Masanori Ito, Hyogo (JP); Kenji Egusa, Biberach an der Riss (DE); Kyle Kleinbeck, Brooklyn, NY (US); Roman Messerschmid, Ulm (DE); Peter Schneider, Ulm-Einsingen (DE); Venkata Voleti, Mason, OH (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1 day.

(21) Appl. No.: 13/785,365

(22) Filed: Mar. 5, 2013

(65) Prior Publication Data

US 2013/0236543 A1 Sep. 12, 2013

Related U.S. Application Data

(60) Provisional application No. 61/607,771, filed on Mar. 7, 2012.

(51) Int. Cl.
| | |
|---|---|
| A61K 9/20 | (2006.01) |
| A61K 31/522 | (2006.01) |
| A61K 31/155 | (2006.01) |
| A61K 31/7048 | (2006.01) |
| A61K 9/24 | (2006.01) |
| A61K 9/00 | (2006.01) |
| A61K 45/06 | (2006.01) |
| A61K 9/28 | (2006.01) |

(52) U.S. Cl.
CPC .......... *A61K 9/2081* (2013.01); *A61K 9/0065* (2013.01); *A61K 9/209* (2013.01); *A61K 31/155* (2013.01); *A61K 31/522* (2013.01); *A61K 31/7048* (2013.01); *A61K 45/06* (2013.01); *A61K 9/2031* (2013.01); *A61K 9/2866* (2013.01)

(58) Field of Classification Search
None
See application file for complete search history.

(56) References Cited

U.S. PATENT DOCUMENTS

| | | |
|---|---|---|
| 2,056,046 A | 9/1936 | Fourneau |
| 2,375,138 A | 5/1945 | Victors |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,884,906 A | 5/1975 | Van Der Meer et al. |
| 3,925,357 A | 12/1975 | Okada et al. |
| 4,005,208 A | 1/1977 | Bender et al. |
| 4,061,753 A | 12/1977 | Bodor et al. |
| 4,379,785 A | 4/1983 | Weyer et al. |
| 4,382,091 A | 5/1983 | Benjamin et al. |
| 4,599,338 A | 7/1986 | Regnier et al. |
| 4,602,023 A | 7/1986 | Kiely et al. |
| 4,639,436 A | 1/1987 | Junge et al. |
| 4,687,777 A | 8/1987 | Meguro et al. |
| 4,743,450 A | 5/1988 | Harris et al. |
| 4,786,023 A | 11/1988 | Harris et al. |
| 4,786,755 A | 11/1988 | Kiely et al. |
| 4,816,455 A | 3/1989 | Schickaneder et al. |
| 4,873,330 A | 10/1989 | Lindholm |
| 4,968,672 A | 11/1990 | Jacobson et al. |
| 5,041,448 A | 8/1991 | Janssens et al. |
| 5,051,509 A | 9/1991 | Nagano et al. |
| 5,051,517 A | 9/1991 | Findeisen et al. |
| 5,084,460 A | 1/1992 | Munson, Jr. et al. |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |

(Continued)

FOREIGN PATENT DOCUMENTS

| | | |
|---|---|---|
| AU | 2003280680 A1 | 6/2004 |
| AU | 2009224546 A1 | 9/2009 |

(Continued)

OTHER PUBLICATIONS

Abstract in English for KR20070111099, Nov. 11, 2007.
Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.
Ahren B: "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.
Augeri, David J. "Discovery and Preclinical Profile of Saxagliptin (BMS-477118): A Highly Potent, Long-Acting, Orally Active Dipeptidyl Peptidase IV Inhibitor for the Treatment of Type 2 Diabetes" J. Med. Chem. (2005) vol. 48, pp. 5025-5037.

(Continued)

*Primary Examiner* — Frederick Krass
*Assistant Examiner* — Celeste A Roney
(74) *Attorney, Agent, or Firm* — Michael P. Morris; David L. Kershner

(57) ABSTRACT

The present invention relates to pharmaceutical compositions comprising fixed dose combinations of a DPP-4 inhibitor drug and/or a SGLT-2 inhibitor drug, and metformin XR, processes for the preparation thereof, and their use to treat certain diseases.

17 Claims, No Drawings

(56) References Cited

U.S. PATENT DOCUMENTS

| | | |
|---|---|---|
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,200,958 B1 | 3/2001 | Odaka et al. |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,414,126 B1 | 7/2002 | Ellsworth et al. |
| 6,448,323 B1 * | 9/2002 | Jordan et al. ............... 524/451 |
| 6,515,117 B2 | 2/2003 | Ellsworth et al. |
| 6,548,481 B1 | 4/2003 | Demuth et al. |
| 6,579,868 B1 | 6/2003 | Asano et al. |
| 6,613,806 B1 | 9/2003 | Aven et al. |
| 6,627,611 B2 | 9/2003 | Tomiyama et al. |
| 6,727,261 B2 | 4/2004 | Gobbi et al. |
| 6,774,112 B2 | 8/2004 | Gougoutas |
| 6,784,195 B2 | 8/2004 | Hale et al. |
| 6,794,480 B2 | 9/2004 | Goto et al. |
| 6,821,978 B2 | 11/2004 | Chackalamannil et al. |
| 6,869,947 B2 | 3/2005 | Kanstrup et al. |
| 6,890,898 B2 | 5/2005 | Bachovchin et al. |
| 6,936,590 B2 | 8/2005 | Washburn et al. |
| 6,972,283 B2 | 12/2005 | Fujikura et al. |
| 6,995,183 B2 | 2/2006 | Hamann et al. |
| 7,034,039 B2 | 4/2006 | Oi et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,169,761 B2 | 1/2007 | Tomiyama et al. |
| 7,173,028 B2 | 2/2007 | Dahmann et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,202,350 B2 | 4/2007 | Imamura et al. |
| 7,217,711 B2 | 5/2007 | Eckhardt et al. |
| 7,235,538 B2 | 6/2007 | Kanstrup et al. |
| 7,247,478 B2 | 7/2007 | Eberhardt et al. |
| 7,291,642 B2 | 11/2007 | Kauffmann-Hefner et al. |
| 7,361,687 B2 | 4/2008 | Barth et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,393,847 B2 | 7/2008 | Eckhardt et al. |
| 7,407,955 B2 | 8/2008 | Himmelsbach et al. |
| 7,407,995 B2 | 8/2008 | Ok et al. |
| 7,417,032 B2 | 8/2008 | Eckhardt et al. |
| 7,419,959 B2 | 9/2008 | Eckhardt et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,541,341 B2 | 6/2009 | Fushimi et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,589,193 B2 | 9/2009 | Washburn et al. |
| 7,610,153 B2 | 10/2009 | Carter, Jr. et al. |
| 7,645,763 B2 | 1/2010 | Himmelsbach et al. |
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,718,666 B2 | 5/2010 | Boehringer et al. |
| 7,723,309 B2 | 5/2010 | Himmelsbach et al. |
| 7,745,414 B2 | 6/2010 | Eckhardt et al. |
| 7,754,481 B2 | 7/2010 | Eberhardt et al. |
| 7,772,191 B2 | 8/2010 | Eckhardt et al. |
| 7,772,192 B2 | 8/2010 | Esko |
| 7,772,378 B2 | 8/2010 | Himmelsbach et al. |
| 7,772,407 B2 | 8/2010 | Imamura et al. |
| 7,776,830 B2 | 8/2010 | Eckhardt et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,283,326 B2 | 10/2012 | Eckhardt et al. |
| 8,455,435 B2 | 6/2013 | Franz et al. |
| 8,507,450 B2 | 8/2013 | Eckhardt et al. |
| 8,551,957 B2 | 10/2013 | Dugi et al. |
| 8,557,782 B2 | 10/2013 | Eckhardt et al. |
| 8,673,927 B2 | 3/2014 | Dugi et al. |
| 8,679,520 B2 | 3/2014 | Horres et al. |
| 8,785,455 B2 | 7/2014 | Hotter et al. |
| 8,802,842 B2 | 8/2014 | Weber et al. |
| 8,865,729 B2 | 10/2014 | Sieger et al. |
| 8,962,636 B2 | 2/2015 | Pfrengle et al. |
| 9,034,883 B2 | 5/2015 | Klein et al. |
| 9,149,478 B2 | 10/2015 | Klein et al. |
| 9,186,392 B2 | 11/2015 | Klein et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0137903 A1 | 9/2002 | Ellsworth et al. |
| 2002/0160047 A1 | 10/2002 | Hussain et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0040490 A1 | 2/2003 | Sugiyama et al. |
| 2003/0064935 A1 | 4/2003 | Gougoutas |
| 2003/0078269 A1 | 4/2003 | Pearson et al. |
| 2003/0087843 A1 | 5/2003 | Washburn |
| 2003/0100563 A1 | 5/2003 | Edmondson et al. |
| 2003/0104053 A1 | 6/2003 | Gusler et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |

(56) References Cited

U.S. PATENT DOCUMENTS

| | | |
|---|---|---|
| 2003/0153509 A1 | 8/2003 | Bachovchin et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0023981 A1 | 2/2004 | Ren et al. |
| 2004/0034014 A1 | 2/2004 | Kanstrup et al. |
| 2004/0037883 A1* | 2/2004 | Zhou et al. .................. 424/471 |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2001/0138215 | 7/2004 | Eckhardt et al. |
| 2004/0126358 A1 | 7/2004 | Warne et al. |
| 2004/0138148 A1 | 7/2004 | Fushimi et al. |
| 2004/0138214 A1 | 7/2004 | Himmelsbach et al. |
| 2004/0138439 A1 | 7/2004 | Deshpande et al. |
| 2004/0152659 A1 | 8/2004 | Matsuoka et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259903 A1 | 12/2004 | Boehringer et al. |
| 2005/0020574 A1 | 1/2005 | Hauel et al. |
| 2005/0026921 A1 | 2/2005 | Eckhardt et al. |
| 2005/0032804 A1 | 2/2005 | Cypes et al. |
| 2005/0065098 A1 | 3/2005 | Fujikura et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0085680 A1 | 4/2005 | Auerbach et al. |
| 2005/0124555 A1 | 6/2005 | Tomiyama et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187168 A1 | 8/2005 | Eickelmann et al. |
| 2005/0187227 A1 | 8/2005 | Himmelsbach et al. |
| 2005/0203095 A1 | 9/2005 | Eckhardt et al. |
| 2005/0209166 A1 | 9/2005 | Eckhardt et al. |
| 2005/0233982 A1 | 10/2005 | Himmelsbach et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0034922 A1 | 2/2006 | Cheng et al. |
| 2006/0035841 A1 | 2/2006 | Eckhardt et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063722 A1 | 3/2006 | Washburn et al. |
| 2006/0063787 A1 | 3/2006 | Yoshikawa et al. |
| 2006/0074031 A1 | 4/2006 | Eckhardt et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142210 A1 | 6/2006 | Eckhardt et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0189548 A1 | 8/2006 | Himmelsbach et al. |
| 2006/0205711 A1 | 9/2006 | Himmelsbach et al. |
| 2006/0205943 A1 | 9/2006 | Dahanukar et al. |
| 2006/0210627 A1 | 9/2006 | Pfeffer et al. |
| 2006/0234953 A1 | 10/2006 | Himmelsbach et al. |
| 2006/0247226 A1 | 11/2006 | Himmelsbach et al. |
| 2006/0251728 A1 | 11/2006 | Himmelsbach et al. |
| 2006/0258749 A1 | 11/2006 | Eckhardt et al. |
| 2006/0270668 A1 | 11/2006 | Chew et al. |
| 2006/0270701 A1 | 11/2006 | Kroth et al. |
| 2007/0004648 A1 | 1/2007 | Himmelsbach et al. |
| 2007/0027092 A1 | 2/2007 | Himmelsbach et al. |
| 2007/0027168 A1 | 2/2007 | Pfrengle et al. |
| 2007/0049537 A1 | 3/2007 | Eckhardt et al. |
| 2007/0054867 A1 | 3/2007 | Eckhardt et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0072813 A1 | 3/2007 | Himmelsbach et al. |
| 2007/0073046 A1 | 3/2007 | Eckhardt et al. |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0173452 A1 | 7/2007 | DiMarchi et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0219178 A1 | 9/2007 | Muramoto |
| 2007/0249544 A1 | 10/2007 | Himmelsbach et al. |
| 2007/0254944 A1 | 11/2007 | Hughes |
| 2007/0259821 A1 | 11/2007 | Eckhardt et al. |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0281940 A1 | 12/2007 | Dugi et al. |
| 2007/0293690 A1 | 12/2007 | Tomiyama et al. |
| 2007/0299076 A1 | 12/2007 | Piotrowski et al. |
| 2008/0039427 A1 | 2/2008 | Ray et al. |
| 2008/0058379 A1 | 3/2008 | Eckhardt et al. |
| 2008/0107731 A1 | 5/2008 | Kohlrausch et al. |
| 2008/0108816 A1 | 5/2008 | Zutter |
| 2008/0193529 A1 | 8/2008 | Kowalski et al. |
| 2008/0207882 A1 | 8/2008 | Derdau et al. |
| 2008/0234367 A1 | 9/2008 | Washburn et al. |
| 2008/0249089 A1 | 10/2008 | Himmelsbach et al. |
| 2008/0255159 A1 | 10/2008 | Himmelsbach et al. |
| 2008/0287529 A1 | 11/2008 | Deshpande et al. |
| 2008/0312243 A1 | 12/2008 | Eckhardt et al. |
| 2008/0318922 A1 | 12/2008 | Nakahira et al. |
| 2009/0023913 A1 | 1/2009 | Eckhardt et al. |
| 2009/0023920 A1 | 1/2009 | Eckhardt |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0297470 A1 | 12/2009 | Franz |
| 2009/0301105 A1 | 12/2009 | Loerting |
| 2009/0318547 A1 | 12/2009 | Eckhardt et al. |
| 2009/0325926 A1 | 12/2009 | Himmelsbach |
| 2009/0326215 A1 | 12/2009 | Eckhardt et al. |
| 2010/0033177 A1 | 2/2010 | Ochi et al. |
| 2010/0069310 A1 | 3/2010 | Himmelsbach et al. |
| 2010/0074950 A1 | 3/2010 | Sesha |
| 2010/0081625 A1 | 4/2010 | Wienrich et al. |
| 2010/0092551 A1 | 4/2010 | Nakamura et al. |
| 2010/0093654 A1 | 4/2010 | Himmelsbach et al. |
| 2010/0099641 A1 | 4/2010 | Himmelsbach et al. |
| 2010/0173916 A1 | 7/2010 | Himmelsbach et al. |
| 2010/0179191 A1* | 7/2010 | Himmelsbach et al. ..... 514/326 |
| 2010/0183531 A1 | 7/2010 | Johncock et al. |

(56) References Cited

U.S. PATENT DOCUMENTS

| | | |
|---|---|---|
| 2010/0204250 A1 | 8/2010 | Himmelsbach et al. |
| 2010/0209506 A1 | 8/2010 | Eisenreich |
| 2010/0210662 A1 | 8/2010 | Baroni et al. |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0310664 A1 | 12/2010 | Watson et al. |
| 2010/0317575 A1 | 12/2010 | Pinnetti et al. |
| 2010/0317847 A1 | 12/2010 | Eckhardt et al. |
| 2010/0330177 A1* | 12/2010 | Pourkavoos .......... 424/465 |
| 2011/0009391 A1 | 1/2011 | Braun et al. |
| 2011/0014284 A1 | 1/2011 | Eisenreich et al. |
| 2011/0028391 A1 | 2/2011 | Holst et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0178033 A1 | 7/2011 | Eckhardt et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0236477 A1 | 9/2011 | Schneider et al. |
| 2011/0237526 A1 | 9/2011 | Weber et al. |
| 2011/0237532 A1 | 9/2011 | De Vries et al. |
| 2011/0237789 A1 | 9/2011 | Weber et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |
| 2012/0041069 A1 | 2/2012 | Sesha |
| 2012/0053173 A1 | 3/2012 | Banno et al. |
| 2012/0071403 A1 | 3/2012 | Strumph et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0196812 A1 | 8/2012 | Eickelmann et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0252782 A1 | 10/2012 | Himmelsbach et al. |
| 2012/0252783 A1 | 10/2012 | Himmelsbach et al. |
| 2012/0283169 A1 | 11/2012 | Grempler et al. |
| 2012/0296080 A1 | 11/2012 | Eckhardt et al. |
| 2012/0296091 A1 | 11/2012 | Sieger et al. |
| 2013/0035281 A1 | 2/2013 | Klein et al. |
| 2013/0035298 A1 | 2/2013 | Broedl et al. |
| 2013/0035821 A1 | 2/2013 | Bonne et al. |
| 2013/0064887 A1 | 3/2013 | Ito et al. |
| 2013/0096076 A1 | 4/2013 | Dugi et al. |
| 2013/0122089 A1 | 5/2013 | Kohlrausch et al. |
| 2013/0137646 A1 | 5/2013 | Wienrich et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |
| 2013/0252908 A1 | 9/2013 | Mayoux et al. |
| 2013/0317046 A1 | 11/2013 | Johansen |
| 2013/0324463 A1 | 12/2013 | Klein et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0087996 A1 | 3/2014 | Klein et al. |
| 2014/0088027 A1 | 3/2014 | Grempler et al. |
| 2014/0256624 A1 | 9/2014 | Grempler et al. |
| 2014/0274889 A1 | 9/2014 | Johansen et al. |
| 2014/0303097 A1 | 10/2014 | Broedl et al. |
| 2014/0303098 A1 | 10/2014 | Broedl et al. |
| 2014/0315832 A1 | 10/2014 | Broedl et al. |
| 2014/0371243 A1 | 12/2014 | Klein et al. |
| 2015/0196565 A1 | 7/2015 | Klein et al. |
| 2015/0246045 A1 | 9/2015 | Klein et al. |

FOREIGN PATENT DOCUMENTS

| | | |
|---|---|---|
| CA | 1123437 A1 | 5/1982 |
| CA | 2136288 A1 | 5/1995 |
| CA | 2382480 A1 | 3/2001 |
| CA | 2388818 A1 | 4/2001 |
| CA | 2418656 A1 | 2/2002 |
| CA | 2437240 A1 | 8/2002 |
| CA | 2435730 A1 | 9/2002 |
| CA | 2463989 A1 | 4/2003 |
| CA | 2494177 A1 | 2/2004 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2470365 A1 | 6/2004 |
| CA | 2508024 A1 | 6/2004 |
| CA | 2508226 A1 | 6/2004 |
| CA | 2508233 A1 | 6/2004 |
| CA | 2526145 A1 | 9/2004 |
| CA | 2529729 A1 | 12/2004 |
| CA | 2539032 A1 | 3/2005 |
| CA | 2543074 A1 | 6/2005 |
| CA | 2544480 A1 | 6/2005 |
| CA | 2548353 A1 | 7/2005 |
| CA | 2555050 A1 | 9/2005 |
| CA | 2556064 A1 | 9/2005 |
| CA | 2557269 A1 | 9/2005 |
| CA | 2557320 A1 | 9/2005 |
| CA | 2557801 A1 | 10/2005 |
| CA | 2558067 A1 | 10/2005 |
| CA | 2558446 A1 | 10/2005 |
| CA | 2561210 A1 | 10/2005 |
| CA | 2562859 A1 | 11/2005 |
| CA | 2569915 A1 | 1/2006 |
| CA | 2572149 A1 | 1/2006 |
| CA | 2572819 A1 | 1/2006 |
| CA | 2573777 A1 | 2/2006 |
| CA | 2574451 A1 | 2/2006 |
| CA | 2576294 A1 | 3/2006 |
| CA | 2574500 A1 | 4/2006 |
| CA | 2586938 A1 | 5/2006 |
| CA | 2590912 A1 | 6/2006 |
| CA | 2599419 A1 | 11/2006 |
| CA | 2617090 A1 | 2/2007 |
| CA | 2649922 A1 | 11/2007 |
| CA | 2651019 A1 | 11/2007 |
| CA | 2651089 A1 | 11/2007 |
| CA | 2696579 A1 | 2/2009 |
| CA | 2720450 A1 | 10/2009 |
| CA | 2726244 A1 | 12/2009 |
| CA | 2732803 A1 | 2/2010 |
| CA | 2735562 A1 | 2/2010 |
| CA | 2736421 A1 | 3/2010 |
| CA | 2738367 A1 | 4/2010 |
| CA | 2745037 A1 | 7/2010 |
| CA | 2745039 A1 | 7/2010 |
| CA | 2750798 A1 | 8/2010 |
| CA | 2752437 A1 | 8/2010 |
| CA | 2776296 A1 | 4/2011 |
| CA | 2782179 A1 | 6/2011 |
| CN | 101234105 A | 8/2008 |
| DE | 2205815 A1 | 8/1973 |
| DE | 2758025 A1 | 7/1979 |
| DE | 2951135 A1 | 6/1981 |
| DE | 19705233 A1 | 8/1998 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |

(56) References Cited

FOREIGN PATENT DOCUMENTS

| | | |
|---|---|---|
| DE | 102004044221 A1 | 3/2006 |
| DE | 102004054054 A1 | 5/2006 |
| EP | 0023032 A1 | 1/1981 |
| EP | 0149578 A2 | 7/1985 |
| EP | 0206567 A2 | 12/1986 |
| EP | 0223403 A2 | 5/1987 |
| EP | 0237608 A1 | 9/1987 |
| EP | 0248634 A2 | 12/1987 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0638567 A1 | 2/1995 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1224195 B | 7/2002 |
| EP | 1310245 A1 | 5/2003 |
| EP | 1333033 | 8/2003 |
| EP | 1338595 A2 | 8/2003 |
| EP | 1344780 A1 | 9/2003 |
| EP | 1354888 A1 | 10/2003 |
| EP | 1385856 A | 2/2004 |
| EP | 1406873 A2 | 4/2004 |
| EP | 1500403 A1 | 1/2005 |
| EP | 1514552 A1 | 3/2005 |
| EP | 1523994 A1 | 4/2005 |
| EP | 1535906 A1 | 6/2005 |
| EP | 1537880 A1 | 6/2005 |
| EP | 1553094 A1 | 7/2005 |
| EP | 1557165 A1 | 7/2005 |
| EP | 1564210 A1 | 8/2005 |
| EP | 1586571 A1 | 10/2005 |
| EP | 1609785 A1 | 12/2005 |
| EP | 1743655 A1 | 1/2007 |
| EP | 1760076 | 3/2007 |
| EP | 1791852 A2 | 6/2007 |
| EP | 1829877 A1 | 9/2007 |
| EP | 1852108 A1 | 11/2007 |
| EP | 1852439 A1 | 11/2007 |
| EP | 1897892 A2 | 3/2008 |
| EP | 2143443 A1 | 1/2010 |
| EP | 2166007 A1 | 3/2010 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 55007256 A | 1/1980 |
| JP | 56039056 A | 4/1981 |
| JP | 58164502 | 9/1983 |
| JP | 62030750 A | 2/1987 |
| JP | 770120 | 3/1995 |
| JP | 8333339 | 12/1996 |
| JP | 11124392 A | 5/1999 |
| JP | 11193270 | 7/1999 |
| JP | 2000502684 A | 3/2000 |
| JP | 2001213770 A | 8/2001 |
| JP | 2001278812 A | 10/2001 |
| JP | 2001288178 A | 10/2001 |
| JP | 2001292388 A | 10/2001 |
| JP | 2002348279 A | 12/2002 |
| JP | 2003511458 A | 3/2003 |
| JP | 2003286287 A | 10/2003 |
| JP | 2003300977 A | 10/2003 |
| JP | 2004161749 A | 6/2004 |
| JP | 2004196788 A | 7/2004 |
| JP | 2004250336 A | 9/2004 |
| JP | 2004359630 | 12/2004 |
| JP | 2005002092 A | 1/2005 |
| JP | 2005060625 A | 3/2005 |
| JP | 2006045156 A | 2/2006 |
| JP | 2010053576 A | 3/2010 |
| JP | 2010070576 A | 4/2010 |
| JP | 2010524580 A | 7/2010 |
| KR | 20070111099 A | 11/2007 |
| WO | 8706941 A1 | 11/1987 |
| WO | 9107945 A1 | 6/1991 |
| WO | 9205175 A1 | 4/1992 |
| WO | 9219227 A2 | 11/1992 |
| WO | 9402150 A1 | 2/1994 |
| WO | 9403456 A1 | 2/1994 |
| WO | 9532178 A1 | 11/1995 |
| WO | 9609045 A1 | 3/1996 |
| WO | 9611917 A1 | 4/1996 |
| WO | 9636638 A1 | 11/1996 |
| WO | 9718814 A1 | 5/1997 |
| WO | 9723447 A1 | 7/1997 |
| WO | 9723473 A1 | 7/1997 |
| WO | 9746526 A1 | 12/1997 |
| WO | 9807725 | 2/1998 |
| WO | 9811893 | 3/1998 |
| WO | 9818770 A1 | 5/1998 |
| WO | 9822464 A1 | 5/1998 |
| WO | 9828007 A1 | 7/1998 |
| WO | 9831697 A1 | 7/1998 |
| WO | 9840069 A2 | 9/1998 |
| WO | 9846082 A1 | 10/1998 |
| WO | 9856406 A1 | 12/1998 |
| WO | 9929695 A1 | 6/1999 |
| WO | 9938501 A2 | 8/1999 |
| WO | 9950248 A1 | 10/1999 |
| WO | 9956561 A1 | 11/1999 |
| WO | 9967279 A1 | 12/1999 |
| WO | 0069464 A1 | 11/2000 |
| WO | 0072799 A2 | 12/2000 |
| WO | 0073307 A2 | 12/2000 |
| WO | 0107441 A1 | 2/2001 |
| WO | 0116147 A1 | 3/2001 |
| WO | 0127128 A1 | 4/2001 |
| WO | 0132158 A2 | 5/2001 |
| WO | 0140180 A2 | 6/2001 |
| WO | 0147514 A1 | 7/2001 |
| WO | 0151919 | 7/2001 |
| WO | 0152825 | 7/2001 |
| WO | 0152825 A2 | 7/2001 |
| WO | 0152852 A1 | 7/2001 |
| WO | 0166548 A1 | 9/2001 |
| WO | 0168603 | 9/2001 |
| WO | 0168646 A1 | 9/2001 |
| WO | 0172290 A2 | 10/2001 |
| WO | 0174834 A1 | 10/2001 |
| WO | 0177110 A1 | 10/2001 |
| WO | 0196301 A1 | 12/2001 |
| WO | 0197808 A1 | 12/2001 |
| WO | 0202560 A2 | 1/2002 |
| WO | 0214271 A1 | 2/2002 |
| WO | 0224698 A1 | 3/2002 |
| WO | 02053516 A2 | 7/2002 |
| WO | 02053573 A1 | 7/2002 |
| WO | 02064606 A1 | 8/2002 |
| WO | 02068420 A1 | 9/2002 |
| WO | 02083066 A2 | 10/2002 |
| WO | 03000241 A2 | 1/2003 |
| WO | 03000250 | 1/2003 |
| WO | 03002531 A2 | 1/2003 |
| WO | 03002553 A1 | 1/2003 |
| WO | 03004496 A1 | 1/2003 |
| WO | 03020737 A1 | 3/2003 |
| WO | 03024965 A2 | 3/2003 |
| WO | 03031458 A1 | 4/2003 |
| WO | 03032997 A1 | 4/2003 |
| WO | 03033686 A2 | 4/2003 |
| WO | 03034944 A1 | 5/2003 |

(56) References Cited

FOREIGN PATENT DOCUMENTS

| | | |
|---|---|---|
| WO | 03037327 A1 | 5/2003 |
| WO | WO-03-035177 * | 5/2003 |
| WO | 03053929 A1 | 7/2003 |
| WO | 03055881 A1 | 7/2003 |
| WO | 03057200 A2 | 7/2003 |
| WO | 03059327 | 7/2003 |
| WO | 03064454 A1 | 8/2003 |
| WO | 03074500 A2 | 9/2003 |
| WO | 03078404 A1 | 9/2003 |
| WO | 03088900 A2 | 10/2003 |
| WO | 03094909 A2 | 11/2003 |
| WO | 03099279 A1 | 12/2003 |
| WO | 03099836 A1 | 12/2003 |
| WO | 03104229 A1 | 12/2003 |
| WO | 03106428 A1 | 12/2003 |
| WO | 2004002924 A1 | 1/2004 |
| WO | 2004007517 A1 | 1/2004 |
| WO | 2004011416 A1 | 2/2004 |
| WO | 2004013118 A1 | 2/2004 |
| WO | 2004016587 A1 | 2/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004037169 A2 | 5/2004 |
| WO | 2004041820 A1 | 5/2004 |
| WO | 2004043940 | 5/2004 |
| WO | 2004046115 A1 | 6/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004052902 A1 | 6/2004 |
| WO | 2004052903 A1 | 6/2004 |
| WO | 2004058233 A1 | 7/2004 |
| WO | 2004062689 A1 | 7/2004 |
| WO | 2004063209 A2 | 7/2004 |
| WO | 2004065380 A1 | 8/2004 |
| WO | 2004074246 A2 | 9/2004 |
| WO | 2004076470 A2 | 9/2004 |
| WO | 2004080990 A1 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007647 A1 | 1/2005 |
| WO | 2005007658 A2 | 1/2005 |
| WO | 2005012288 A1 | 2/2005 |
| WO | 2005012318 A2 | 2/2005 |
| WO | 2005012326 A1 | 2/2005 |
| WO | 2005021566 A2 | 3/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005063785 A2 | 7/2005 |
| WO | 2005082906 A1 | 9/2005 |
| WO | 2005085237 A1 | 9/2005 |
| WO | 2005085246 A1 | 9/2005 |
| WO | 2005085265 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A | 10/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2006002912 A1 | 1/2006 |
| WO | 2006005613 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006027204 A1 | 3/2006 |
| WO | 2006029577 A1 | 3/2006 |
| WO | 2006029769 A1 | 3/2006 |
| WO | 2006034489 A2 | 3/2006 |
| WO | 2006036664 A1 | 4/2006 |
| WO | 2006037537 A2 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006064033 A2 | 6/2006 |
| WO | 2006068163 A1 | 6/2006 |
| WO | 2006071078 A1 | 7/2006 |
| WO | 2006072334 A2 | 7/2006 |
| WO | 2006076231 A2 | 7/2006 |
| WO | 2006078593 A2 | 7/2006 |
| WO | 2006083491 A2 | 8/2006 |
| WO | 2006089872 A1 | 8/2006 |
| WO | 2006108842 A1 | 10/2006 |
| WO | 2006116157 | 11/2006 |
| WO | 2006117359 A1 | 11/2006 |
| WO | 2006117360 A1 | 11/2006 |
| WO | 2006120208 A1 | 11/2006 |
| WO | 2006135693 A2 | 12/2006 |
| WO | 2006137085 A1 | 12/2006 |
| WO | 2007000445 A1 | 1/2007 |
| WO | 2007007173 A2 | 1/2007 |
| WO | 2007014886 A1 | 2/2007 |
| WO | 2007014894 A2 | 2/2007 |
| WO | 2007014895 A2 | 2/2007 |
| WO | 2007017423 A1 | 2/2007 |
| WO | 2007025943 A2 | 3/2007 |
| WO | 2007028814 A1 | 3/2007 |
| WO | 2007031548 A2 | 3/2007 |
| WO | 2007033350 A1 | 3/2007 |
| WO | 2007035355 A2 | 3/2007 |
| WO | 2007035665 A1 | 3/2007 |
| WO | 2007039417 A1 | 4/2007 |
| WO | 2007041053 A2 | 4/2007 |
| WO | 2007050485 A2 | 5/2007 |
| WO | 2007071738 | 6/2007 |
| WO | 2007071738 A1 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128749 A1 | 11/2007 |
| WO | 2007128761 A2 | 11/2007 |
| WO | 2007135196 A2 | 11/2007 |
| WO | 2007137107 A2 | 11/2007 |
| WO | WO-2007-136151 * | 11/2007 |
| WO | 2007144175 A2 | 12/2007 |
| WO | 2007147185 A1 | 12/2007 |
| WO | 2007148185 A2 | 12/2007 |
| WO | 2007149797 A2 | 12/2007 |
| WO | 2008005569 A2 | 1/2008 |
| WO | 2008005576 A1 | 1/2008 |
| WO | 2008017670 | 2/2008 |
| WO | 2008017670 A1 | 2/2008 |
| WO | 2008020011 A1 | 2/2008 |
| WO | 2008022267 A2 | 2/2008 |
| WO | 2008034859 A1 | 3/2008 |
| WO | 2008049923 A1 | 5/2008 |
| WO | 2008055870 A1 | 5/2008 |

(56) References Cited

FOREIGN PATENT DOCUMENTS

| | | |
|---|---|---|
| WO | 2008055940 A2 | 5/2008 |
| WO | 2008062273 A2 | 5/2008 |
| WO | 2008070692 A2 | 6/2008 |
| WO | 2008081205 A1 | 7/2008 |
| WO | 2008083238 A2 | 7/2008 |
| WO | 2008087198 A1 | 7/2008 |
| WO | 2008089892 A1 | 7/2008 |
| WO | 2008090210 A1 | 7/2008 |
| WO | 2008093878 A1 | 8/2008 |
| WO | 2008093882 A1 | 8/2008 |
| WO | 2008101938 A1 | 8/2008 |
| WO | 2008101939 A1 | 8/2008 |
| WO | 2008101943 A1 | 8/2008 |
| WO | 2008113000 A1 | 9/2008 |
| WO | 2008116179 A1 | 9/2008 |
| WO | 2008130998 A2 | 10/2008 |
| WO | 2008131149 A2 | 10/2008 |
| WO | 2008137435 A1 | 11/2008 |
| WO | 2009011451 A | 1/2009 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009035969 A1 | 3/2009 |
| WO | 2009063072 A2 | 5/2009 |
| WO | 2009091082 A1 | 7/2009 |
| WO | 2009099734 A1 | 8/2009 |
| WO | WO-2009-121945 * | 8/2009 |
| WO | 2009111200 A1 | 9/2009 |
| WO | 2009112691 A2 | 9/2009 |
| WO | 2009121945 A2 | 10/2009 |
| WO | 2009123992 A1 | 10/2009 |
| WO | WO-2009-121945 * | 10/2009 |
| WO | WO-2009-111200 * | 11/2009 |
| WO | 2009147125 A1 | 12/2009 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010092163 A2 | 8/2010 |
| WO | 2010096384 A2 | 8/2010 |
| WO | 2010106457 A2 | 9/2010 |
| WO | 2010138535 A1 | 12/2010 |
| WO | 2010147768 A1 | 12/2010 |
| WO | WO-2010-140111 * | 12/2010 |
| WO | 2011011541 A1 | 1/2011 |
| WO | 2011039107 A1 | 4/2011 |
| WO | 2011039108 A2 | 4/2011 |
| WO | 2011039337 A1 | 4/2011 |
| WO | 2011039367 A2 | 4/2011 |
| WO | 2011060290 A2 | 5/2011 |
| WO | 2011064352 A1 | 6/2011 |
| WO | 2011113947 A1 | 9/2011 |
| WO | 2011117295 A1 | 9/2011 |
| WO | 2011120923 A1 | 10/2011 |
| WO | 2011138380 A1 | 11/2011 |
| WO | 2011138421 A1 | 11/2011 |
| WO | 2011161161 A1 | 12/2011 |
| WO | 2011163206 A2 | 12/2011 |
| WO | 2012031124 A2 | 3/2012 |
| WO | 2012062698 A1 | 5/2012 |
| WO | 2012065993 A1 | 5/2012 |
| WO | 2012088682 A1 | 7/2012 |
| WO | 2012089127 A1 | 7/2012 |
| WO | 2012106303 A1 | 8/2012 |
| WO | 2012107476 A1 | 8/2012 |
| WO | 2012120040 A1 | 9/2012 |
| WO | 2013098372 A1 | 7/2013 |
| WO | 2013103629 A1 | 7/2013 |
| WO | 2013131967 A1 | 9/2013 |
| WO | 2013139777 A1 | 9/2013 |
| WO | 2013171167 A1 | 11/2013 |
| WO | 2013174768 A1 | 11/2013 |
| WO | 2013179307 A2 | 12/2013 |

OTHER PUBLICATIONS

Aulinger, B.A. et al., "Ex-4 and the DPP-IV Inhibitor Vildagliptin have Additive Effects to Suppress Food Intake in Rodents". Abstract No. 1545-P, 2008.

Ault Addison, "Techniques and experiments for organic chemistry" University Science Books, 1998, pp. 59-60.

Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.

Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.

Byrn, Stephen et al. "Pharmaceutical Solids: A Strategic Approach to Regulatory Considerations" Pharmaceutical Research, vol. 12, No. 7, (1995) pp. 945-954.

CAS Registry No. 668270-12-0; STN database entered Mar. 28, 2004. 5 pgs.

Castaneda, Francisco et al. "Thioglycosides as inhibitors of hSGLT1 and hSGLT2: Potential therapeutic agents for the control of hyperglycemia in diabetes" International Journal of Medical Sciences (2007) 4(3), pp. 131-139.

Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCT00601250/2008_01_25 [retrieved on Feb. 27, 2009].

Clinical Trials. NCTO0622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.

Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.

Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.

Clinical Trials: NCT00602472. "BI 1356 in combination withe metformin and a sulphonylurea in Type 2 Diabetes". DrugLib.com, Nov. 3, 2008. http://www.druglib.com/trial/08 1NCT00309608.html.

Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.

Clinical Trials: NCT00798161. "Safety and efficacy of BI 1356 Plus Metformin in Type 2 Diabetes, Factorial Design". Clinical Trials. gov archive. A Service of the U.S> National Institutes of Health. Nov. 24, 2008, p. 1-3. http://clinicaltrials.gov/archive/NCT00798161/2008_11_24.

Conarello, S.L. et al., "Mice lacking dipeptidyl peptidase IV are protected against obesity and insulin resistance". PNAS, May 27, 2003, vol. 100, No. 11, p. 6825-6830.

Deacon, Carolyn F. "Perspectives in Diabetes Therapeutic Strategies Based on Glucagon-Like Peptide 1" Diabetes, (2004) vol. 53 pp. 2181-2189.

(56) References Cited

OTHER PUBLICATIONS

Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Drug Watch "Type 2 Diabetes Mellitus" Formulary vol. 43 Aug. 2008 p. 304.

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.

Eckhardt, M. et al., "8-(3-(R)-Aminopiperidin-1-yl)-7-but-2-ynyl-3-methyl-1-(4-methyl-quinazolin-2-ylmethyl)-3,7-dihydropurine-2,6-dione (BI1356), a Highly Potent, Selective, Long-Acting, and Orally Bioavailable DPP-4 Inhibitor for the Treatment of Type 2 Diabetes" J. Med Chem (2007) vol. 50, pp. 6450-6453.

FDA Formal Comments on "Draft Guidance for Industry on Powder Blends and Finished Dosage Units—Stratified In-Process Dosage Unit Sampling and Assessment" Jan. 21, 2004, 54 pgs.

Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No. 1, pp. 268-276.

Gallwitz, B. "Sitagliptin with Metformin: Profile of a Combination for the Treatment of Type 2 Diabetes". Drugs of Today, Oct. 2007, 43(10), p. 681-689.

Gallwitz, Baptist "Saxagliptin, a dipeptidyl peptidase IV inhibitor for the treatment of type 2 diabetes" IDrugs (2008) 11(12), pp. 906-917.

Ghassemi et al. "Synthesis and properties of new sulfonated poly(p-phenylene) derivatives for proton exchange membranes" Polymer (2004) pp. 5847-5854.

Graefe-Mody et al., "The novel DPP-4 inhibitor . . . " Diabetes, (online) 2008, XP002561421 http://professional.diabetes.org/content/posters/2008/p553-p.pdf.

Graefe-Mody, E.U., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.

Greco, Gary T. et al. "Segregation of Active Constituents from Tablet Formulations During Grinding: Theoretical Considerations" Drug Development and Industrial Pharmacy, (1982) 8(4), pp. 565-578.

Gwaltney, S. "Medicinal Chemistry Approaches to the Inhibition of Dipeptidyl Peptidase IV", Current Topics in Medicinal Chemistry, 2008, 8, p. 1545-1552.

Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.

He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.

Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.

Huttner, S. et al. "Safety, Tolerability, Pharmacokinetics, and Pharmacodynamics of Single Oral Doses of BI 1356, and Inhibitor of Dipeptidyl Peptidase 4, in Healthy Male Volunteers" Journal of Clinical Pharmacology (2008) V 48, pp. 1171-1178.

Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Iida, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.

International Search Report for PCT/EP2013/054524 mailed on May 6, 2013.

Isaji, Masayuki "Sodium-glucose cotransporter inhibitors for diabetes" Current Opinion in Investigational Drugs, (2007) vol. 8, No. 4, pp. 285-292.

Jagdmann Jr, G. Erik ; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.

Kadowaki, T et al. "PPAR gamma agonist and antagonist" Nihon Yakurigaku Zasshi (2001) vol. 118, No. 9, pp. 321-326. (English abstract).

Katsuno, Kenji et al. "Sergliflozin, a Novel Selective Inhibitor of Low-Affinity Sodium Glucose Cotransporter (SGLT2) Validates the Critical Role of SGLT2 in Renal Glucose Reabsorption and Modulates Plasma Glucose Level" The Journal of Pharmacology and Experimental Therapeutics (2007) vol. 320, No. 1, pp. 323-330.

Knochel, Paul et al. "Highly functionalized Organomagnesium Reagents Prepared through Halogen-Metal Exchange" Angew. Chem. INt. Ed. (2003) vol. 42, 4302-4320.

Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.

Krasovskiy Arkady et al. "A LiCL-Mediated Br/Mg Exchange Reaction for the Preparation of Functionalized Aryl- and Heterarylmagnesium Compounds from Organic Bromides**" Angew. Chem. Int. Ed. (2004) vol. 43, pp. 3333-3336.

Kuribayashi, Takeshi., et al; Bis C-Glycosylated Diphenylmethanes for Stable Glycoepitope Mimetics; Syntletters (1999) vol. 6 pp. 737-740.

Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.

Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.

Levien,T.L. et al, "New drugs in development for the treatment of diabetes", Diabetes Spectrum, American Diabetes Association, US, vol. 22, No. 2, Jan. 1, 2009, pp. 92-106.

Li, T, et al. "Lack of Pharmacokinetic Interaction between Dapagliflozin and Pioglitazone in Healthy Subjects" Journal of Clinical Pharmacology, (2009) vol. 49, No. 9, pp. 1093.

Lipworth, Brian J. "Clinical pharmacology of b3-adrenoceptors" Br J Clin Pharmacol (1996) pp. 291-300.

McHale, Mary "Grignard Reaction" Connexions module: m15245, (2007) pp. 1-18.

McLaughlin, Mark., et al; Suzuki-Miyaura Cross-Coupling of Benzylic Phospahates with Arylboronic Acids; Organic Letters (2005) vol. 7 No. 22 pp. 4875-4878.

McMaster University, Chem2006 Lab Manual, 1997/98, Expt 1, Part B, pp. 1-9.

Meece, J. "When Oral Agents Fail: Optimizing Insulin Therapy in the Older Adult". Consultant Pharmacist, The Society, Arlington, VA US. vol. 24, No. Suppl B, Jun. 1, 2009, p. 11-17.

(56) References Cited

OTHER PUBLICATIONS

Meng, Wei et al "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.
Merck Manual of Diagnosis and Therapy, 17th Edition, (1999) Ch 13 / Disorders of Carohydrate Metabolism, Diabetes Mellitus. pp. 165-177.
Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#v987998. last revision Jun. 2008 by Preeti Kishore M.D.
Merck: "Initial Therapy with Janumet (sitagliptin/metformin) provided significantly greater blood sugar lowering compared to metformin alone in patients with type 2 diabetes". Webwire.com, Jun. 8, 2009, p. 1-4. http://www.webwire.com/ViewPressRel.asp?aId=96695.
Merriam-Webster's Collegiate Dictionary, published 1998 by Merriam-Webster Inc. "prevent".
Mooradian, Arsharg D. et al. "Narrative Review: A Rational Approach to Starting Insulin Therapy" (2006) Annals of Internal Medicine, vol. 145, pp. 125-134.
Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.
Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.
Office Action mailed Feb. 16, 2012, U.S. Appl. No. 12/703,988, filed Feb. 11, 2010. Inventor: Peter Eickelmann.
Office Action mailed on Jun. 5, 2012. U.S. Appl. No. 12/673,319, filed Apr. 15, 2010. First named inventor: Klaus Dugi.
Office Action mailed Sep. 28, 2012. U.S. Appl. No. 12/704,019, filed Feb. 11, 2010. First named inventor: Wolfram Eisenreich.
Oku, Akira., et al; T-1095, An Inhibitor or renal Na+ -Glucose Cotransporters, May Provide a Novel Approach to Treating Diabetes; Diabetes (1999) vol. 48 pp. 1794-1800.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Perner, Richard J., et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.
Piya, Milan K. et al. "Emerging treatment options for type 2 diabetes" British Journal of Clinical Pharmacology, (2010) vol. 70, No. 5, pp. 631-644.
Printz, Richard L. et al. "Tweaking the Glucose Sensor: Adjusting Glucokinase Activity with Activator Compounds" Endocrinology, (2005) vol. 146, No. 9, pp. 3693-3695.
Rainier, Jon D. et al. "Aluminum- and Boron-Mediated C-Glycoside Synthesis from 1,2-Anhydroglycosides" Organic Letters, (2000) vol. 2, No. 17, pp. 2707-2709.
Randzio, Stanislaw L. et al. "Metastability and Instability of Organic Crystalline Substances" J. Phys. Chem. (2008) 112, pp. 1435-1444.
Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Revesz, Lasslo., et al; SAR of Benzoylpylpyridines and Benzophenones as p38 Alpha Map Kinase Inhibitors with Oral Activity; Bioorganic & Medicinal Chemistry Letters (2004) vol. 14 pp. 3601-3605.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Rudnic, Edward et al. "Oral Solid Dosage Forms" Remington's Pharmaceutical Sciences, 18th Ed, Gennaro, A.R. Ed, Macie Pub. Co. (1990) pp. 1633-1665.
Salgado Junior, et al. "Nonalcoholic fatty liver disease and obesity" Acti Cirugica Brasiliera (2006) vol. 21, Supp. 1, pp. 72-78.
Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Sherwin, Robert S. et al. "The Prevention or Delay of Type 2 Diabetes" Diabetes Care, (2002) vol. 25, No. 4, pp. 742-749.
Shin-Yakuzaigaku Souron. Edited by Sadasuke Okano, published by Nankodo. 1987, vol. 3, pp. 255-256.
Silverman, et al. "Handbook of Grignard Reagents" Marcel Dekker (1996) p. 82.
Singhal, Dharmendra et al. "Drug polymorphism and dosage form design: a practical perspective" Advanced Drug Delivery Reviews, 56, (2004) pp. 335-347.
Sommer, Michael Bech., et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.
Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.
Tanaka, Chikako "Therapeutic Drugs for Metabolic Diseases, Chapter 2" (2002) New Yakurigaku (New Pharmacology) pp. 524-527.
The Merck Manual Diagnosis and Therapy; Seventeenth Edition; "13 / Disorders of Carbohyrate Metabolism" Merck Research Laboratories (1999) pp. 165-177.
Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.
Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.
Threlfall, Terry "Structural and Thermodynamic Explanations of Ostwald's Rule" Organic Process Research & Development (2003) vol. 7, pp. 1017-1027.
Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.
U.S. Appl. No. 13/287,216, filed Nov. 2, 2011. Inventor: Rolf Grempler.
U.S. Appl. No. 13/367,739, filed Feb. 7, 2012. Inventor: Thomas Klein.
U.S. Appl. No. 13/413,702, filed Mar. 7, 2012. Inventor: Masanori Ito.
U.S. Appl. No. 13/484,506, filed May 31, 2012. Inventor: Marion Wienrich.
U.S. Appl. No. 13/539,713, filed Jul. 2, 2012. Inventor: Uli Broedl
U.S. Appl. No. 13/634,886, filed Sep. 14, 2012. Inventor: Peter Eickelmann.
U.S. Appl. No. 13/637,413, filed Sep. 26, 2012. Inventor: Rolf Grempler.
U.S. Appl. No. 13/693,239, filed Dec. 4, 2012. Inventor: Klaus Dugi.
U.S. Appl. No. 13/695,492, filed Oct. 31, 2012. Inventor: Thomas Klein.

(56) References Cited

OTHER PUBLICATIONS

U.S. Appl. No. 13/785,365, filed Mar. 5, 2013. Inventor: Masanori Ito.
U.S. Appl. No. 13/833,097, filed Mar. 15, 2013. Inventor: Eric Williams Mayoux.
U.S. Appl. No. 14/244,196, filed Apr. 3, 2014. Inventor: Uli Christian Broedl.
U.S. Appl. No. 14/244,208, filed Apr. 3, 2014. Inventor: Uli Christian Broedl.
U.S. Appl. No. 14/253,935, filed Apr. 16, 2014. Inventor: Uli Christian Broedl.
Ueta, Kiichiro., et al; Long-Term Treatment with the Na+ -Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.
Wallace, Debra J., et al; Cyclopropylboronic Acid: Synthesis and Suzuki Cross-Coupling Reactions; Tetrahedron Letters (2002) vol. 43 pp. 6987-6990; Pergamon Press.
Wang Y et al: "BI-1356. Dipeptidyl-peptidase IV inhibitor, antidiabetic agent" Drugs of the Future, Prous Science, ES,vol. 33, No. 6, Jun. 1, 2008, pp. 473-477.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.
www.who.int/medicinedocs/index/assoc/s14141e/s14141e.pdf "Addendum 1 to the use of stems in the selection of International Nonproprietary names (INN) for pharmaceutical substances" World Health Organization Jun. 19, 2007, pp. 1-3, XP007906327.
Xue, Song., et al; Zinc-mediated Synthesis of Alpha-C-Glycosided from 1,2-Anhydroglycosides; Synletters (2003) vol. 6 pp. 870-872.
Yamada, Yuichiro et al. "Clinic: Careful Progress in the Field and new Therapeutic Methods" Medical Online, (2007) vol. 220, No. 13, pp. 1219-1221.
Zhang, L. et al "Dapagliflozin treatment in patients with different stages of type 2 diabetes mellitus: effects on glycaemic control and body weight" Diabetes, Obesity and Metabolism (2010) vol. 12, No. 6, p. 510-515.
Abstract in English for German DE10109021, 2002.
Abstract in English for German DE2205815, 1972.
Abstract in English for German EP0023032, 1981.
Abstract in English for JP 2002/348279, Dec. 4, 2002.
Abstract in English for JP 2003/286287, Oct. 10, 2003.
Abstract in English, for KR20070111099, Nov. 11, 2007.
Adebowale, K.O. et al., "Modification and properties of African yam bean (Sphenostylis stenocarpa Hochst. Ex A. Rich.) Harms starch I: Heat moisture treatments and annealing." Food Hydrocolloids, 2009, vol. 23, No. 7, pp. 1947-1957.
Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Ahren, Bo; "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.
Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.
Alter, M. et al., "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.
American Diabetes Association, "Standards of Medical Care in Diabetes—2008." Diabetes Care, Jan. 2008, vol. 31, Supplement 1, pp. S12-S54.
Anonymous, Clinicaltrials.gov, 2008, No. NCT00622284, "Efficacy and Safety of BI 1356 in combination with metformin in patients with type 2 diabetes" p. 1-5.
Anstee, Quentin M. et al. "Mouse models in non-alcholic fatty liver disease and steatohepatitis research" (2006) International Journal of Expermental Pathology, vol. 87, pp. 1-16.
Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.
Augusti, D.V. et al., "Quantitative determination of the enantiomeric composition of thalidomide solutions by electrospray ionizatio tandem mass spectrometry". Chem Comm, 2002, p. 2242-2243.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.
Baetta, R. et al., "Pharmacology of Dipeptidyl Peptidase-4 Inhibitors." Drugs, 2011, vol. 71, No. 11, pp. 1441-1467.
Balaban, Y.H.et al., "Dipeptidyl peptidase IV (DDP IV) in NASH patients" Annals of Hepatology, vol. 6, No. 4, Oct. 1, 2007, pp. 242-250, abstract.
Balbach, S. et al., "Pharmaceutical evaluation of early development candidates the 100 mg-approach." International Journal of Pharmaceutics, 2004, vol. 275, pp. 1-12.
Balkan, B. et al, "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.
Bastin, R.J. et al., "Salt Selection and Optimization Procedures for Pharmaceutical New Chemical Entities". Organic Process Research and Development, 2000, vol. 4, p. 427-435.
Beljean-Leymarie et al., Hydrazines et hydrazones hétérocycliques. IV. Synthéses de dérivés de l'hydrazine dans la série des imidazo[4,5-d]pyridazinones-4, Can. J. Chem., vol. 61, No. 11, 1983, pp. 2563-2566.
Berge, S. et al., "Pharmaceutical Salts." Journal of Pharmaceutical Sciences, 1977, vol. 66, No. 1, pp. 1-19.
Bernstein, Joel "Polymorphism in Molecular Crystals." Oxford University Press, 2002, p. 9.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Brittain, H.G., "Methods for the Characterization of Polymorphs: X-Ray Powder Diffraction," Polymorphism in Pharmaceutical Solids, 1999, p. 235-238.
Bundgaard, H. "Design of prodrugs: Bioreversible derivatives for various functional groups and chemical entities". Royal Danish School of Pharmacy, 1985, p. 1-92.
Busso et al., "Circulating CD26 is Negatively Associated with Inflammation in Human and Experimental Arthritis," Am. J. Path., vol. 166, No. 2, Feb. 2005, pp. 433-442.
Byrn, Stephen R. "Solid-State Chemistry of Drugs." Academic Press, 1982, pp. 1-27.
Caira, M.R., "Crystalline polymorphism of organic compounds" Topics in Current Chemistry, Springer, Berlin, vol. 198, 1998, p. 163-208.

(56) References Cited

OTHER PUBLICATIONS

Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Chaykovska, L. et al., "Effects of DPP-4 Inhibitors on the Heart in a Rat Model of Uremic Cardiomyopathy." www.plosone.org, 2011, vol. 6, No. 11, p. e27861.
ChemGaroo, "Leaving Group." 1999, Retrieved online: http://www.chemgapedia.de/vsengine/vlu/vsc/en/ch/12/oc/vluorganik/substitution/sn_2/sn 2. vlu/Page/vsc/en/ch/12/oc/substitution/sn_2/abgangsgrupen/abgangsgruppe. vscml.html.
Chemical Abstract. EP412358, 1991:185517, Findeisen.
Chemical Abstract: FR2707641, 1995:543545, Dodey.
Chemical Abstract: No. 211513-37-0—Dalcetrapib. "Propanethioic acid, 2-methyl-,S-(2-[[[1-(2-ethylbutyl)cyclohexyl)carbonyl}amino}pheyl}-ester" . Formula: C23 H35 N O2 S. American Chemical Society. Sep. 20, 1998.
Chemical Abstract: No. 875446-37-0—Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1,1'-biphenyl]-2-yl]methyl]-4-methyl-,(4S,5R)-" Formula: C30 H25 F10 NO3. American Chemical Society, Feb. 28, 2006.
Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.
Chemical Abstracts Service, Database Accession number No. RN 668270-12-01, 2004, "1H-Purine-2,6-dione, 8- [(3R)-3-amino-1-piperidinyl]-7-(2-butyn-1-yl)-3,7-dihydro-3-methyl-1-[(4-methyl-2-quinazolinyl)methyl]".
Chemistry Review: Tradjenta, "NDA 201280, CMC Director Review Tradjenta (Linagliptin) Tablets" Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Clinical Trial NCT00622284 (published online at clinicaltrials.gov on Feb. 22, 2008).
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.
Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.
Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.
Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.
Cotton, M.L. et al., "L-649,923—The selection of an appropriate salt form and preparation of a stable oral formulation." International Journal of Pharmaceutics, 1994, vol. 109, Issue 3, pp. 237-249.
Crowe, E. et al., "Early identification and management of chronic kidney disease: summary of NICE guidance." British Medical Journal, 2008, vol. 337, pp. 812-815.
Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.
Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X,Nov. 1980, p. 1497-1500.
Dave, Rutesh H. "Overview of pharmaceutical excipients used in tablets and capsules." Drug Topics, Oct. 24, 2008.
Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.
Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.
Deacon, C.F., et al. Inhibitors of dipeptidyl peptidase IV: a novel approach for the prevention and treatment of Type 2 diabetes? Expert Opinion on Investigational Drugs, 2004, Sep., vol. 13, No. 9, p. 1091-1102.
Deacon, Carolyn F. et al. "Linaglipitn, a xanthine-based dipeptidyl peptidase-4 inhibitor with an unusual profile for the treatment of type 2 diabetes" Expert Opin. Investig. Drugs (2010) 19(1): 133-140.
Definition of "prevent", e-dictionary, Aug. 15, 2013, http://dictionary.reference.com/browse/prevent.
DeMeester, I. et al.; "CD26, let it cut or cut it down", Review: Immunology Today; Aug. 1999, vol. 20, No. 8 pp. 367-375.
Demuth, H-U. et al., "Type 2 diabetes—Therapy with dipeptidyl peptidase IV inhibitors". Biochimica et Biophysica Acta, vol. 1751(1), 2005, p. 33-44.
Diabetes Frontier, 2007, vol. 18, No. 2, p. 145-148.
Diabetes Health Center, "Diabetic Retinopathy—Prevention." Retrieved online Mar. 22, 2011. www.diabetes.webmd.com/tc/diabetic-retinopathy-prevention <http://www.diabetes.webmd.comitc/diabetic-retinopathy-prevention?print=true>.
Diabetesincontrol.com "EASD: Eucreas, a Combination of Galvus and Metformin, Recommended for Approval." Diabetes in Control.com, Sep. 25, 2007, Retrieved from internet on Nov. 30, 2012, http://www. diabetesincontrol.com/articles/53-diabetes-news/5145.
Diabetic Neuropathy, Retrieved online Mar. 6, 2012. www.mayoclinic.com/health/diabetic-neuropathy/DS01045/
METHOD=print&DSE <http://www.mayoclinic.com/health/diabetic-neuropathy/DS01045/METHOD=print&DSE>.
Drucker, et al.., The incretin system:glucagon-like peptide-1 receptor agonists and dipeptidyl peptidase-4 inhibitors in type 2 diabetes. Lancet, 2006, 368: 1696-705.
Dugi, K.A. et al., "BI 1356, a novel xanthine-based DPP-IV inhibitor, exhibits high potency with a wide therapeutic window and significantly reduces postprandial glucose excursions after an oGTT". Diabetologia, vol. 50, No. Suppl 1, Sep. 2007, p. S367, and 43rd Annual Meeting of the European Association for the Study of Diabetes; Amsterdam, Netherlands, Sep. 18-21, 2007.
Dunitz, J. et al., "Disappearing Polymorphs." Acc. Chem. Res. 1995, vol. 28, No. 4, pp. 193-200.
Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

(56) References Cited

OTHER PUBLICATIONS

Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.
Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.
eMedicine Health, "Diabetes Causes." Retrieved from internet on Aug. 22, 2013. <http://www.onhealth.com/diabetes_health/page3.htm#diabetes_causes>.
Eucreas Scientific Discussion, 2007, p. 1-27, www.emea.europa.eu/humandocs/PD/Fs/EPAR/eucreas/H-807-en6.pdf, Anonymous.
Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.
Ferry, Robert Jr., "Diabetes Causes." eMedicine Health, MedicineNet.com, 2013, Retrieved from internet on Aug. 22, 2013, http://www.onhealth.com/diabetes_health/page3.htm#diabetes_causes.
Florez, J. et al. "TCF7L2 Polymorphisms and Progression to Diabetes in the Diabetes Prevention Program." The New England Journal of Medicine, 2006, vol. 355, No. 3, pp. 241-250.
Florez, Jose C., et al., "TCF7L2 Polymorphisms and progression to diabetes in the diabetes prevention program". New England Journal of Medicine, MA Medical Society, vol. 355, No. 2, Jul. 20, 2006, p. 241-250.
Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.
Forst, T. T et al.' "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.
Fukushima et al., Drug for Treating Type II Diabetes (6), "action-mechanism of DPP-IV inhibitor and the availability thereof" Mebio, 2009, vol. 26, No. 8, p. 50-58.
Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.
Gallwitz, B. et al., "Saxagliptin, a dipeptidyl peptidase IV inhibitor for the treatment of type 2 diabetes". Drugs, vol. 11, No. 12, Dec. 2008, p. 906-917.
Gallwitz, B. et al., DPP IV inhibitors for the Treatment of Type 2 Diabetes; Diabetes Frontier (2007) vol. 18, No. 6 pp. 636-642.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
Geka, 2001, vol. 67, No. 11, p. 1295-1299.
Gennaro, Alfonso R. Remington Farmacia, 2003, Spanish copy: p. 828, English copy: pp. 711-712, Preformulation, Chapter 38.
Gennaro, Alfonso R., Remington Farmacia, 19th Edition, Spanish copy, 1995, p. 2470.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Giron, D.; Thermal Analysis and Calorimetric Methods in the Characterisation of Polymorphs and Solvates; Thermochimica Acta (1995) vol. 248 pp. 1-59.
Glucotrol XL (glipizide), package insert, Pfizer, Apr. 1, 2002.
Goldstein, L.A., et al., "Molecular cloning of seprase: a serine integral membrane protease from human melanoma." Biochimica et Biophysica Acta, vol. 1361, 1997, No. 1, pp. 11-19.
Gomez-Perez, et al, "Insulin Therapy:current alternatives", Arch. Med.Res. 36: p. 258-272 (2005).
Graefe-Mody et al., "The novel DPP-4 inhibitor BI 1356 (proposed tradename ONDERO) and Metformin can be Safely Co-administered Without Dose Adjustment." Poster No. 553-P ADA Jun. 6-10, 2008, San Francisco http://professional.diabetes.org/content/posters/2008/p553-p.pdf.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Graefe-Mody, U. et al., "Effect of Renal Impairment on the Pharmacokinetics of the Dipeptidyl Peptidase-4 Inhibitor Linagliptin." Diabetes, Obseity and Metabolism, 2011, pp. 939-946.
Greene, T.W, et al., "Protection for the Amino Group". Protective Groups in Organic Synthesis, 3rd edition, 1999, p. 494-653.
Groop, P.-H. et al., "Effects of the DPP-4 Inhibitor Linagliptin on Albuminuria in Patients with Type 2 Diabetes and Diabetic Nephropathy." 48th EASD Annual Meeting, Berlin, Abstract 36, Oct. 2012. <http://www.abstractsonline.com/Plan/ViewAbstract.aspx?sKey=0b0017b9-9e90-4695-b9af-b6870e96a921&cKey=421edb9c-b940-40f0-b282-8e61245561d5&mKey=2dbfcaf7-1539-42d5-8dda-0a94abb089e8>.
Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Hainer, Vojtech MD, PHD "Comparative Efficiency and Safety of Pharmacological Approaches to the Management of Obesity." Diabetes Care, 2011, vol. 34, Suppl. 2, pp. S349-S354.
Halimi, et al., "Combination treatment in the management of type 2 diabetes" focus on vildagliptin and metformin as a single tablet, Vascualr Health and Risk Management, 2008, 4(3) p. 481-92.
Haluzik, M. et al., "Renal Effects of DPP-4 Inhibitors: A Focus on Microalbuminuria." International Journal of Endocrinology, 2013, vol. 35, No. 6, pp. 1-7.
Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.
Hashida, Mitsuru, "Strategies for designing and developing oral administration formulations." Yakuji-Jiho, Inc., 1995, pp. 50-51.
Hayashi, Michio., "Recipe for Oral Hypoglycemic Agents to Pathological Condition" Pharmacy (2006) vol. 57, No. 9 pp. 2735-2739.
He, Y .L. et al., "The influence of hepatic impairment on the pharmacokinetics f the dipeptidyl peptidase IV (DPP-4) inhibitor vildagliptin" European Journal of Clinical Pharmacology, vol. 63, No. 7, May 8, 2007, p. 677-686.
Headland, K. et al., "The Effect of Combination Linagliptin and Voglibose on Glucose Control and Body Weight." 73rd Annual Meeting Science Session, ADA, Chicago, Jun. 21, 2013.
Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.
Heise, T. et al., "Treatment with BI 1356, a Novel and Potent DPP-IV Inhibitor, Significantly Reduces Glucose Excursions after an oGTT in Patients with Type 2 Diabetes." A Journal of the American Diabetes Association, Jun. 2007, vol. 56, Supplement 1, Poster No. 0588P.
Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.
Herman, Gary et al. "Co-Administration of MK-0431 and Metformin in Patients with Type 2 Diabetes Does Not Alter the

(56) References Cited

OTHER PUBLICATIONS

Pharmacokinetics of MK-0431 or Metformin" (2005) Journal of American Diabetes Association vol. 54, Supplement 1, 3 pgs.
Hermann, Robert, et al; Lack of Association of PAX4 Gene with Type 1 Diabetes in the Hungarian Populations; Diabetes (2005) vol. 54 pp. 2816-2819.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.
Hilfiker, R. et al., "Relevance of Solid-state Properties for Pharmaceutical Products." Polymorphism in the Pharmaceutical Industry, 2006, Chapter 1, pp. 1-19.
Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.
Hocher, B. et al., "The novel DPP-4 inhibitors linagliptin and BI 14361 reduce infarct size after myocardial ischemial reperfusion in rats." International Journal of Cardiology, 2013, vol. 167, pp. 87-93.
Holman, et al., "Addition of biphasic, prandial, or basal insulin to oral therapy in type 2 diabetes", N. England Journal Medicine, p. 1716-1730, 2007.
Horsford, E. N. "On the source of free hydrochloric acid in the gastric juice." Proceedings of the Royal Society of London, Published in 1868-1869, vol. 17, pp. 391-395.
Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.
Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.
Hull, R. et al., "Nephrotic syndrome in adults." British Medical Journal, 2008, vol. 336, pp. 1185-1190.
Hunziker, D. et al, "Inhibitors of DPP IV-recent advances and structural views", Current Topics in Medicinal Chemistry, 2005, vol. 5 issue 16, pp. 1623-1637.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
Inukai, T., "Treatment of Diabetes in Patients for Whom Metformin Treatment is Not Appropriate." Modern Physician, 2008, vol. 28, No. 2, pp. 163-165.
Isomaa, B. et al., "Cardiovascular Morbidity and Mortality Associated With the Metabolic Syndrome." Diabetes Care, 2001, vol. 24, No. 4, pp. 683-689.
Januvia; Patient Information; 2010.
Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 1, pp. 1-10.
Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.
John Hopkins Children's Center, "Liver Disorders and Diseases." Retrieved online May 26, 2014 <http://www.hopkinschildrens.org/non-alcoholic-fatty-liver-disease.aspx>.
Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.
Kanada, S. et al., "Safety, tolerability, pharmacokenetics and pharmacodynamics of multiple doses of BI 1356 (proposed tradename ONDERO), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA , Jun. 6-10, 2008.
Kelly. T., "Fibroblast activation protein-cx and dipeptidyl peptidase IV (CD26)P: Cell-surface proteases that activate cell signaling and are potential targets for cancern therapy". Drug Resisitence Update 8, 2005, vol. 8, No. 1-2, pp. 51-58.
Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.
Kharkevich, D.A., "Educational Literature" Pharmacology (1987) Third Edition, Meditsina Press, Moscow pp. 47-48.
Kibbe, A., Editor. Handbook of Pharmaceutical Excipients, Third Edition, Copovidon—pp. 196-197, Date of Revision: Dec. 16, 2008. Mannitol—pp. 424-425, Date of Revision: Feb. 19, 2009, Published in 2009.
Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.
Kim, D. et al., "(2R)-4-Oxo-4-(3-(Trifluoremethyl)-5,6-dihydro[1,2,4]triazolo[4,3-a]pyrazin-7(8H)-yl]-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.
Kim, Kwang-Rok et al., "KR-62436, 6-{2-{2-(5-cyano4,5-dihydropyrazol-1-yl)-2-oxoethylamino}ethylamino)nicotinonitrile, is a novel dipeptidyl peptidase-IV (DDP-IV inhibitor with anti-hyperglycemic activity" European Journal of Pharmacology 518, 2005, p. 63-70.
Klein, T. et al., "Linagliptin alleviates hepatic steatosis and inflammation in a mouse model of non-alcoholic steatohepatitis." Medical Molecular Morphology, 2014, vol. 47, pp. 137-149.
Knorr, M. et al., "Comparison of Direct and Indirect Antioxidant Effects of Linagliptin (BI 1356, Ondero) with other Gliptins—Evidence for Anti-Inflammatory Properties of Linagliptin". Free Radical Biology and medicine, Elsevier Science, U.S. vol. 49, Oct. 23, 2010, p. S197.
Komori, Kiyoshi., "Treatment of Diabetes in Patients for Whom Metforming Treatment is Not Appropriate" Modern Physician (2008) vol. 28, No. 2 pp. 163-165.
Korom, S. et al; Inhibition of CD26/dipeptidyl peptidase IV activity in vivo prolongs cardiac allograft survival in rat recipients1,2, Transplantation, May 27, 1997, vol. 63, No. 10, pp. 1495-1500.
Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.
Lakatos, P. L. et al., "Elevated Serum Dipeptidyl IV (CD26, EC 3.4.14.5) Activity in Experimental Liver Cirrhosis." European Journal of Clinical Investigation, 2000, vol. 30, No. 9, pp. 793-797.
Lakatos, P. L. et al "Elevated serum dipeptidyl peptidase IV (CD26, EC 3.4.14.5) activity in patients with primary biliary cirrhosis." Journal of Hepatol, 1999, vol. 30, p. 740.
Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.
Lee Jones, K. et al., "Effect of Metformin in Pediatric Patients With Type 2 Diabetes." Diabetes Care, 2002, vol. 25, No. 1, pp. 89-94.
Leibovitz, Cardiovascular Diabetology, Sitagliptin Treatment in diabetes patients presenting with acute coronary syndrome: results from the Acute Coronary Syndrome Israeli Survey, 2013.
Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.
Levien, T.L. et al, "New drugs in development for the treatment of diabetes", Diabetes Spectrum, American Diabetes Association, US, vol. 22, No. 2, Jan. 1, 2009, pp. 92-106.

(56) References Cited

OTHER PUBLICATIONS

Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.
Lim, Seoul National Univ. Bundang Hospital, Effect of a Dipeptyl Peptidase-IV Inhibitor, Des-Fluoro Sitagliptin, on Neointimal Formation after Balloon Injury in Rats, 2012, vol. 7, Issue 4.
Lovshin, J.A. et al., "Incretin-based therapies for type 2 diabetes mellitus." Nature Reviews Endocrinology, 2009, vol. 5, pp. 262-269.
Lyssenko, V. et al., "Mechanisms by which common variants in the TCF7L2 gene increase risk of type 2 diabetes." The Journal of Clinical Investigation, 2007, vol. 117, No. 8, pp. 2155-2163.
March, J. "Advanced Organic Chemistry: Reactions, Mechanisms, and Structure". Fourth Edition, 1992, pp. 652-653.
Matsumiya, Teruhiko, et al., "Therapeutic Drugs for Clinicians" Diagnosis and Treatment (2008) vol. 96, No. 2 pp. 389-390.
Matsumiya, Tokyo Medical University, Department of Pharmacology, Diagnosis and Therapy, vol. 96, No. 2, 2008.
Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.
McNay, David E.G. et al., "High fat diet causes rebound weight gain." Molecular Metabolism, 2013, vol. 2, pp. 103-108.
Medline Plus, "Obesity" 2013, Retrieved from internet on Aug. 22, 2013, http://www.nlm.nih.gov/medlineplus/obesity.html.
Mendes, F.D, et al. "Recent advances in the treatment of non-alcoholic fatty liver disease". Expert Opinion on Investigational Drugs, vol. 14, No. 1, Jan. 1, 2005, p. 29-35.
Naik, R. et al., "Latent Autoimmune Diabetes in Adults." The Journal of Clinical Endocrinology and Metabolism, 2009, vol. 94, No. 12, pp. 4635-4644.
Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.
National Program for Care Guidelines, "Type 2 Diabetes mellitus." 2002, First Edition, pp. 1-50.
Nauck, M. A. et al., "Efficacy and Safety of Adding the Dipeptidyl Peptidase-4 Inhibitor Alogliptin to Metformin Therapy in Patients with Type 2 Diabetes Inadequately Controlled with Metformin Monotherapy: A Multicentre, Randomised, Double-Blind, Placebo-Cotrolled Study." Clinical Practice, 2008, vol. 63, No. 1, pp. 46-55.
Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Diabetes Obesity and Metabolism, 2007, vol. 9, No. 2, pp. 194-205.
Nielsen, L., "Incretin Mimetics and DPP-IV Inhibitors for the Treatment of Type 2 Diabetes." DDT, 2005, vol. 10, No. 10, pp. 703-710.
Nihon Ijinpo, Japan Medicinal Journal, 2001, No. 4032, p. 137.
Nippon Rinsho, "Insulin Glargine", Tokyo Women's Medical Univ. Diabetes Center, 2011.
O'Farrell, et al., "Pharmacokinetic and Pharmacodynamic Assessments of the Dipeptidyl Peptidase-4 Inhibitor PHX1149: Double-Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.
Office Action for U.S. Appl. No. 10/695,597 mailed May 2, 2008.
Patani George A. et al.: "Bioisoterism : A Rational Approach in Drug Design", Chemical Reviews, 1996, vol. 96, No. 8, pp. 3147-3176.
Pearson, E. R. et al., "Variation in TCF7L2 Influences Therapeutic Response to Sulfonylureas." Diabetes, 2007, vol. 56, pp. 2178-2182.

Plummer, C.J.G. et al., "The Effect of Melting Point Distributions on DSC Melting Peaks." Polymer Bulletin, 1996, vol. 36, pp. 355-360.
Pospisilik, et al; ''Dipeptidyl Peptidase IV Inhibitor Treatment Stimulates ? -Cell Survival and Islet Neogenesis in Streptozotocin-Induced Diabetic Rats; Diabetes, vol. 52, Mar. 2003 pp. 741-750.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Pratley, R. et al., "Inhibition of DPP-4: a new therapeutic approach for the treatment of type 2 diabetes." Current Medical Research and Opinion, 2007, vol. 23, No. 4, pp. 919-931.
Villhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.
Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.
Wertheimer, et al., "Drug Delivery Systems improve pharmaceutical profile and faciliate medication adherence", Adv. Therapy 22: p. 559-577 (2005).
White, John R. Jr., "Dipeptidyl Peptidase-IV Inhibitors: Phamacological Profile and Clinical Use". Clinical Diabetes, Apr. 2008, vol. 26, No. 2, pp. 53-57.
Wikipedia, Annulation. Jun. 23, 2008, http://en.wikipedia.org/wiki/Annelation.
Wolff, M.E.: "Burger's Medicinal Chemistry and Drug Discovery" Fifth Edition, vol. 1: Principles and Practice, pp. 975-977, 1994, John Wiley & Sons, Inc.
World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.
X-Ray Diffraction. The United States Pharmacopeia, 2002, USP 25 NF20, p. 2088-2089.
Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.
Yasuda, et al. "E3024 3-but-2-ynyl-5-methyl-2-piperazin-1-y1-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Yoshikawa, Seiji et al.: Chemical Abstract of Japanese Patent No. WO 2003/104229 Preparation of purinone derivatives as dipeptidylpeptidase IV (DPP-IV) inhibitors, 2003.
Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.
Zejc, Alfred, et al; "Badania Nad Piperazynowymi Pochodnymi Dwumetyloksantyn" Acta Polon Pharm, XXXV (1976) Nr. 4 pages 417-421.
Zhong, Qing et al; "Glucose-dependent insulinotropic peptide stimulates proliferation and TGF-? release from MG-63 cells," Peptides 24 (2003) 611-616.
Zhu, G. et al., "Stabilization of Proteins Encapsulated in Cylindrical Poly(lactide-co-glycolide) Implants: Mechanism of Stabilization by Basic Additives." Pharmaceutical Research, 2000, vol. 17, No. 3, pp. 351-357.
Zimdahl, H. et al., "Influence of TCF7L2 gene variants on the therapeutic response to the dipeptidylpeptidase-4 inhibitor linagliptin." Diabetologia, 2014, vol. 57, pp. 1869-1875.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Prescribing Information, Package insert for Leprinton tablets 100mg, Manufacturer: Tatsumi Kagaku Co., Ltd., Mar. 2003.

(56) References Cited

OTHER PUBLICATIONS

Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.
Radermecker, Regis et al., "Lipodystrophy Reactions to Insulin." American Journal of Clinical Dermatology, 2007, vol. 8, pp. 21-28.
Rask-Madsen, C. et al., "Podocytes lose their footing." Nature, 2010, vol. 468, pp. 42-44.
Rhee et al.: "Nitrogen-15-Labeled Deoxynucleosides. 3. Synthesis of [3-15N]-2'-Deoxyadenosine" J. Am. Chem. Soc. 1990, 112, 8174-8175.
Rosenbloom, et al., "Type 2 Diabetes mellitus in the child and adolescent", Pediatric Diabetes, 2008, p. 512-526.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Salomon, J., et al; Ultraviolet and g-Ray-Induced Reactions of Nucleic Acid Constituents. Reactions of Purines with Amines; Photochemistry and Photobiology (1974) vol. 19 pp. 21-27.
Sarafidis, P. et al., "Cardiometabolic Syndrome and Chronic Kidney Disease: What is the link?"JCMS 2006, 1: p. 58-65.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Schwartz, M. S. et al., "Type 2 Diabetes Mellitus in Childhood: Obesity and Insulin Resistance". JAOA Review Article, vol. 108, No. 9, Sep. 2008, p. 518.
Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.
Shanks, N. et al., Are animal models predictive for humans?, PEHM, Philosophy, Ethics, and Humanaities in Medicine, 4(2), 2009, 1-20.
Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012. <http://www.abstractsonline.com/Plan/ViewAbstract.aspx?sKey=0b0017b9-9e90-4695-b9af-b6870e96a921&cKey=8eff47ae-db49-4c36-a142-848ac068c405&mKey=2dbfcaf7-1539-42d5-8dda-0a94abb089e8>.
Sheperd, Todd M. et al., "Efective management of obesity." The Journal of Family Practice, 2003, vol. 52, No. 1, pp. 34-42.
Shintani, Maki, et al., "Insulin Resistance and Genes" Circulatory Sciences (1997) vol. 17, No. 12 pp. 1186-1188.
Shu, L. et al., "Decreased TCF7L2 protein levels in type 2 diabetes mellitus correlate with downregulation of GIP- and GLP-1 receptors and impaired beta-cell function." Human Molecular Genetics, 2009, vol. 18, No. 13, pp. 2388-2399.
Shu, L. et al., "Transcription Factor 7-Like 2 Regulates B-Cell Survival and Function in Human Pancreatic Islets." . Diabetes, 2008, vol. 57, pp. 645-653.
Silverman, G. et al., "Handbook of Grignard Reagents." 1996, Retrieved online: <http://books.google.com/books?id=82CaxfY-uNkC&printsec=frontcover&dq=intitle:Handbook+intitle:of+intitle:Grignard+intitle:Reagents&hl=en&sa=X&ei=g06GU5SdOKngsATphYCgCg&ved=0CDYQ6AEwAA#v=onepage&q&f=false>.

Singhal, D. et al., "Drug polymorphism and dosage form design: a practical perspective." Advanced Drug Delivery Reviews, 2004, vol. 56, pp. 335-347.
Sortino, M.A. et al., "Linagliptin: a thorough characterization beyond its clinical efficacy." Frontiers in Endocrinology, 2013, vol. 4, Article 16, pp. 1-9.
St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.
Stahl, P.H., "Handbook of Pharmaceutical Salts" C.G. Wermuth, Wiley-VCH, 2002, pp. 1-374.
Standl, E. et al., "Diabetes and the Heart." Diabetes Guidelines (DDG), 2002, pp. 1-25.
Sune Negre, J. M. "New Galenic Contributions to Administration Forms". Continued Training for Hospital Pharmacists 3.2., (Publication date unavailable), Retrieved from internet on Feb. 23, 2011, http://www.ub.es/legmh/capitols/sunyenegre.pdf.
Suzuki, Y. et al., "Carbon-Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.
Tadayyon, M. et al., "Insulin sensitisation in the treatment of Type 2 diabetes." Expert Opinion Investigative Drugs, 2003, vol. 12, No. 3, pp. 307-324.
Tamm, E, et al., "Double-blind study comparing the immunogenicity of a licensed DTwPHib-CRM197 conjugate vaccine (Quattvaxem TM) with three investigational, liquid formulations using lower doses of Hib-CRM197 conjugate". Science Direct, Vaccine, Feb. 2005, vol. 23, No. 14, p. 1715-1719.
Tanaka, S.. et al; "Suppression of Arthritis by the Inhibitors of Dipeptidyl Peptidase IV," In. J. Immunopharmac., vol. 19, No. 1, pp. 15-24, 1997.
Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.
Third Party Observation for application No. EP20070728655, May 13, 2013.
Thomas, L, et al: "BI 1356, a novel and selective xanthine beased DPP-IV inhibitor, exhibits a superior profile when compared to sitagliptin and vildagliptin." Diabetologoa, vol. 50, No. Suppl. 1, Sep. 2007, p. S363.
Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563.
Thomas, Leo et al: "(R)-8-(3-Amino-piperidin-1-yl)-7-but-2-ynyl-3-methyl-1- (4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors." Journal of Pharmacology and Experimental Therapeutics, 2008, vol. 325, No. 1, pp. 175-182.
Thornber, C.W., "Isosterism and Molecular Modification in Drug Design." Chemical Society Reviews, 1979, pp. 563-580.
Tounyoubyou, "Symposium-19: Future Perspectives on Incretion Therapy in Diabetes." 2008, vol. 51, Suppl. 1, p. S-71, S19-2.
Tradjenta, Highlights of Prescribing Information (revised Sep. 2012).
Tribulova, N. et al. "Chronic Disturbances in No Production Results in Histochemical and Subcellular Alterations of the Rat Heart." Physiol. Res., 2000, vol. 49, No. 1, pp. 77-88.
Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemic in type 2 Diabetic rats", J. Pharm Exp. 2011, vol. 339, No. 1, p. 228-237.

(56) References Cited

OTHER PUBLICATIONS

Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013. <http://www.abstractsonline.com/Plan/ViewAbstract.aspx?sKey=e68ac573-fe45-4c2f-9485-6270854fc10b&cKey=3c387569-04de-4f8c-b025-b358df91ca64&mKey=%7b89918D6D-3018-4EA9-9D4F-711F98A7AE5D%7d>.

U.S. Appl. No. 12/724,653, filed Mar. 16, 2010—Xanthine Derivatives, the Preparation Thereof and Their Use as Pharmaceutical Compositions. Inventor: Frank Himmelsbach, et al.

U.S. Appl. No. 12/767,855, filed Apr. 27, 2010—Xanthine Derivatives, the Preparation Thereof and Their use as Pharmaceutical Compositions. Inventor: Frank Himmelsbach, et al.

Uhlig-Laske, B. et al., "Linagliptin, a Potent and Selective DPP-4 Inhibitor, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.

United Healthcare, "Diabetes." Retrieved from internet on Aug. 22, 2013, http://www.uhc.com/source4women/health_topics/diabetesirelatedinformation/dOf0417b073bf110VgnVCM1000002f1Ob1Oa_. htm.

Ahren, Bo "Novel combination treatment of type 2 diabetes DPP-4 inhibition + metformin." Vascular Health and Risk Management, 2008, vol. 4, No. 2, pp. 383-394.

Blech, S. et al., "The Metabolism and Disposition of the Oral Dipeptidyl Peptidase-4 Inhibitor, Linagliptin, in Humans", Drug Metabolism and Disposition, 2010, vol. 38, No. 4, p. 667-678.

Cheon, et al., Biochemical Pharmacology, "Inhibition of dipeptidyl IV by novel inhibitors with pyrazolidine scaffold", 2005, vol. 70, p. 22-29.

Clinical Trials, No. NCT00309608, "Efficacy and Safety of BI 1356 BS in Combination with Metformin in Patients With type2 Diabetes" 2009, pp. 1-3.

Craddy, P. et al., "Comparative Effectiveness of Dipeptidylpeptidase-4 Inhibitors in Type 2 Diabetes: A Systematic Review and Mixed Treatment Comparison." Diabetes Therapy, 2014, vol. 5, No. 1, pp. 1-41.

Drucker, Daniel J., "Dipeptidyl Peptidase-4 Inhibition and the Treatment of Type 2 Diabetes." Diabetes Care, 2007, vol. 30, No. 6, pp. 1335-1343.

Greischel, et al., Drug Metabolism and Deposition, "The Dipeptidyl Peptidase-4 Inhibitor Linagliptin Exhibits Time-and Dpse-Dependent Localization in Kidney, Liver, and Intestine after Intravenous Dosing: Results from High Resolution Autoradiography in Rats", 2010, vol. 38, No. 9, p. 1443-1448.

Gupta, V. et al., "Choosing a Gliptin." Indian Journal of Endocrinology and Metabolism, 2011, vol. 15, No. 4, pp. 298-308.

Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.

International Search Report and Written Opinion for PCT/EP2013/054524 mailed on Apr. 24, 2013.

Konstantinou, D. M. et al., "Pathophysiology-based novel pharmacotherapy for heart failure with preserved ejection fraction." Pharmacology & Therapeutics, 2013, vol. 140, No. 2, pp. 156-166.

Linagliptin Monograph, Published by VACO PBM-SHG US Veteran's Administration, 2011, pp. 1-17.

Schillinger, M. et al., "Restenosis after percutaneous angioplasty: the role of vascular inflammation." Vascular Health and Risk Management, 2005, vol. 1, No. 1, pp. 73-78.

Schurmann, C. et al., "The Dipeptidyl Peptidase-4 Inhibitor Linagliptin Attenuates Inflammation and Accelerates Epithelialization in Wounds of Diabetic ob/ob Mice." The Journal of Pharmacology and Experimental Therapeutics, 2012, vol. 342, No. 1, pp. 71-80.

Takeda Press Release: "Voglibose (BASEN) for the prevention of type 2 diabetes mellitus: A Randomized, Double-blind Trial in Japanese Subjects with Impaired Glucose Tolerance." 2008, Retrieved online Jul. 6, 2015. https://www. takeda.com/news/2008/20080526_3621.html.

Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.

Vichayanrat, A. et al., "Efficacy and safety of voglibose in comparison with acarbose in type 2 diabetic patients." Diabetes Research and Clinical Practice, 2002, vol. 55, pp. 99-103.

Vickers, 71st Scientific Session of the American Diabetes Association, "The DPP-4 inhibitor linagliptin is weight neutral in the DIO rat but inhibits the weight gain of DIO animals withdrawn from exenatide", vol. 60, Jul. 2011.

Weber, Ann E., "Dipeptidyl Peptidase IV Inhibitors for the Treatment of Diabetes." Journal of Medicinal Chemistry, 2004, vol. 47, pp. 4135-4141.

WebMD, Autoimmune Diseases: What Are They? Who Gets Them? "What Are Autoimmune Disorders?" 2015, pp. 1-3. Retrieved online Jul. 9, 2015. http://www.webmd.com/a-to-z-guides/autoimmune-diseases.

Witteles, R. M. et al., "Dipeptidyl Peptidase 4 Inhibition Increases Myocardial Glucose Uptake in Nonischemic Cardiomyopathy." Journal of Cardiac Failure, 2012, vol. 18, No. 10, pp. 804-809.

Zhimei, Xiao et al., "Study progression of oral drugs for treatment of type II diabetes." Drug Evaluation, 2004, vol. 1, No. 2, pp. 138-143.

Turner, R.C. et al., "Glycemic Control With Diet, Sulfonylurea, Metformin, or Insulin in Patients With Type 2 Diabetes Mellitus Progressive Requirement for Multiple Therapies (UKPDS 49)" The Journal of the American Medical Association, 1999, vol. 281, No. 21, pp. 2005-2012.

Van Heek, M. et al., "Ezetimibe, a Potent Cholesterol Absorption Inhibitor, Normalizes Combined Dyslipidemia in Obese Hyperinsulinemic Hamsters." Diabetes, 2001, vol. 50, pp. 1330-1335.

Vincent, S.H. et al., "Metabolism and Excretion of the Dipeptidyl Peptidase 4 Inhibitor [14C]Sitagliptin in Humans." Drug Metabolism and Disposition, 2007, vol. 35, No. 4, pp. 533-538.

Yale, Jean-Francois, "Oral Antihyperglycemic Agents and Renal Disease: New Agents, New Concepts." Journal of the American Society of Nephrology, 2005, vol. 16, Suppl. 1, pp. S7-S10.

Yap, W.S. et al., "Review of management of type 2 diabetes mellitus." Journal of Clinical Pharmacy and Therapeutics, 1998, vol. 23, pp. 457-465.

Yokoyama< "Prevalence of albumineria and renal insufficiency and associated clinical factors in type 2 diabetes: the Japan Diabetes clinical data Management study(JDDM15)" Nephrol Dial Transplant (2009) 24: 1212-1219 Advance Access Pub 2008.

Zander, M. et al., "Additive Glucose-Lowering Effects of Glucagon-Like Peptide-1 and Metformin in Type 2 Diabetes." Diabetes Care, 2001, vol. 24, No. 4, pp. 720-725.

Zerilli, T. et al., "Sitagliptin Phosphate: A DPP-4 Inhibitor for the Treatment of Type 2 Diabetes Mellitus." Clinical Therapeutics, 2007, vol. 29, No. 12, pp. 2614-2634.

Abstract for AU 2003280680, Jun. 18, 2004.

Abstract for AU 2009224546, Sep. 17, 2009.

Abstract in English for DE19705233, Aug. 13, 1998.

Actos Prescribing Information, 1999, pp. 1-26.

Ahren, B. et al., "Twelve- and 52-Week Efficacy of the Dipeptidyl Peptidase IV Inhibitor LAF237 in Metformin-Treated Patients With Type 2 Diabetes." Diabetes Care, 2004, vol. 27, No. 12, pp. 2874-2880.

American Association of Clinical Endocrinologists, "Medical Guidelines for Clinical Practice for the Management of Diabetes Mellitus." Endocrine Practice, 2007, Col. 13, Suppl. 1, pp. 1-68.

Banker, Gilbert S., "Prodrugs." Modern Pharmaceutics Third Edition, Marcel Dekker, Inc., 1996, p. 596.

Beauglehole, Anthony R., "N3-Substituted Xanthines as Irreversible Adenosine Receptor Antagonists." Ph.D. Thesis, Deakin University, Australia, 2000, pp. 1-168.

(56) References Cited

OTHER PUBLICATIONS

Canadian Diabetes Association, "Pharmacologic Management of Type 2 Diabetes." Canadian Journal of Diabetes, 2003, vol. 27, Suppl. 2, pp. S37-S42.
Chiasson, J.-L et al., "The Synergistic Effect of Miglitol Plus Metformin Combination Therapy in the Treatment of Type 2 Diabetes." Diabetes Care, 2001, vol. 24, No. 6, pp. 989-994.
Clinical Trial Protocol, "A Randomised, Double-blind, Placebo-controlled, Five Parallel Groups Study Investigating the Efficacy and Safety of BI 1356 BS." Boehringer Ingelheim Pharmaceuticals, last updated on Jun. 24, 2014.
Clinical Trial, NCT00622284, clinicaltrials.gov, updated Feb. 22, 2008.
Clinical Trials NCT00601250, clinicaltrials.gov, Jan. 25, 2008.
Clinical Trials: NCT00103857, "A Multicenter, Randomized, Double-Blind Factorial Study of the Co-Administration of MK0431 and Metformin in Patients With Type 2 Diabetes Mellitus Who Have Inadequate Glycemic Control" last updated on Apr. 27, 2015.
Clinical Trials: NCT00309608, "Efficacy and Safety of BI 1356 BS (Linagliptin) in Combination With Metformin in Patients With type2 Diabetes" Boehringer Ingelheim Pharmaceuticals, last updated on Jun. 24, 2014.
Colorcon, "Lactose Replacement with Starch 1500 in a Direct Compression Formula." 2005, pp. 1-4.
Colorcon, "Reducing Coated Tablet Defects from Laboratory through Production Scale: Performance of Hypromellose or Polyvinyl Alcohol-Based Aqueous Film Coating Systems." Opadry II, 2009, pp. 1-7.
Deacon, Carolyn F., "Dipeptidyl peptidase 4 inhibition with sitagliptin: a new therapy for Type 2 diabetes." Expert Opinion on Investigational Drugs, 2007, vol. 16, No. 4, pp. 533-545.
Gwaltney, S.L. Il et al., "Inhibitors of Dipeptidyl Peptidase 4." Annual Reports in Medicinal Chemistry, 2005, vol. 40, pp. 149-165.
Halimi, "Combination treatment in the management of type 2 diabetes: focus on vildagliptin and metformin as a single tablet", Vascular Health and Risk Management, 2008 481-92.
He, Y.L. et al., "The Influence of Renal Impairment on the Pharmacokinetics of Vildagliptin." Clinical Pharmacology & Therapeutics, 2007, vol. 81, Suppl. 1, Abstract No. PIII-86.
Hinke, S.A. et al., "Metformin Effects on Dipeptidylpeptidase IV Degradation of Glucagon-like Peptide-1." Biochemical and Biophysical Research Communications, 2002, vol. 291, No. 5, pp. 1302-1308.
Hinke, S.A. et al., "On Combination Therapy of Diabetes With Metformin and Dipeptidyl Peptidase IV Inhibitors." . Diabetes Care, 2002, vol. 25, No. 8, pp. 1490-1492.
Hinnen, D. et al., "Incretin Mimetics and DPP-IV Inhibitors: New Paradigms for the Treatment of Type 2 Diabetes." Journal of the American Board of Family Medicine, 2006, vol. 19, No. 6, pp. 612-620.
Inzucchi, Silvio E., "Oral Antihyperglycemic Therapy for Type 2 Diabetes." The Journal of the American Medical Association, 2002, vol. 287, No. 3, pp. 360-372.
Janumet Prescribing Information, revised Jan. 2008.
Januvia Prescribing Information and Product Label, 2006.
Kiraly, K. et al., "The dipeptidyl peptidase IV (CD26, EC 3.4.14.5) inhibitor vildagliptin is a potent antihyperalgesic in rats by promoting endomorphin-2 generation in the spinal cord." European Journal of Pharmacology, 2011, vol. 650, pp. 195-199.
Kirpichnikov, D. et al., "Metformin: An Update." Annals of Internal Medicine, 2002, vol. 137, No. 1, pp. 25-33.
Knowler, W.C. et al., "Reduction in the Incidence of Type 2 Diabetes with Lifestyle Intervention or Metformin." The New England Journal of Medicine, 2002, vol. 346, No. 6, pp. 393-403.
Lachman, L. et al., "The Theory and Practice of Industrial Pharmacy." Varghese Publishing House, Third Edition, 1987, pp. 190-194.
Lindsay, J.R. et al., "Inhibition of dipeptidyl peptidase IV activity by oral metformin in Type 2 diabetes." Diabetic Medicine, 2005, vol. 22, pp. 654-657.
Lu, "High prevlaence of albuminuria in population based patients diagnosed with type 2 diabetes in the Shanghai downtown", Diabestes Research and Clinical Practice (2007) 184-192.
Mathieu, C. et al. "Antihyperglycaemic therapy in elderly patients with type 2 diabetes: potential tole of incretin mimetics and DPP-4 inhibitors." International Journal of Clinical Practice, 2007, vol. 61, Suppl. 154, pp. 29-37.
Merck Manual of Diagnosis and Therapy: "Obesity." 1999, 17th Edition, Chapter 5, pp. 58-62.
Mikhail, Nasser, "Incretin mimetics and dipeptidyl peptidase 4 inhibitors in clinical trials for the treatment of type 2 diabetes." Expert Opinion on Investigational Drugs, 2008, vol. 17, No. 6, pp. 845-853.
Novartis AG, Investor Relations Release, "Galvus, a new oral treatment for type 2 diabetes, receives positive opinion recommending European Union approval." Securities and Exchange Commission, Form 6-K, 2007, pp. 1-4.
Pietruck, F. et al., "Rosiglitazone is a safe and effective treatment option of new-onset diabetes mellitus after renal transplantation." Transplant International, 2005, vol. 18, pp. 483-486.
Sulkin, T.V. et al., "Contraindications to Metformin Therapy in Patients With NIDDM." Diabetes Care, 1997, vol. 20, No. 6, pp. 925-928.

\* cited by examiner

US 9,555,001 B2

PHARMACEUTICAL COMPOSITION AND USES THEREOF

The present invention relates to pharmaceutical compositions containing a fixed dose combination (FDC) comprising
a DPP-4 inhibitor drug (particularly 1-[(4-methyl-quinazolin-2-yl)methyl]-3-methyl-7-(2-butyn-1-yl)-8-(3-(R)-amino-piperidin-1-yl)-xanthine, also named linagliptin) and/or a SGLT-2 inhibitor drug (particularly 1-chloro-4-(β-D-glucopyranos-1-yl)-2-[4-((S)-tetrahydrofuran-3-yloxy)-benzyl]-benzene, also named Compound "A" herein), and
metformin (particularly metformin hydrochloride) in extended release form (metformin XR); processes for the preparation thereof, and their use to treat certain diseases.

In particular, the present invention relates to a pharmaceutical composition comprising a fixed dose combination of an extended release form of metformin hydrochloride, optionally seal or barrier coated, which is further coated with an immediate release form of 1-[(4-methyl-quinazolin-2-yl)methyl]-3-methyl-7-(2-butyn-1-yl)-8-(3-(R)-amino-piperidin-1-yl)-xanthine (linagliptin) and/or 1-chloro-4-(β-D-glucopyranos-1-yl)-2-[4-((S)-tetrahydrofuran-3-yloxy)-benzyl]-benzene (Compound "A").

Further, the present invention relates to a pharmaceutical composition, particularly a solid preparation (e.g. an oral solid dosage form, such as e.g. a tablet), comprising or consisting essentially of
a) an inner extended release core comprising metformin (particularly metformin hydrochloride) and one or more excipients;
b) an optional intermediate seal and/or barrier coating; and
c) an outer immediate release coating comprising at least one active pharmaceutical ingredient selected from
a DPP-4 inhibitor, preferably linagliptin, and
a SGLT-2 inhibitor, preferably Compound "A",
and one or more excipients.

In a more detailed aspect, the present invention relates to a pharmaceutical composition, particularly a solid preparation (e.g. an oral solid dosage form, such as a tablet) of a selected dipeptidyl peptidase-4 (DPP-4) inhibitor (preferably linagliptin, particularly in immediate release form) and metformin (particularly metformin hydrochloride) in extended release form (metformin XR). In one embodiment of this aspect, the present invention relates to a pharmaceutical composition, particularly a solid preparation (e.g. an oral solid dosage form, such as a tablet), comprising a fixed dose combination of an extended release form of metformin hydrochloride, optionally seal and/or barrier coated, and further coated with an immediate release form of linagliptin.

In another more detailed aspect, the present invention relates to a pharmaceutical composition, particularly a solid preparation (e.g. an oral solid dosage form, such as a tablet) of a selected SGLT-2 inhibitor (preferably 1-chloro-4-(β-D-glucopyranos-1-yl)-2-[4-((S)-tetrahydrofuran-3-yloxy)-benzyl]-benzene, particularly in immediate release form) and metformin (particularly metformin hydrochloride) in extended release form (metformin XR). In one embodiment of this aspect, the present invention relates to a pharmaceutical composition, particularly a solid preparation (e.g. an oral solid dosage form, such as a tablet), comprising a fixed dose combination of an extended release form of metformin hydrochloride, optionally seal and/or barrier coated, and further coated with an immediate release form of 1-chloro-4-(β-D-glucopyranos-1-yl)-2-[4-((S)-tetrahydrofuran-3-yloxy)-benzyl]-benzene.

In a further more detailed aspect, the present invention relates to a pharmaceutical composition, particularly a solid preparation (e.g. an oral solid dosage form, such as e.g. a tablet), comprising
a first component, part or composition comprising metformin (particularly metformin hydrochloride) in extended release form and one or more excipients, and
a second component, part or composition comprising a selected dipeptidyl peptidase-4 (DPP-4) inhibitor (preferably linagliptin), particularly in immediate release form, and one or more excipients.

In particular, the present invention relates to a pharmaceutical composition, particularly a solid preparation (e.g. an oral solid dosage form, such as a tablet), comprising an extended release form of metformin hydrochloride, optionally seal and/or barrier coated, and further coated with an immediate release form of linagliptin.

In another further more detailed aspect, the present invention relates to a pharmaceutical composition, particularly a solid preparation (e.g. an oral solid dosage form, such as e.g. a tablet), comprising
a first component, part or composition comprising metformin (particularly metformin hydrochloride) in extended release form and one or more excipients, and
a second component, part or composition comprising a selected SGLT-2 inhibitor (preferably 1-chloro-4-(β-D-glucopyranos-1-yl)-2-[4-((S)-tetrahydrofuran-3-yloxy)-benzyl]-benzene), particularly in immediate release form, and one or more excipients.

In particular, the present invention relates to a pharmaceutical composition, particularly a solid preparation (e.g. an oral solid dosage form, such as a tablet), comprising an extended release form of metformin hydrochloride, optionally seal and/or barrier coated, and further coated with an immediate release form of 1-chloro-4-(β-D-glucopyranos-1-yl)-2-[4-((S)-tetrahydrofuran-3-yloxy)-benzyl]-benzene.

In a yet further more detailed aspect, the present invention relates to a pharmaceutical composition, particularly a solid preparation (e.g. an oral solid dosage form, such as e.g. a tablet), comprising or consisting essentially of
a) an inner extended release core comprising metformin (particularly metformin hydrochloride) and one or more excipients,
bi) an optional seal coating,
bii) an optional barrier coating, and
c) an immediate release coating comprising a selected dipeptidyl peptidase-4 (DPP-4) inhibitor (preferably linagliptin) and one or more excipients.

In another yet further more detailed aspect, the present invention relates to a pharmaceutical composition, particularly a solid preparation (e.g. an oral solid dosage form, such as e.g. a tablet), comprising or consisting essentially of
a) an inner extended release core comprising metformin (particularly metformin hydrochloride) and one or more excipients,
bi) an optional seal coating,
bii) an optional barrier coating, and
c) an immediate release coating comprising a selected SGLT-2 inhibitor (preferably 1-chloro-4-(β-D-glucopyranos-1-yl)-2-[4-((S)-tetrahydrofuran-3-yloxy)-benzyl]-benzene) and one or more excipients.

Particularly, the pharmaceutical compositions of this invention comprise an inner core formulation of metformin hydrochloride comprising a swellable and/or extended release material.

In an embodiment, the pharmaceutical compositions of this invention comprise an inner extended release core which is a formulation (e.g. matrix formulation) comprising metformin hydrochloride, a swellable and/or extended release material, and one or more further excipients.

Particularly, the pharmaceutical compositions of this invention comprise an outer coat of active pharmaceutical ingredient (API) (linagliptin and/or 1-chloro-4-(β-D-glucopyranos-1-yl)-2-[4-((S)-tetrahydrofuran-3-yloxy)-benzyl]-benzene) in an immediate release polymer film.

The extended-release mechanism for the metformin HCl core may be based on an expandable polymeric swelling formulation that increases gastric retention and extends drug release from the matrix.

This metformin HCl core may be then film-coated (spray-coated) with up to four layers (e.g. barrier coat layer, immediate-release active coat layer, color coat layer, final coat layer), one of which (active coat layer) contains the active pharmaceutical ingredient (API) (linagliptin or 1-chloro-4-(β-D-glucopyranos-1-yl)-2-[4-((S)-tetrahydrofuran-3-yloxy)-benzyl]-benzene), to add the immediate-release active component.

Further, the present invention relates to a coating process (e.g. coating technology and processing conditions) and immediate release coating formulations of active pharmaceutical ingredients (API) in low doses (typically in doses of 0.5 to 25 mg) on top of tablet cores comprising active pharmaceutical ingredients (API) in high doses (typically in doses of 500-1500 mg) preferably, but not exclusively on extended release tablets. Anyhow, essential parts of the formulation and the process of this invention may be also applicable to any other fixed dose combination with the described setting.

An aim of the present invention is to provide a pharmaceutical composition comprising a combination of a selected DPP-4 inhibitor (preferably linagliptin, particularly in immediate release form), and metformin (particularly metformin hydrochloride) in extended release form.

Another aim of the present invention is to provide a pharmaceutical composition comprising a combination of a selected SGLT-2 inhibitor (preferably 1-chloro-4-(β-D-glucopyranos-1-yl)-2-[4-((S)-tetrahydrofuran-3-yloxy)-benzyl]-benzene, particularly in immediate release form), and metformin (particularly metformin hydrochloride) in extended release form.

The objectives of are to identify suitable formulations and processing conditions, such as e.g. of a coat of linagliptin or of 1-chloro-4-(β-D-glucopyranos-1-yl)-2-[4-((S)-tetrahydrofuran-3-yloxy)-benzyl]-benzene on top metformin XR cores, providing adequate:

Chemical stability of the API (particularly linagliptin) in the API film coat,
Assay of linagliptin or 1-chloro-4-(β-D-glucopyranos-1-yl)-2-[4-((S)-tetrahydrofuran-3-yloxy)-benzyl]-benzene in the API film-coat (e.g. 95-105%),
Content uniformity of linagliptin or 1-chloro-4-(β-D-glucopyranos-1-yl)-2-[4-((S)-tetrahydrofuran-3-yloxy)-benzyl]-benzene (e.g. RSD <3%) in the API film-coat,
Low defect rate of the API-film during film coating process,
Fast dissolution of the API from the API film-coat and no changes of XR Metformin HCl dissolution, due to the API coating with immediate release of linagliptin or 1-chloro-4-(β-D-glucopyranos-1-yl)-2-[4-((S)-tetrahydrofuran-3-yloxy)-benzyl]-benzene,
Processing aspects of coating process/technology, processing conditions and immediate release API (linagliptin or Compound "A") coating formulations (API film coat),
Processing aspects of coating process/technology, processing conditions and immediate release API (linagliptin or Compound "A") coating formulations on top of metformin extended release tablets.

A particular objective of the present invention is to provide a pharmaceutical composition and suitable coating process with very broad range of drug substance (linagliptin or Compound "A")/drug substance (metformin) ratio: 1:400-1:40. And the ratio of very low dosed API, e.g. linagliptin with 1 mg or 2.5 mg to very high dosed metformin with 1000 mg and more. And the suitable immediate release dissolution of the low dosed API with high dosed extended release metformin.

The unit dosage strength of the metformin hydrochloride for incorporation into the fixed-dose combination of the present invention is preferably 500, 750, 850 or 1000 milligrams, or even more (e.g. 1500 mg).

These unit dosage strengths of metformin hydrochloride represent the dosage strengths approved in the U.S. for marketing to treat Type 2 diabetes.

The unit dosage strength of linagliptin for incorporation into the fixed-dose combination of the present invention is preferably in the range from 0.5 to 10 mg, for particular example 2.5 or 5 milligrams, or even less (e.g. 0.5 mg or 1 mg).

The unit dosage strength of 1-chloro-4-(β-D-glucopyranos-1-yl)-2-[4-((S)-tetrahydrofuran-3-yloxy)-benzyl]-benzene for incorporation into the fixed-dose combination of the present invention is preferably in the range from 5 to 25 mg, for example 5, 10, 12.5 or 25 milligrams.

Specific embodiments of dosage strengths for linagliptin and metformin hydrochloride in the fixed-dose combinations of the present invention are the following:
(1) 5 milligrams of linagliptin and 1000 milligrams metformin hydrochloride;
(2) 2.5 milligrams of linagliptin and 1000 milligrams metformin hydrochloride;
(3) 2.5 milligrams of linagliptin and 750 milligrams metformin hydrochloride.

Specific embodiments of dosage strengths for 1-chloro-4-(β-D-glucopyranos-1-yl)-2-[4-((S)-tetrahydrofuran-3-yloxy)-benzyl]-benzene and metformin hydrochloride in the fixed-dose combinations of the present invention are the following:
(1) 25 milligrams of 1-chloro-4-(β-D-glucopyranos-1-yl)-2-[4-((S)-tetrahydrofuran-3-yloxy)-benzyl]-benzene and 1000 milligrams metformin hydrochloride;
(2) 12.5 milligrams of 1-chloro-4-(β-D-glucopyranos-1-yl)-2-[4-((S)-tetrahydrofuran-3-yloxy)-benzyl]-benzene and 1000 milligrams metformin hydrochloride;
(3) 12.5 milligrams of 1-chloro-4-(β-D-glucopyranos-1-yl)-2-[4-((S)-tetrahydrofuran-3-yloxy)-benzyl]-benzene and 750 milligrams metformin hydrochloride;
(4) 10 milligrams of 1-chloro-4-(β-D-glucopyranos-1-yl)-2-[4-((S)-tetrahydrofuran-3-yloxy)-benzyl]-benzene and 1000 milligrams metformin hydrochloride;
(5) 10 milligrams of 1-chloro-4-(β-D-glucopyranos-1-yl)-2-[4-((S)-tetrahydrofuran-3-yloxy)-benzyl]-benzene and 750 milligrams metformin hydrochloride;

(6) 5 milligrams of 1-chloro-4-(β-D-glucopyranos-1-yl)-2-[4-((S)-tetrahydrofuran-3-yloxy)-benzyl]-benzene and 1000 milligrams metformin hydrochloride;

(7) 5 milligrams of 1-chloro-4-(β-D-glucopyranos-1-yl)-2-[4-((S)-tetrahydrofuran-3-yloxy)-benzyl]-benzene and 750 milligrams metformin hydrochloride.

Optionally, the pharmaceutical compositions, particularly solid preparations (e.g. oral solid dosage forms, such as e.g. tablets) according to the present invention may further comprise a color coat and/or a final coat.

(a) Metformin Part:

The first part in the present invention is a part (composition, particularly solid composition, e.g. a solid pharmaceutical composition for oral administration, e.g. tablet) comprising metformin (particularly metformin hydrochloride) in extended release form, particularly an extended release formulation of metformin.

In an embodiment, this first part is a metformin (e.g. 500 mg, 750 mg or 1000 mg metformin hydrochloride) extended release core.

Exemplary extended release formulations of metformin are disclosed in U.S. Pat. Nos. 6,340,475; 6,488,962; 6,635,280; 6,723,340; 7,780,987; 6,866,866; 6,495,162; 6,790,459; 6,866,866; 6,475,521; and 6,660,300; the disclosures of which are incorporated herein in their entireties.

A particular extended release formulation of metformin is described in U.S. Pat. No. 6,723,340, the disclosure of which is incorporated herein in its entirety.

In an embodiment, the fixed-dose combination products of the present invention comprise—as first part—an inner core matrix formulation with metformin hydrochloride dispersed therein, said matrix formulation containing an extended release material. The matrix formulation is compressed into a tablet form.

In a particular embodiment, the fixed-dose combination products of the present invention comprise—as first part—an inner core extended release formulation comprising metformin hydrochloride, hydroxypropyl methylcellulose (hypromellose), polyethylene oxide, microcrystalline cellulose, and magnesium stearate.

In another particular embodiment, the fixed-dose combination products of the present invention comprise—as first part—an inner core extended release formulation comprising metformin hydrochloride, polyethylene oxide, low molecular weight hydroxypropyl methylcellulose (hypromellose, e.g. Methocel E5), and magnesium stearate.

A particular extended release formulation of metformin is described in U.S. Pat. No. 6,723,340 as follows:

In an embodiment, the extended release material of the matrix comprises poly(ethylene oxide) and/or hydroxypropyl methylcellulose (HPMC), preferably a combination of poly(ethylene oxide) and hydroxypropyl methylcellulose (HPMC), preferably at a weight ratio that causes the matrix to swell upon contact with gastric fluid to a size large enough to provide gastric retention.

The poly(ethylene oxide) component of the matrix may limit initial release of the drug and may impart gastric retention through swelling. The hydroxypropyl methylcellulose (HPMC) component may lower the amount of poly(ethylene oxide) required while still allowing the swelling to occur.

Preferably, the poly(ethylene oxide) has a viscosity average molecular weight of from about 2,000,000 to about 10,000,000 daltons, more preferably from about 4,000,000 to about 7,000,000 daltons.

Preferably, the hydroxypropyl methylcellulose (HPMC) has a viscosity of from about 4,000 centipoise to about 200,000 centipoise, more preferably from about 50,000 to about 200,000 centipoise, even more preferably 80,000 centipoise to about 120,000 centipoise, measured as a 2% solution in water.

More preferably, the poly(ethylene oxide) has a viscosity average molecular weight of from about 4,000,000 to about 7,000,000 daltons, and the hydroxypropyl methylcellulose (HPMC) has a viscosity of from about 80,000 centipoise to about 120,000 centipoise, measured as a 2% solution in water.

In an embodiment, the weight ratio of the poly(ethylene oxide) to hydroxypropyl methylcellulose (HPMC) is within the range from about 1:3 to 3:1, preferably 1:2 to 2:1.

In a further embodiment, the weight ratio of the poly(ethylene oxide) and hydroxypropyl methylcellulose (HPMC) in combination constitutes from about 15% to about 90%, or from about 30% to about 65%, or from about 40% to about 50%, by weight of the metformin part.

Tablet cores in accordance with this invention can be prepared by common tabletting methods that involve mixing, comminution, and fabrication steps commonly practiced by and well known to those skilled in the art of manufacturing drug formulations. Examples of such techniques are:

(1) Direct compression using appropriate punches and dies, typically fitted to a suitable rotary tabletting press;
(2) Injection or compression molding;
(3) Granulation by fluid bed, by low or high shear granulation, or by roller compaction, followed by compression; and
(4) Extrusion of a paste into a mold or to an extrudate to be cut into lengths.

When tablets are made by direct compression, the addition of lubricants may be helpful and is sometimes important to promote powder flow and to prevent breaking of the tablet when the pressure is relieved. Examples of typical lubricants are magnesium stearate (in a concentration of from 0.25% to 3% by weight, preferably about 1% or less by weight, in the powder mix), stearic acid (0.5% to 3% by weight), and hydrogenated vegetable oil (preferably hydrogenated and refined triglycerides of stearic and palmitic acids at about 1% to 5% by weight, most preferably about 2% by weight).

Additional excipients may be added, such as e.g. granulating aids (e.g. low molecular weight HPMC at 2-5% by weight), binders (e.g. microcrystalline cellulose), and additives to enhance powder flowability, tablet hardness, and tablet friability and to reduce adherence to the die wall.

An exemplary extended release metformin tablet core comprises metformin hydrochloride, a combination of poly(ethylene oxide) and hydroxypropyl methylcellulose (e.g. Methocel K100M) as a matrix for a swellable extended release tablet, microcrystalline cellulose as binder, low molecular weight hydroxypropyl methylcellulose (e.g. Methocel E5) as granulating aid, and magnesium stearate as lubricant.

The composition of a representative metformin core tablet is provided as follows:

metformin hydrochloride, e.g. 49.97% by weight of the first part,
poly(ethylene oxide), e.g. 26.50% by weight of the first part,
hydroxypropyl methylcellulose (e.g. Methocel K100M), e.g. 16.08% by weight of the first part,
microcrystalline cellulose, e.g. 4.99% by weight of the first part,
low molecular weight hydroxypropyl methylcellulose (e.g. Methocel E5), e.g. 1.70% by weight of the first part, and
magnesium stearate, e.g. 0.75% by weight of the first part.

Tablets may be formulated by dry blending a granulation comprising metformin hydrochloride and low molecular weight HPMC (e.g. Methocel E5) and the remaining excipients listed above, followed by pressing on a tablet press.

Such an extended release matrix formulation of metformin is disclosed in U.S. Pat. No. 6,723,340 (e.g. Example 3), the disclosure of which is incorporated herein in its entirety.

As further example of a lubricant sodium stearyl fumarate may be mentioned (e.g. at about 0.25-3% by weight).

Another particular extended release formulation of metformin comprises metformin hydrochloride (e.g. 750 mg or 1000 mg), poly(ethylene oxide) (e.g. SENTRY™ POLYOX™ WSR 303) as swelling and/or extended release polymer, low molecular weight hydroxypropyl methylcellulose (hypromellose, e.g. Methocel E5) as binder, and magnesium stearate as lubricant.

In a certain embodiment, the poly(ethylene oxide) as swelling and/or extended release polymer has an approximate molecular weight of 7,000,000, and/or a viscosity range 7500-10,000 centipoise measured as aqueous 1% solution at 25° C.

In a preferred embodiment, the poly(ethylene oxide) is SENTRY™ POLYOX™ WSR 303.

In a certain embodiment, the low molecular weight hydroxypropyl methylcellulose as (granulation) binder is hypromellose having viscosity of 5 centipoise measured as aqueous 2% solution at 20° C.

In a preferred embodiment, the low molecular weight hydroxypropyl methylcellulose is Methocel E5.

The composition of a representative metformin extended release core is provided as follows:

metformin hydrochloride, e.g. 750.0 mg, 65.68% by weight of the first part, poly(ethylene oxide) (SENTRY™ POLYOX™ WSR 303), e.g. 355.2 mg, 31.10% by weight of the first part, low molecular weight hydroxypropyl methylcellulose (Methocel E5), e.g. 25.5 mg, 2.23% by weight of the first part, and magnesium stearate, e.g. 11.3 mg, 0.99% by weight of the first part.

The composition of another representative metformin extended release core is provided as follows:

metformin hydrochloride, e.g. 1000.0 mg, 70.47% by weight of the first part, poly(ethylene oxide) (SENTRY™ POLYOX™ WSR 303), e.g. 370.0 mg, 26.07% by weight of the first part, low molecular weight hydroxypropyl methylcellulose (Methocel E5), e.g. 34.0 mg, 2.40% by weight of the first part, and magnesium stearate, e.g. 15.0 mg, 1.06% by weight of the first part.

The manufacturing of metformin (e.g. 750 mg or 1000 mg metformin hydrochloride) extended release cores comprises metformin wet granulation (e.g. high shear granulation) in the presence of low molecular weight HPMC (hypromellose, Methocel E5) as binder for granulation, followed by optional wet milling, drying (e.g. fluid bed drying, e.g. <0.2% LOD) and milling (e.g. dry granulation milling). The milled granulation is subsequently used for blending with poly(ethylene oxide) (SENTRY™ POLYOX™ WSR 303), then magnesium stearate as lubricant for tableting is added for final blending. The obtained metformin blend is used for compression of single layer tablets.

In the metformin granulation process the metformin hydrochloride (750 mg or 1000 mg, 96.71% by weight of total dry granulate) and part of hypromellose (Methocel E5, 2.39% by weight of total dry granulate) are premixed and granulated with an aqueous (10% w/w) binder solution of remaining part of hypromellose (Methocel E5, 0.90% by weight of total dry granulate) using a high shear granulator.

Before being used in the manufacturing process, the excipients during dispensing may be pre-sieved and the metformin HCl may be pre-milled.

In a further embodiment, the metformin extended release formulation allows for targeted, controlled delivery of metformin to the upper gastrointestinal (GI) tract. In a further embodiment, the metformin extended release formulation is a hydrogel matrix system and contains a swelling hydrophilic polymer and further excipients, which may allow the metformin tablet core to be retained in the stomach ('gastric retention') for approximately eight to nine hours. During this time, the tablet core's metformin is steadily delivered to the upper GI tract at the desired rate and time, without potentially irritating 'burst' of drug. This gradual, extended release typically allows for more of the metformin drug to be absorbed in the upper GI tract and minimizes the amount of drug that passes through to the lower GI tract.

In another embodiment, the metformin XR (e.g. 750 mg or 1000 mg) cores of this invention provide gastric retention with extended dose of metformin released over approximately 12 hours.

(b1) Linagliptin Part:

In one variant, the second part in the present invention is a part (composition, particularly film coat) comprising linagliptin in immediate release form.

In an embodiment, the fixed-dose combination products of the present invention comprise—as second part—a film coat formulation of linagliptin, said film coat formulation comprising linagliptin, a stabilizer for stabilizing linagliptin (e.g. a basic and/or nucleophilic excipient, preferably L-arginine as stabilizer), a film-coating agent (such as e.g. hydroxypropyl methylcellulose, e.g. Hypromellose 2910, Methocel E5, or Methocel E15), a plasticizer (such as e.g. polyethylene glycol, e.g. Macrogol 400, 6000 or 8000, or propylene glycol), and, optionally, a glidant (such as e.g. talc).

In an embodiment, the weight ratio of the L-arginine to linagliptin is within the range from about 20:1 to about 1:10, or from about 15:1 to about 1:10, or from about 10:1 to about 1:10, or from about 5:1 to about 1:5, or from about 4:1 to about 1:1, or from about 3:1 to about 1:1, or from about 4:1 to about 2:1, especially about 4:1.

In a further embodiment, the weight ratio of the L-arginine to linagliptin is within the range from about 2:1 to about 1:1, up to about 0.2:1.

In a preferred embodiment, the weight ratio of the L-arginine to linagliptin is within the range from about 4:1 to about 2:1, especially about 4:1.

For example, the composition of a representative linagliptin containing film coat is provided as follows:
linagliptin, e.g. 2.5 mg or 5 mg;
L-arginine, e.g. depending from need of stabilizer amount, e.g. in the range from about 0.5 mg to about 10 mg-12.5 mg (e.g. 5 mg or 10 mg), or up to about 20 mg-25 mg (e.g. 20 mg);
hydroxypropyl methylcellulose (e.g. Methocel E5, Methocel E15, or Pharmacoat 603 or 606), e.g. from about 25 mg to about 40 mg (especially from 34.5 mg to 38 mg, or 34.5 mg or 38 mg);
polyethylene glycol (e.g. Macrogol 400, 6000 or 8000), e.g. from about 0 to about 12 mg, especially 10-12 mg;
propylene glycol, e.g. from about 0 mg to about 15 mg (especially 9 mg or 0 mg); and talc, e.g. from about 0 mg to about 15 mg (especially 9 mg).

Depending from need of stabilizer the amount of L-arginine may be in the range from 0.5 mg to 10 mg-12.5 mg, or up to about 20 mg-25 mg. With different dose and different arginine amount, the arginine amount may be substituted by hydroxypropyl methylcellulose (HPMC).

In an embodiment, polyethylene glycol and propylene glycol are mutually exclusive in above composition, i.e. if polyethylene glycol is present then propylene glycol is absent, or if propylene glycol is present then polyethylene glycol is absent.

The composition of a representative linagliptin containing film coat suspension further comprises water, e.g. from about 240 mg to about 1440 mg, especially in the range from 904 mg to 1440 mg. The total solids concentration of the suspension is from about 4% to about 12.5% w/w, especially from 4% to 6% w/w. Viscosity may be from about 10 mPas to 110 mPas (e.g. 46-56 mPas).

The sum solids of the linagliptin coating suspension is from about 50 mg to about 120 mg. For example, the sum solids is 60 mg of solid amount of the film coating suspension for 2.5 mg linagliptin, and 120 mg sum solid amount of the film coating suspension for 5 mg linagliptin. Therefore with the same formulation of linagliptin and double coating time (i.e. double amount of coating suspension) it is possible to prepare the higher dose range of linagliptin. Hence different dosage strengths can be achieved by altering coating (spraying) times.

(b2) 1-Chloro-4-(β-D-glucopyranos-1-yl)-2-[4-((S)-tetrahydrofuran-3-yloxy)-benzyl]-benzene part:

In another variant, the second part in the present invention is a part (composition, particularly film coat) comprising 1-chloro-4-(β-D-glucopyranos-1-yl)-2-[4-((S)-tetrahydrofuran-3-yloxy)-benzyl]-benzene in immediate release form.

In an embodiment, the fixed-dose combination products of the present invention comprise—as second part—a film coat formulation of 1-chloro-4-(β-D-glucopyranos-1-yl)-2-[4-((S)-tetrahydrofuran-3-yloxy)-benzyl]-benzene, said film coat formulation comprising 1-chloro-4-(β-D-glucopyranos-1-yl)-2-[4-((S)-tetrahydrofuran-3-yloxy)-benzyl]-benzene, a film-coating agent (such as e.g. hydroxypropyl methylcellulose, e.g. Hypromellose 2910, Methocel E5, or Methocel E15), a plasticizer (such as e.g. polyethylene glycol, e.g. Macrogol 400, 6000 or 8000, or propylene glycol), and, optionally, a glidant (such as e.g. talc).

For example, the composition of a representative 1-chloro-4-(β-D-glucopyranos-1-yl)-2-[4-((S)-tetrahydrofuran-3-yloxy)-benzyl]-benzene containing film coat is provided as follows:

- 1-chloro-4-(β-D-glucopyranos-1-yl)-2-[4-((S)-tetrahydrofuran-3-yloxy)-benzyl]-benzene, e.g. 5 mg, 10 mg, 12.5 mg or 25 mg;
- optionally, L-arginine, e.g. from about 5 mg to about 25 mg;
- hydroxypropyl methylcellulose (e.g. Methocel E5, Methocel E15, or Pharmacoat 603 or 606), e.g. from about 25 mg to about 40 mg (especially from 34.5 mg to 38 mg, or 34.5 mg);
- polyethylene glycol (e.g. Macrogol 400, 6000 or 8000), e.g. from about 0 to about 12 mg;
- propylene glycol, e.g. from about 0 mg to about 15 mg (especially 9 mg); and
- talc, e.g. from about 0 mg to about 15 mg (especially 9 mg).

With different dose and different arginine amount, the arginine amount may be substituted by hydroxypropyl methylcellulose (HPMC).

In an embodiment, polyethylene glycol and propylene glycol are mutually exclusive in above composition, i.e. if polyethylene glycol is present then propylene glycol is absent, or if propylene glycol is present then polyethylene glycol is absent.

The composition of a representative 1-chloro-4-(β-D-glucopyranos-1-yl)-2-[4-((S)-tetrahydrofuran-3-yloxy)-benzyl]-benzene containing film coat suspension further comprises water, e.g. from about 240 mg to about 1440 mg, especially in the range from 904 mg to 1440 mg. The total solids concentration of the suspension is from about 4% to about 12.5% w/w, especially from 4% to 6% w/w.

The sum solids of the 1-chloro-4-(β-D-glucopyranos-1-yl)-2-[4-((S)-tetrahydrofuran-3-yloxy)-benzyl]-benzene coating suspension is from about 50 mg to about 120 mg. For example, the sum solids is 60 mg of solid amount of the film coating suspension for 12.5 mg 1-chloro-4-(R-D-glucopyranos-1-yl)-2-[4-((S)-tetrahydrofuran-3-yloxy)-benzyl]-benzene, and 120 mg sum solid amount of the film coating suspension for 25 mg 1-chloro-4-(β-D-glucopyranos-1-yl)-2-[4-((S)-tetrahydrofuran-3-yloxy)-benzyl]-benzene. Therefore with the same formulation of 1-chloro-4-(β-D-glucopyranos-1-yl)-2-[4-((S)-tetrahydrofuran-3-yloxy)-benzyl]-benzene and double coating time (i.e. double amount of coating suspension) it is possible to prepare the higher dose range of 1-chloro-4-(β-D-glucopyranos-1-yl)-2-[4-((S)-tetrahydrofuran-3-yloxy)-benzyl]-benzene. Hence different dosage strengths can be achieved by altering coating (spraying) times.

Further embodiments as to (b1) and/or (b2):

L-Arginine is preferably necessary for the stabilization of linagliptin. Alternatively or additionally, a seal coat and/or a barrier coat may be used between the metformin XR core and the linagliptin-containing film coat.

In an embodiment, a seal and/or a barrier coat is present between the metformin XR core and the linagliptin-containing film coat (preferably further containing L-arginine). In another embodiment, the seal and/or barrier coat is absent between the metformin XR core and the linagliptin-containing film coat (preferably further containing L-arginine).

In some embodiments, the barrier coat may be from 0% to 20% w/w or from 1% to 20% w/w or from 3% to 7% w/w (e.g. 0%, 6%, 12% or 18%) per weight of the total linagliptin/metformin HCl containing composition. Preferably, the barrier coat may have a weight in the range from 50 to 100 mg, for example 60-75 mg (such as for the formulation containing 2.5 mg/750 mg linagliptin/metformin HCl) or 75-95 mg (such as for the formulation containing 2.5 mg/1000 mg or 5 mg/1000 mg linagliptin/metformin HCl).

In a further embodiment, a seal coat and/or a barrier coat is/are present between the metformin XR core and the linagliptin-containing film coat (preferably further containing L-arginine).

In a preferred embodiment, a barrier coat is present between the metformin XR core and the linagliptin-containing film coat (preferably further containing L-arginine).

For Compound "A" preferably no arginine is necessary. For Compound "A" the seal and/or barrier coating of metformin XR cores may be optional. In one embodiment, a seal and/or barrier coat is present between the metformin XR core and the Compound "A" containing film coat. In another embodiment, the seal and/or barrier coat is absent between the metformin XR core and the Compound "A" containing film coat.

In a further embodiment, a seal coat and/or a barrier coat is/are present between the metformin XR core and the Compound "A" containing film coat.

Alternatively or further to the API film coats of (b1) and/or (b2), for the API (linagliptin or Compound "A") containing film coat, a film coat comprising a mixture of hydroxypropylcellulose and hydroxypropyl methylcellulose, or a mixture of polyvinyl alcohol (PVA) and polyethylene glycol (PEG); or a commercial film-coat such as Opadry®, Opadry II® or other Opadry IR film coat, which are formulated powder blends provided by Colorcon, may be used. With Opadry II or PVA based API coating higher solid concentrations and shorter coating time durations are possible, therefore it works in a range of 10-30%, especially 20% solid concentration. This higher solid concentration, e.g. 20%, typically results in a shorter coating time, e.g. 2-5 hours.

In further embodiments of the API containing film coating layers of this invention, the film-coating agent may be one or more of hydroxypropyl methylcellulose (HPMC, hypromellose such as e.g. hypromellose 2910 with nominal viscosity of 3, 5, 6, 15 and/or 50 cP, Methocel E5, Methocel E15, Pharmacoat 603, Pharmacoat 606, and/or Pharmacoat 615), polyvinyl alcohol (PVA), ethyl cellulose, hydroxypropyl cellulose, polydextrose, methacrylic and/or acrylic polymer, or mixtures thereof (e.g. a mixture of one or more HPMC and polydextrose).

In further embodiments of the API containing film coating layers of this invention, the plasticizer may be one or more of polyethylene glycol (PEG, such as e.g. Macrogol 400, 3000, 4000, 6000 and/or 8000), propylene glycol, diethyl phthalate, tributyl sebacate and/or triacetin, or mixtures thereof (e.g. a mixture of polyethylene glycol and triacetin).

In a further embodiment of this invention, a API containing film coat according to this invention may comprise or consist essentially of the API, preferably a stabilizer for stabilizing linagliptin (preferably L-arginine), one or more film-coating agents, e.g. selected from hydroxypropyl methylcellulose (HPMC, hypromellose such as e.g. hypromellose 2910 with nominal viscosity of 3, 5, 6, 15 and/or 50 cP, Methocel E5, Methocel E15, Pharmacoat 603, Pharmacoat 606, and/or Pharmacoat 615), polyvinyl alcohol (PVA), ethyl cellulose, hydroxypropyl cellulose, polydextrose, methacrylic and/or acrylic polymer, or a mixture thereof, optionally one or more plasticizers, e.g. selected from polyethylene glycol (PEG, such as e.g. Macrogol 400, 3000, 4000, 6000 and/or 8000), propylene glycol, diethyl phthalate, tributyl sebacate and/or triacetin, or a mixture thereof, optionally a glidant, e.g. talc, magnesium stearate or fumed silica, and optionally one or more pigments (e.g. titanium dioxide) and/or colors (e.g. based on iron oxides).

Accordingly, the API containing film coating layers according to this invention may comprise one or more of the following excipients:

at least one film-coating agent, such as e.g. hydroxypropyl methylcellulose (HPMC, hypromellose such as e.g. hypromellose 2910 with nominal viscosity of 3, 5, 6, 15 or 50 cP, Methocel E5, Methocel E15, Pharmacoat 603, Pharmacoat 606, or Pharmacoat 615), polyvinyl alcohol (PVA), ethyl cellulose, hydroxypropyl cellulose, polydextrose, or a methacrylic or acrylic polymer, at least one plasticizer, such as e.g. polyethylene glycol (PEG, such as e.g. Macrogol 400, 3000, 4000, 6000 or 8000), propylene glycol, diethyl phthalate, tributyl sebacate or triacetin, at least one glidant or anti-adherent, such as e.g. talc, magnesium stearate or fumed silica, and at least one pigment, such as e.g. titanium dioxide, and/or colorant (such as e.g. based on an iron oxide).

In certain embodiments, the hydroxypropyl methylcellulose (HPMC) as film-coating agent is hypromellose having viscosity from about 3 centipoise to about 15 centipoise or up to 40-60 centipoise, measured as aqueous 2% solution at 20° C., e.g. 3, 5, 6, 15 or 50 cP, such as e.g. hypromellose 2910 with nominal viscosity of 3 cP (HPMC 2910-3), hypromellose 2910 with nominal viscosity of 5 cP (HPMC 2910-5), hypromellose 2910 with nominal viscosity of 6 cP (HPMC 2910-6), hypromellose 2910 with nominal viscosity of 15 cP (HPMC 2910-15), hypromellose 2910 with nominal viscosity of 50 cP (HPMC 2910-50), Methocel E5, Methocel E15, Pharmacoat 603, Pharmacoat 606, or Pharmacoat 615.

In certain embodiments, the polyethylene glycol (PEG) as plasticizer is macrogol having average molecular weight from about 400 to about 8000 daltons, e.g. 400, 1500, 3000, 4000, 6000 or 8000 D, such as e.g. Marcrogol 400, Marcrogol 6000 or Marcrogol 8000.

In certain embodiments, the coating material for API coating is commercially available under the trade name Opadry®, Opadry II® or other Opadry® film coat.

For example, the composition of a representative linagliptin containing film coat may be provided as follows:
linagliptin, such as e.g. from 0.5 mg to 10 mg (e.g. 2.5 mg or 5 mg);
L-arginine, e.g. depending from need of stabilizer amount, e.g. the weight ratio L-arginine:linagliptin may be 1:1 to 5:1, such as e.g. in the range from about 0.5 mg to about 10 mg-12.5 mg (e.g. 5 mg or 10 mg) or up to about 20 mg-25 mg (e.g. 20 mg);
hydroxypropyl methylcellulose (e.g. Methocel E5, Methocel E15, or Pharmacoat 603 or 606), e.g. from about 25 mg to about 40 mg (especially from 34.5 mg to 38 mg, or 34.5 mg or 38 mg);
polyethylene glycol (e.g. Macrogol 400, 6000 or 8000), e.g. from about 0 to about 15 mg, especially 10-12 mg;
propylene glycol, e.g. from about 0 mg to about 15 mg (especially 9 mg or 0 mg); and
talc, e.g. from about 0 mg to about 15 mg (especially 9 mg).

For example, an API (linagliptin) containing film coat according to this invention may comprise or consist essentially of
linagliptin, such as e.g. from 0.5 mg to 10 mg (e.g. 2.5 mg or 5 mg),
L-arginine (as stabilizer, e.g. the weight ratio L-arginine:linagliptin may be 1:1 to 5:1, such as e.g. in the range from about 0.5 mg to about 25 mg, preferably from about 5 mg to about 20 mg, more preferably from about 10 mg to about 20 mg),
a film forming agent (e.g. based on HPMC (HPMC 2910-3), e.g. in the range from about 25 mg to about 40 mg, such as a mixture of hypromellose 2910 (HPMC 2910-3, 95% w/w) and PEG (PEG 8000, 5% w/w)),
a plasticizer (e.g. based on PEG (PEG 6000), e.g. in the range from about 1 mg to about 12 mg, especially from about 10 mg to about 12 mg, and
a glidant (e.g. talc, e.g. in the range from about 1 mg to about 15 mg, especially about 9 mg).

For particular example, an immediate release API coating of this invention comprises or consist essentially of:
polyethylene glycol (e.g. polyethylene glycol of molecular weight of about 6000 and/or 8000, e.g. 8-25% w/w, preferably 10-20% w/w, such as 16.8 or 14.3% w/w),
linagliptin (as API, e.g. 1-10% w/w, preferably 2-7% w/w, such as 3.5 or 6.0% w/w),
L-arginine (as stabilizer, e.g. the weight ratio L-arginine:linagliptin may be 1:1 to 5:1, preferably 2:1 to 4:1, especially 4:1; such as e.g. 4-40% w/w, preferably 10-30% w/w, such as 14 or 24% w/w), hydroxypropyl methylcellulose (e.g. hydroxypropyl methylcellulose of 3 cP, e.g. 40-70% w/w, preferably 40-65% w/w, such as 53.2 or 45.2% w/w), and talc (e.g. 5-20% w/w, preferably 8-16% w/w, such as 12.5 or 10.7% w/w), wherein % w/w relate to the weight of the immediate release coating.

For more particular example, an immediate release API coating of this invention comprises:

polyethylene glycol of molecular weight of about 6000 (e.g. 8-20% w/w, preferably 10-18 w/w, such as 14.0 or 11.9% w/w), linagliptin (as API, e.g. 1-10% w/w, preferably 2-7% w/w, such as 3.5 or 6.0% w/w), L-arginine (as stabilizer, e.g. the weight ratio L-arginine: linagliptin may be 1:1 to 5:1, preferably 2:1 to 4:1, especially 4:1; such as e.g. 4-40% w/w, preferably 10-30% w/w, such as 14 or 24% w/w), hydroxypropyl methylcellulose (e.g. hydroxypropyl methylcellulose of 3 cP, e.g. 40-70% w/w, preferably 40-65% w/w, such as 53.2 or 45.2% w/w), polyethylene glycol of molecular weight of about 8000 (e.g. 0-5% w/w, preferably 2-4% w/w, such as 2.8 or 2.4% w/w), and talc (e.g. 5-20% w/w, preferably 8-16% w/w, such as 12.5 or 10.7% w/w), wherein % w/w relate to the weight of the immediate release coating, and wherein the content of linagliptin may be in the range from 1 to 10 mg, particularly 2.5 mg or 5.0 mg.

For further example, further versions of API-containing film coat compositions comprising one or more of the following ingredients of Tables 1 or 2, or of Tables 3, 4a, 4b, 4c, or of Tables 5, 6a, 6b, 6c may be provided, e.g. as follows from Tables 1 or 2, or, from Tables 3, 4a, 4b, 4c, or from Tables 5, 6a, 6b, 6c:

In one embodiment of the API coatings of this invention, the film-coating agent used is highly viscous.

In another embodiment of the API coatings of this invention, the film-coating agent used is low viscous.

TABLE 2

Further Example (prototypical) formulations for API-coating of linagliptin on top of metformin XR cores:

| Composition (% w/w) | PEG-containing version (e.g. 2.5 mg API) | PEG-containing version (reduced arginine) (e.g. 5 mg API) | PG-containing version (low DL) (e.g. 2.5 mg API) | PG-containing version (high DL) (e.g. 2.5 mg API) |
|---|---|---|---|---|
| Linagliptin | 4.20 | 4.39 | 4.55 | 5.29 |
| HPMC (e.g. Pharmacoat 615) | 67.23 | 70.18 | 72.73 | 70.55 |
| Polyethylene glycol (e.g. PEG 6000) | 20.17 | 21.05 | — | — |
| Propylene glycol | — | — | 3.64 | 3.53 |
| L-Arginine | 8.40 | 4.39 | 9.09 | 10.58 |
| Talc | — | — | 10.00 | 10.05 |
| Purified water | ** | ** | ** | ** |
| Total | 100.00 | 100.00 | 100.00 | 100.00 |
| Solid content of suspension (%) | 5.95 | 5.70 | 5.50 | 5.67 |

** Solvent is a volatile component, which does not remain in the final product

TABLE 1

Example (prototypical) formulations for API-coating of linagliptin on top of metformin XR cores

| Composition (% w/w) | PEG-containing version (e.g. 2.5 mg API) | PEG-containing version (reduced arginine) (e.g. 5 mg API) | PG-containing version (low DL) (e.g. 2.5 mg API) | PG-containing version (high DL) (e.g. 2.5 mg API) | Further version (e.g. 2.5 mg API) | Further version (e.g. 5 mg API) |
|---|---|---|---|---|---|---|
| Linagliptin | 4.20 | 4.39 | 4.55 | 5.29 | 4.16 | 4.16 |
| HPMC (e.g Pharmacoat 615)* | 67.23 | 70.18 | 72.73 | 70.55 | — | — |
| HPMC (e.g Methocel E5) | — | — | — | — | 57.5 | 57.5 |
| Polyethylene glycol (e.g. PEG 6000) | 20.17 | 21.05 | — | — | 15 | 15 |
| Propylene glycol | — | — | 3.64 | 3.53 | — | — |
| L-Arginine | 8.40 | 4.39 | 9.09 | 10.58 | 8.33 | 8.33 |
| Talc | — | — | 10.00 | 10.05 | 15 | 15 |
| Purified water | ** | ** | ** | ** | ** | ** |
| Total | 100.00 | 100.00 | 100.00 | 100.00 | 100.00 | 100.00 |
| Solid content of suspension (%) | 5.95 | 5.70 | 5.50 | 5.67 | 4.0 | 4.0 |

*Alternative Methocel E15
** Solvent is a volatile component, which does not remain in the final product

TABLE 3

Example formulations for API-coating of Compound "A" on top of metformin XR cores and an optional seal or barrier coating layer:

| Composition (% w/w) | Ex. 3.1 (e.g. 5 mg API) | Ex. 3.2 (e.g. 10 mg API) | Ex. 3.3 (e.g. 12.5 mg API) | Ex. 3.4 (e.g. 25 mg API) |
|---|---|---|---|---|
| Polyethylene glycol (e.g. PEG 6000) | 15.6 | 14.5 | 14.0 | 11.9 |
| Compound "A" | 7.8 | 14.5 | 17.5 | 29.8 |
| Hydroxypropyl methylcellulose (e.g. 3 cP) (e.g. HPMC 2910/Hypromellose) | 59.4 | 55.1 | 53.1 | 45.2 |
| Polyethylene glycol (e.g. PEG 8000) | 3.1 | 2.9 | 2.8 | 2.4 |
| Talc | 14.1 | 13.0 | 12.6 | 10.7 |
| Purified water | ** | ** | ** | ** |
| Total | 100.0 | 100.0 | 100.0 | 100.0 |
| Solid content of suspension (%) | 6.4 | 6.4 | 6.4 | 6.4 |

** Solvent is a volatile component, which does not remain in the final product

In the examples according to the Table 3 the parts hydroxypropylmethylcellulose and polyethylene glycol (e.g. PEG 8000) may be employed as a film coating system.

TABLE 4a

Further Example formulations for extended release core comprising metformin hydrochloride, barrier coating and API-coating of Compound "A":

| Composition (% w/w) | Ex. 4.1 (e.g. 750 mg Metformin hydrochloride, 5 mg API) | Ex. 4.2 (e.g. 750 mg Metformin hydrochloride, 10 mg API) | Ex. 4.3 (e.g. 750 mg Metformin hydrochloride, 12.5 mg API) | Ex. 4.4 (e.g. 750 mg Metformin hydrochloride, 25 mg API) |
|---|---|---|---|---|
| Extended release core | | | | |
| Metformin hydrochloride | 65.7 | 65.7 | 65.7 | 65.7 |
| Hydroxypropyl methylcellulose (e.g. viscosity about 5 mPas for a 2% solution in water at 20° C., such as Methocel E5) | 2.2 | 2.2 | 2.2 | 2.2 |
| Polyethylene oxide (e.g. high molecular weight, e.g. about 7,000,000, such as WSR-303 NF TG LEO) | 31.1 | 31.1 | 31.1 | 31.1 |
| Magnesium stearate | 1.0 | 1.0 | 1.0 | 1.0 |
| Total | 100.0 | 100.0 | 100.0 | 100.0 |
| Barrier coating | | | | |
| Titanium dioxide | 32.4 | 32.4 | 32.4 | 32.4 |
| Polydextrose | 25.9 | 25.9 | 25.9 | 25.9 |
| Hydroxypropyl methylcellulose (e.g. 3 cP) | 19.5 | 19.5 | 19.5 | 19.5 |
| Hydroxypropyl methylcellulose (e.g. 6 cP) | 16.7 | 16.7 | 16.7 | 16.7 |
| Hydroxypropyl methylcellulose (e.g. 50 cP) | 2.8 | 2.8 | 2.8 | 2.8 |
| Polyethylene glycol (e.g. PEG 8000) | 2.7 | 2.7 | 2.7 | 2.7 |
| Purified water | ** | ** | ** | ** |
| Total | 100.0 | 100.0 | 100.0 | 100.0 |
| Solid content of suspension (%) | 20.0 | 20.0 | 20.0 | 20.0 |
| API coating | | | | |
| Polyethylene glycol (e.g. PEG 6000) | 15.6 | 14.5 | 14.0 | 11.9 |
| Compound "A" as API | 7.8 | 14.5 | 17.5 | 29.8 |

TABLE 4a-continued

Further Example formulations for extended release core comprising metformin hydrochloride, barrier coating and API-coating of Compound "A":

| Composition (% w/w) | Ex. 4.1 (e.g. 750 mg Metformin hydrochloride, 5 mg API) | Ex. 4.2 (e.g. 750 mg Metformin hydrochloride, 10 mg API) | Ex. 4.3 (e.g. 750 mg Metformin hydrochloride, 12.5 mg API) | Ex. 4.4 (e.g. 750 mg Metformin hydrochloride, 25 mg API) |
|---|---|---|---|---|
| Hydroxypropyl methylcellulose (e.g. 3 cP) (e.g. HPMC 2910/Hypromellose) | 59.4 | 55.1 | 53.1 | 45.2 |
| Polyethylene glycol (e.g. PEG 8000) | 3.1 | 2.9 | 2.8 | 2.4 |
| Talc | 14.1 | 13.0 | 12.6 | 10.7 |
| Purified water | ** | ** | ** | ** |
| Total | 100.0 | 100.0 | 100.0 | 100.0 |
| Solid content of suspension (%) | 6.4 | 6.4 | 6.4 | 6.4 |

** Solvent is a volatile component, which does not remain in the final product

TABLE 4b

Further Example formulations for extended release core comprising metformin hydrochloride, barrier coating and API-coating of Compound "A":

| Composition (% w/w) | Ex. 4.5 (e.g. 1000 mg Metformin hydrochloride, e.g. 5 mg API) | Ex. 4.6 (e.g. 1000 mg Metformin hydrochloride, 10 mg API) | Ex. 4.7 (e.g. 1000 mg Metformin hydrochloride, 12.5 mg API) | Ex. 4.8 (e.g. 1000 mg Metformin hydrochloride, 25 mg API) |
|---|---|---|---|---|
| Extended release core | | | | |
| Metformin hydrochloride | 70.5 | 70.5 | 70.5 | 70.5 |
| Hydroxypropyl methylcellulose (e.g. viscosity about 5 mPas for a 2% solution in water at 20° C., such as Methocel E5) | 2.4 | 2.4 | 2.4 | 2.4 |
| Polyethylene glycol (e.g. high molecular weight, e.g. about 7,000,000, such as WSR-303 NF TG LEO) | 26.07 | 26.07 | 26.07 | 26.07 |
| Magnesium stearate | 1.0 | 1.0 | 1.0 | 1.0 |
| Total | 100.0 | 100.0 | 100.0 | 100.0 |
| Barrier coating | | | | |
| Titanium dioxide | 32.4 | 32.4 | 32.4 | 32.4 |
| Polydextrose | 25.9 | 25.9 | 25.9 | 25.9 |
| Hydroxypropyl methylcellulose (e.g. 3 cP) | 19.5 | 19.5 | 19.5 | 19.5 |
| Hydroxypropyl methylcellulose (e.g. 6 cP) | 16.7 | 16.7 | 16.7 | 16.7 |
| Hydroxypropyl methylcellulose (e.g. 50 cP) | 2.8 | 2.8 | 2.8 | 2.8 |
| Polyethylene glycol (e.g. PEG 8000) | 2.7 | 2.7 | 2.7 | 2.7 |
| Purified water | ** | ** | ** | ** |
| Total | 100.0 | 100.0 | 100.0 | 100.0 |
| Solid content of suspension (%) | 20.0 | 20.0 | 20.0 | 20.0 |

TABLE 4b-continued

Further Example formulations for extended release core comprising metformin hydrochloride, barrier coating and API-coating of Compound "A":

| Composition (% w/w) | Ex. 4.5 (e.g. 1000 mg Metformin hydrochloride, e.g. 5 mg API) | Ex. 4.6 (e.g. 1000 mg Metformin hydrochloride, 10 mg API) | Ex. 4.7 (e.g. 1000 mg Metformin hydrochloride, 12.5 mg API) | Ex. 4.8 (e.g. 1000 mg Metformin hydrochloride, 25 mg API) |
|---|---|---|---|---|
| API coating | | | | |
| Polyethylene glycol (e.g. PEG 6000) | 15.6 | 14.5 | 14.0 | 11.9 |
| Compound "A" as API | 7.8 | 14.5 | 17.5 | 29.8 |
| Hydroxypropyl methylcellulose (e.g. 3 cP) (e.g. HPMC 2910/Hypromellose) | 59.4 | 55.1 | 53.1 | 45.2 |
| Polyethylene glycol (e.g. PEG 8000) | 3.1 | 2.9 | 2.8 | 2.4 |
| Talc | 14.1 | 13.0 | 12.6 | 10.7 |
| Purified water | ** | ** | ** | ** |
| Total | 100.0 | 100.0 | 100.0 | 100.0 |
| Solid content of suspension (%) | 6.4 | 6.4 | 6.4 | 6.4 |

** Solvent is a volatile component, which does not remain in the final product

In the examples according to the Tables 4a and 4b the parts titanium dioxide, polydextrose, hydroxypropyl methylcellulose (e.g. 3 cP), hydroxypropyl methylcellulose (e.g. 6 cP), hydroxypropyl methylcellulose (e.g. 50 cP) and polyethylene glycol (e.g. PEG 8000) may be employed as a film coating system in the preparation of the barrier coating.

In addition the parts hydroxypropylmethylcellulose and polyethylene glycol (e.g. PEG 8000) may be employed as a further film coating system in the preparation of the API coating.

In the examples according to the Tables 4a and 4b the barrier coat (solid content) has a weight in the range from 50 to 100 mg, for example 60-75 mg in the examples of Table 4a and 75-95 mg in the examples of Table 4b.

Therefore according to a preferred embodiment of the present invention there is provided a pharmaceutical composition comprising
a) an extended release core comprising metformin (particularly metformin hydrochloride) and one or more excipients;
b) an optional seal and/or barrier coating, preferably barrier coating; and
c) an immediate release coating (API coating) comprising 10-25% w/w of polyethylene glycol,
5-35% w/w of 1-chloro-4-(β-D-glucopyranos-1-yl)-2-[4-((S)-tetrahydrofuran-3-yloxy)-benzyl]-benzene (as API),
40-70% w/w of hydroxypropyl methylcellulose,
5-20% w/w of talc,
wherein % w/w relate to the weight of the immediate release coating.

Preferably the pharmaceutical composition according to this embodiment additionally comprises one or more optional color and/or final coatings.

According to a more preferred embodiment of the present invention there is provided a pharmaceutical composition comprising
a) an extended release core comprising metformin (particularly metformin hydrochloride) and one or more excipients;
b) an optional seal and/or barrier coating, preferably barrier coating; and
c) an immediate release coating (API coating) comprising 8-20% w/w, preferably 10-18% w/w of polyethylene glycol of molecular weight of about 6000,
5-35% w/w of 1-chloro-4-(β-D-glucopyranos-1-yl)-2-[4-((S)-tetrahydrofuran-3-yloxy)-benzyl]-benzene (as API),
40-70% w/w, preferably 40-65% w/w of hydroxypropyl methylcellulose,
0-5% w/w, preferably 2-4% w/w of polyethylene glycol of molecular weight of about 8000,
5-20% w/w, preferably 8-16% w/w of talc,
wherein % w/w relate to the weight of the immediate release coating.

Preferably the pharmaceutical composition according to this embodiment additionally comprises one or more optional color and/or final coatings.

According to an even more preferred embodiment of the present invention there is provided a pharmaceutical composition comprising
a) an extended release core comprising metformin (particularly metformin hydrochloride) and one or more excipients;
b) an optional seal and/or barrier coating, preferably barrier coating; and
c) an immediate release coating (API coating) comprising 8-20% w/w, preferably 10-18% w/w of polyethylene glycol of molecular weight of about 6000,
5-35% w/w of 1-chloro-4-(β-D-glucopyranos-1-yl)-2-[4-((S)-tetrahydrofuran-3-yloxy)-benzyl]-benzene (as API),
40-70% w/w, preferably 40-65% w/w of hydroxypropyl methylcellulose,
0-5% w/w, preferably 2-4% w/w of polyethylene glycol of molecular weight of about 8000,
5-20% w/w, preferably 8-16% w/w of talc,
wherein % w/w relate to the weight of the immediate release coating, and
wherein the content of 1-chloro-4-(β-D-glucopyranos-1-yl)-2-[4-((S)-tetrahydrofuran-3-yloxy)-benzyl]-benzene is in the range from 5 to 25 mg, for example 5, 10, 12.5 or 25 mg.

Preferably the pharmaceutical composition according to this embodiment additionally comprises one or more optional color and/or final coatings.

According to a further more preferred embodiment of the present invention there is provided a pharmaceutical composition comprising
a) an extended release core comprising
60-75% w/w of metformin hydrochloride,
2-3% w/w of hydroxypropyl methylcellulose (e.g. viscosity about 5 mPas for a 2% solution in water at 20° C., such as Methocel E5),
23-35% w/w of polyethylene oxide (e.g. high molecular weight, e.g. about 7,000,000, such as WSR-303 NF TG LEO),
0.5-2% w/w magnesium stearate,
wherein % w/w relate to the weight of the extended release core, and
wherein the content of metformin hydrochloride is in the range from 500 to 1000 mg, for example 500, 750 or 1000 mg,
b) a barrier coating, e.g. comprising polydextrose, hydroxypropylmethylcelluloses (e.g. 3 to 50 cP) and polyethylene glycol (e.g. PEG 8000) and wherein the barrier coating has a weight for example in the range from 50 to 100 mg; and
c) an immediate release coating comprising
8-20% w/w, preferably 10-18% w/w of polyethylene glycol of molecular weight of about 6000,
5-35% w/w of 1-chloro-4-(β-D-glucopyranos-1-yl)-2-[4-((S)-tetrahydrofuran-3-yloxy)-benzyl]-benzene,
40-70% w/w, preferably 40-65% w/w of hydroxypropyl methylcellulose,
0-5% w/w, preferably 2-4% w/w of polyethylene glycol of molecular weight of about 8000,
5-20% w/w, preferably 8-16% w/w of talc,
wherein % w/w relate to the weight of the immediate release coating, and
wherein the content of 1-chloro-4-(β-D-glucopyranos-1-yl)-2-[4-((S)-tetrahydrofuran-3-yloxy)-benzyl]-benzene is in the range from 5 to 25 mg, for example 5, 10, 12.5 or 25 mg.

Preferably the pharmaceutical composition according to this embodiment additionally comprises one or more optional color and/or final coatings.

TABLE 5

Example formulations for API-coating of linagliptin on top of metformin XR cores and an optional seal or barrier coating layer:

| Composition (% w/w) | Ex. 5.1 (e.g. 2.5 mg API) | Ex. 5.2 (e.g. 5 mg API) |
|---|---|---|
| Polyethylene glycol (e.g. PEG 6000) | 14.0 | 11.9 |
| Linagliptin | 3.5 | 6.0 |
| L-Arginine | 14.0 | 23.8 |
| Hydroxypropyl methylcellulose (e.g. HPMC of 3 cP, such as HPMC-2910-3) | 53.2 | 45.2 |
| Polyethylene glycol (e.g. PEG 8000) | 2.8 | 2.4 |
| Talc | 12.5 | 10.7 |
| Purified water | * | * |
| Total | 100.0 | 100.0 |

* Processing agent water used in manufacturing and removed by drying

TABLE 6a

Further Example formulations for extended release core comprising metformin hydrochloride, barrier coating and API-coating of linagliptin

| Component | mg/tablet |
|---|---|
| Extended release core | |
| Metformin hydrochloride (Metformin HCl) | 750 |
| Polyethylene Oxide (e.g. high molecular weight, e.g. about 7,000,000, such as WSR-303) | 355.2 |
| Hydroxypropyl methylcellulose (Hypromellose) (e.g. viscosity about 5 mPas for a 2% solution in water at 20° C., such as HPMC 2910-5 (Methocel E5)) | 25.5 |
| Magnesium Stearate | 11.3 |
| Barrier coat: | |
| Film Forming System: | 68.2 |
| Hydroxypropyl methylcellulose (e.g. HPMCs of 3 cP, 6 cP and 50 cP, such as | |
| HPMC 2910-3 (e.g. 19.46% w/w), | |
| HPMC 2910-6 (e.g. 16.68% w/w) and | |
| HPMC 2910-50 (e.g. 2.79% w/w)), | |
| Polydextrose (e.g. 25.94% w/w), | |
| Polyethylene glycol (e.g. PEG 8000, e.g. 2.70% w/w), | |
| Titanium dioxide (e.g. 32.43% w/w), | |
| Purified water | —* |
| Active (API) coat: | |
| Linagliptin (as API) | 2.5 |
| Film Forming System: | 40.0 |
| Hydroxypropyl methylcellulose (e.g. HPMC of 3 cP, such as HPMC 2910-3, e.g. 95% w/w) | |
| Polyethylene glycol (e.g. PEG 8000, e.g. 5% w/w) | |
| L-Arginine | 10.0 |
| Polyethylene glycol (e.g. PEG 6000) | 10.0 |
| Talc | 9.0 |
| Purified water | —* |

*Processing agent water used in manufacturing and removed by drying

TABLE 6b

Further Example formulations for extended release core comprising metformin hydrochloride, barrier coating and API-coating of linagliptin

| Component | mg/tablet |
|---|---|
| Extended release core | |
| Metformin hydrochloride (Metformin HCl) | 1000 |
| Polyethylene Oxide (e.g. high molecular weight, e.g. about 7,000,000, such as WSR-303) | 370 |
| Hydroxypropyl methylcellulose (Hypromellose) (e.g. viscosity about 5 mPas for a 2% solution in water at 20° C., such as HPMC 2910-5 (Methocel E5)) | 34.0 |
| Magnesium Stearate | 15.0 |
| Barrier coat: | |
| Film Forming System: | 85.0 |
| Hydroxypropyl methylcellulose (e.g. HPMCs of 3 cP, 6 cP and 50 cP, such as | |
| HPMC 2910-3 (e.g. 19.46% w/w), | |
| HPMC 2910-6 (e.g. 16.68% w/w) and | |
| HPMC 2910-50 (e.g. 2.79% w/w)), | |
| Polydextrose (e.g. 25.94% w/w), | |
| Polyethylene glycol (e.g. PEG 8000, e.g. 2.70% w/w), | |
| Titanium dioxide (e.g. 32.43% w/w), | |
| Purified water | —* |
| Active (API) coat: | |
| Linagliptin (as API) | 2.5 |
| Film Forming System: | 40.0 |
| Hydroxypropyl methylcellulose (e.g. HPMC of 3 cP, such as HPMC 2910-3, e.g. 95% w/w) | |
| Polyethylene glycol (e.g. PEG 8000, e.g. 5% w/w) | |
| L-Arginine | 10.0 |

TABLE 6b-continued

Further Example formulations for extended release core comprising metformin hydrochloride, barrier coating and API-coating of linagliptin

| Component | mg/tablet |
|---|---|
| Polyethylene glycol (e.g. PEG 6000) | 10.0 |
| Talc | 9.0 |
| Purified water | —* |

*Processing agent water used in manufacturing and removed by drying

TABLE 6c

Further Example formulations for extended release core comprising metformin hydrochloride, barrier coating and API-coating of linagliptin

| Component | mg/tablet |
|---|---|
| Extended release core | |
| Metformin hydrochloride (Metformin HCl) | 1000 |
| Polyethylene Oxide | 370 |
| (e.g. high molecular weight, e.g. about 7,000,000, such as WSR-303) | |
| Hydroxypropyl methylcellulose (Hypromellose) | 34.0 |
| (e.g. viscosity about 5 mPas for a 2% solution in water at 20° C., such as HPMC 2910-5 (Methocel E5)) | |
| Magnesium Stearate | 15.0 |
| Barrier coat: | |
| Film Forming System: | 85.0 |
| Hydroxypropyl methylcellulose (e.g. HPMCs of 3 cP, 6 cP and 50 cP, such as | |
| HPMC 2910-3 (e.g. 19.46% w/w), | |
| HPMC 2910-6 (e.g. 16.68% w/w) and | |
| HPMC 2910-50 (e.g. 2.79% w/w)), | |
| Polydextrose (e.g. 25.94% w/w), | |
| Polyethylene glycol (e.g. PEG 8000, e.g. 2.70% w/w), | |
| Titanium dioxide (e.g. 32.43% w/w), | |
| Purified water | —* |
| Active (API) coat: | |
| Linagliptin (as API) | 5.0 |
| Film Forming System: | 40.0 |
| Hydroxypropyl methylcellulose (e.g. HPMC of 3 cP, such as HPMC 2910-3, e.g. 95% w/w) | |
| Polyethylene glycol (e.g. PEG 8000, e.g. 5% w/w) | |
| L-Arginine | 20.0 |
| Polyethylene glycol (e.g. PEG 6000) | 10.0 |
| Talc | 9.0 |
| Purified water | —* |

*Processing agent water used in manufacturing and removed by drying

In the examples according to the Tables 5, 6a, 6b and 6c, as to the barrier coating, the parts titanium dioxide, polydextrose, hydroxypropyl methylcellulose (e.g. 3 cP), hydroxypropyl methylcellulose (e.g. 6 cP), hydroxypropyl methylcellulose (e.g. 50 cP), polyethylene glycol (e.g. PEG 8000) may be employed together (such as e.g. as a film coating system) or separately in the preparation of the barrier coating.

In addition, as to the API coating, the parts hydroxypropyl methylcellulose (e.g. 3 cP) and polyethylene glycol (e.g. PEG 8000) may be employed together (such as e.g. as a film coating system) or separately in the preparation of the API coating.

In the examples according to the Tables 5, 6a, 6b, 6c the barrier coat (solid content) may have a weight in the range from 50 to 100 mg, for example 60-75 mg in the examples of Table 6a and 75-95 mg in the examples of Table 6b or 6c.

Therefore according to a preferred embodiment of the present invention there is provided a pharmaceutical composition comprising a) an extended release core comprising metformin (particularly metformin hydrochloride) and one or more excipients;

b) an optional seal and/or barrier coating, preferably barrier coating;

c) an immediate release coating (API coating) comprising polyethylene glycol (e.g. polyethylene glycol of molecular weight of about 6000 and/or 8000, e.g. 8-25% w/w, preferably 10-20% w/w, such as 16.8 or 14.3% w/w), linagliptin (as API, e.g. 1-10% w/w, preferably 2-7% w/w, such as 3.5 or 6.0% w/w), L-arginine (as stabilizer, e.g. the weight ratio L-arginine:linagliptin may be 1:1 to 5:1, preferably 2:1 to 4:1, especially 4:1; such as e.g. 4-40% w/w, preferably 10-30% w/w, such as 14 or 24% w/w), hydroxypropyl methylcellulose (e.g. hydroxypropyl methylcellulose of 3 cP, e.g. 40-70% w/w, preferably 40-65% w/w, such as 53.2 or 45.2% w/w), talc (e.g. 5-20% w/w, preferably 8-16% w/w, such as 12.5 or 10.7% w/w), wherein % w/w relate to the weight of the immediate release coating.

Preferably the pharmaceutical composition according to this embodiment additionally comprises one or more optional color and/or final coatings.

According to a more preferred embodiment of the present invention there is provided a pharmaceutical composition comprising a) an extended release core comprising metformin (particularly metformin hydrochloride) and one or more excipients;

b) an optional seal and/or barrier coating, preferably barrier coating;

c) an immediate release coating (API coating) comprising polyethylene glycol of molecular weight of about 6000 (e.g. 8-20% w/w, preferably 10-18 w/w, such as 14.0 or 11.9% w/w), linagliptin (as API, e.g. 1-10% w/w, preferably 2-7% w/w, such as 3.5 or 6.0% w/w), L-arginine (as stabilizer, e.g. the weight ratio L-arginine:linagliptin may be 1:1 to 5:1, preferably 2:1 to 4:1, especially 4:1; such as e.g. 4-40% w/w, preferably 10-30% w/w, such as 14 or 24% w/w), hydroxypropyl methylcellulose (e.g. hydroxypropyl methylcellulose of 3 cP, e.g. 40-70% w/w, preferably 40-65% w/w, such as 53.2 or 45.2% w/w), polyethylene glycol of molecular weight of about 8000 (e.g. 0-5% w/w, preferably 2-4% w/w, such as 2.8 or 2.4% w/w), talc (e.g. 5-20% w/w, preferably 8-16% w/w, such as 12.5 or 10.7% w/w), wherein % w/w relate to the weight of the immediate release coating.

Preferably the pharmaceutical composition according to this embodiment additionally comprises one or more optional color and/or final coatings.

According to an even more preferred embodiment of the present invention there is provided a pharmaceutical composition comprising or consisting essentially of a) an extended release core comprising or consisting essentially of metformin (particularly metformin hydrochloride) and one or more excipients;

b) an optional seal and/or barrier coating, preferably barrier coating;

c) an immediate release coating (API coating) comprising or consisting essentially of polyethylene glycol of molecular weight of about 6000 (e.g. 8-20% w/w, preferably 10-18 w/w, such as 14.0 or 11.9% w/w), linagliptin (as API, e.g. 1-10% w/w, preferably 2-7% w/w, such as 3.5 or 6.0% w/w), L-arginine (e.g. the weight ratio L-arginine:linagliptin may be 1:1 to 5:1, preferably 2:1 to 4:1, especially 4:1; such as e.g. 4-40% w/w, preferably 10-30% w/w, such as 14 or 24% w/w), hydroxypropyl methylcellulose (e.g. hydroxypropyl methylcellulose of 3 cP, e.g. 40-70% w/w, preferably 40-65% w/w, such as 53.2 or 45.2% w/w), polyethylene glycol of molecular weight of about 8000 (e.g. 0-5% w/w, preferably 2-4% w/w, such as 2.8 or 2.4% w/w), talc (e.g. 5-20% w/w, preferably 8-16% w/w, such as 12.5 or 10.7% w/w), wherein % w/w relate to the weight of the immediate release coating, and wherein the content of linagliptin is in the range from 1 to 10 mg, particularly 2.5 mg or 5.0 mg.

Preferably the pharmaceutical composition according to this embodiment additionally comprises one or more optional color and/or final coatings.

According to a further more preferred embodiment of the present invention there is provided a pharmaceutical composition comprising a) an extended release core comprising metformin (particularly metformin hydrochloride)

hydroxypropyl methylcellulose (e.g. viscosity about 5 mPas for a 2% solution in water at 20° C., such as Methocel E5, e.g. 2-3% w/w), polyethylene oxide (e.g. high molecular weight, e.g. about 7,000,000, such as WSR-303, e.g. 23-35% w/w), magnesium stearate (e.g. 0.5-2% w/w), wherein % w/w relate to the weight of the extended release core, and wherein the content of metformin hydrochloride is in the range from 500 to 1000 mg, for example 500, 750 or 1000 mg;

b) a barrier coating, e.g. comprising polydextrose, hydroxypropyl methylcelluloses (e.g. 3 to 50 cP, such as HPMC 2010-3, HPMC 2910-6 and HPMC 2910-50), titanium dioxide and polyethylene glycol (e.g. PEG 8000), and wherein the barrier coating has a weight for example in the range from 50 to 100 mg (such e.g. 68 mg or 85 mg);

c) an immediate release coating comprising polyethylene glycol of molecular weight of about 6000 (e.g. 8-20% w/w, preferably 10-18 w/w, such as 14.0 or 11.9% w/w), linagliptin (e.g. 1-10% w/w, preferably 2-7% w/w, such as 3.5 or 6.0% w/w), L-arginine (e.g. the weight ratio L-arginine:linagliptin may be 1:1 to 5:1, preferably 2:1 to 4:1, especially 4:1; such as e.g. 4-40% w/w, preferably 10-30% w/w, such as 14 or 24% w/w), hydroxypropyl methylcellulose (e.g. hydroxypropyl methylcellulose of 3 cP, e.g. 40-70% w/w, preferably 40-65% w/w, such as 53.2 or 45.2% w/w), polyethylene glycol of molecular weight of about 8000 (e.g. 0-5% w/w, preferably 2-4% w/w, such as 2.8 or 2.4% w/w), talc (e.g. 5-20% w/w, preferably 8-16% w/w, such as 12.5 or 10.7% w/w), wherein % w/w relate to the weight of the immediate release coating, and wherein the content of linagliptin is in the range from 1 to 10 mg, particularly 2.5 mg or 5.0 mg.

Preferably the pharmaceutical composition according to this embodiment additionally comprises one or more optional color and/or final coatings.

Film coating suspensions/solutions of API (linagliptin or Compound "A") according to this invention can be prepared by common methods, such as follows:

The film-coating agent hydroxypropyl methylcellulose (HPMC), the plasticizer polyethylene glycol (PEG) (e.g. Macrogol 400, 6000 or 8000) or, as alternative plasticizer, propylene glycol (PG) and water are dissolved and mixed by a suitable mixer (e.g. by propeller mixer) to produce the API-free coating solution. Optionally, the glidant talc suspended in water is added and the obtained suspension is homogenized. Talc may be used optionally.

The API (linagliptin or Compound "A") and—preferably in case of linagliptin—the stabilizer L-arginine are dissolved or suspended in water and added to the aqueous solution of HPMC, PEG or PG, and, optional talc, and dispersed by a suitable mixer (e.g. by propeller mixer) to provide the API coating suspension.

Alternatively, the film-coating agent hydroxypropyl methylcellulose (HPMC) and water are dissolved and mixed by a suitable mixer (e.g. by Ultraturrax).

The stabilizer L-arginine (which is present in case of linagliptin, and may be absent in case of Compound "A"), the plasticizer polyethylene glycol (PEG) (e.g. Macrogol 400, 6000 or 8000) or propylene glycol (PG), optional talc, and water are dispersed, e.g. by homogenization using e.g. ultra turrax.

After degassing of the HPMC solution (or directly after manufacturing of the HPMC solution), the aqueous suspension of PEG or PG, optional L-arginine and optional talc are added to the aqueous HPMC solution and mixed/homogenized.

The API (linagliptin or Compound "A") is dissolved or suspended in water and added to the aqueous solution of HPMC, PEG or PG, optional L-arginine and optional talc to provide the API coating suspension.

The film-coating operation is carried out in a conventional film coater. The film coating suspension and/or API (linagliptin or Compound "A") coating suspension/solution are coated at (optionally seal and/or barrier coated) metformin XR cores via coating process.

Preliminary preheating of the cores may be necessary, due to need of equilibrium of water amount of the cores.

The spray rate and air flow through the coating pan is adjusted to produce a uniform coating and coverage of the entire width of the tablet bed. The amount of the coating suspension applied can be controlled by percent weight gain of tablet cores and typically ranges from about 4 to about 12.5%.

In one aspect, this range results in linagliptin drug assay close to the desired 2.5 mg or 5 mg with a standard deviation of about 2-4% for content uniformity assay of linagliptin. The duration of the coating step is about 4-10 hours. The duration of the coating step depends on batch size, process parameters like spray rate and solid concentrations of the coating suspension.

In another aspect, this range results in Compound "A" drug assay close to the desired 5 mg, 12.5 mg, 10 mg or 25 mg with a standard deviation of about 2-4% for content uniformity assay of Compound "A". The duration of the coating step is about 4-10 hours. The duration of the coating step depends on batch size, process parameters like spray rate and solid concentrations of the coating suspension.

The API coating suspension is applied to the (optionally seal and/or barrier coated) tablet cores containing the metformin XR formulation and the amount of solids deposited in the API film layer is controlled to achieve the desired API doses.

The weight of the cores and film coated tablets may be controlled by percent weight gain during the coating process. Instead of or in addition to weight gain method a PAT method, e.g. online NIR or Raman method for end point detection of assay of API may be used.

An optional seal and/or barrier coat may separate the metformin XR core from the API-containing film coat. Typically, for the preparation of film-coated tablets a coating suspension is prepared and the tablet cores may be coated with the seal coating suspension and/or with the barrier coating suspension using standard film coater.

The film coating solvent is a volatile component, which does not remain in the final product. A typical seal and/or barrier film-coat comprises a film coating agent, a plasticizer, and, optionally, a glidant, one or more pigments and/or colors.

The metformin XR core may be seal and/or barrier coated using a seal coating agent (and a plasticizer) and/or a barrier coating agent (and a plasticizer), such as with a mixture of hydroxypropylcellulose and hydroxypropyl methylcellulose, a mixture of polyvinyl alcohol (PVA) and polyethylene glycol (PEG), a mixture of hydroxypropyl methylcellulose and either polyethylene glycol (PEG) or propylene glycol (PG), or any other suitable immediate-release film-coating agent(s). A commercial film-coat is Opadry®, Opadry II® or other Opardy IR film coat, which are formulated powder blend provided by Colorcon. Optionally the seal coat may further comprise a glidant. Optionally the barrier coat may further comprise a glidant For example, a seal or barrier coat according to this invention may comprise or consist essentially of
a film-coating agent which is hydroxypropyl methylcellulose (HPMC, hypromellose such as e.g. Methocel E5, or Pharmacoat 606),
a plasticizer which is triacetin, and
a glidant which is talc, and
optionally one or more pigments and/or colors.

For example, a seal or barrier coat according to this invention may comprise or consist essentially of
one or more film-coating agents selected from hydroxypropyl methylcellulose (HPMC, hypromellose such as e.g. hypromellose 2910 with nominal viscosity of 3 cP, hypromellose 2910 with nominal viscosity of 5 cP, hypromellose 2910 with nominal viscosity of 6 cP, hypromellose 2910 with nominal viscosity of 15 cP, hypromellose 2910 with nominal viscosity of 50 cP, Methocel E5, Methocel E15, Pharmacoat 603, Pharmacoat 606, and/or Pharmacoat 615), polydextrose, or mixtures thereof,
a plasticizer selected from polyethylene glycol (such as e.g. Macrogol 400, 3000, 4000, 6000 or 8000), and
optionally one or more pigments (e.g. titanium dioxide) and/or colors.

For example, a seal or barrier coat according to this invention may comprise or consist essentially of
a mixture of one or more hydroxypropyl methylcellulose (HPMC, hypromellose 2910 with nominal viscosity of 3 cP, hypromellose 2910 with nominal viscosity of 6 cP, and hypromellose 2910 with nominal viscosity of 50 cP) and polydextrose,
a plasticizer which is polyethylene glycol 8000, and
optionally one or more pigments (e.g. titanium dioxide) and/or colors.

For particular example, a barrier coating of this invention comprises polydextrose, hydroxypropyl methylcelluloses (e.g. 3 to 50 cP, such as HPMC 2010-3, HPMC 2910-6 and HPMC 2910-50), titanium dioxide and polyethylene glycol (e.g. PEG 8000), and wherein the barrier coating may have a weight for example in the range from 50 to 100 mg (such e.g. 68 mg or 85 mg).

The final pharmaceutical compositions of the present invention are tablets. Such tablets may be further film-coated with a color and/or final film over-coat, such as with a mixture of hydroxypropylcellulose and hydroxypropyl methylcellulose containing titanium dioxide and/or other coloring agents, such as iron oxides, dyes, and lakes; a mixture of polyvinyl alcohol (PVA) and polyethylene glycol (PEG) containing titanium dioxide and/or other coloring agents, such as iron oxides, dyes, and lakes; a mixture of hydroxypropyl methylcellulose and either polyethylene glycol (PEG) or propylene glycol (PG) containing titanium dioxide and/or other coloring agents, such as iron oxides, dyes, and lakes; or any other suitable immediate-release film-coating agent(s). The coat may provide taste masking and additional stability to the final tablet. A commercial film-coat is Opadry®, Opadry II® or other Opardy IR film coat, which are formulated powder blend provided by Colorcon.

Preferably, for the preparation of film-coated tablets a coating suspension is prepared and the tablet cores are coated with the coating suspension, typically for the API-free film over-coat to a weight gain of about 2-4%, preferably about 3%, using standard film coater. The film coating solvent is a volatile component, which does not remain in the final product. A typical film-coat comprise a film coating agent, a plasticizer, and, optionally, a glidant, one or more pigments and/or colors. For example, the film coat may comprise hydroxypropylmethylcellulose (HPMC), propylene glycol or polyethylene glycol, talc and, optionally, titanium dioxide and/or iron oxide (e.g. iron oxide yellow and/or red).

In further embodiments of the film coating layers of this invention, the film-coating agent may be one or more of hydroxypropyl methylcellulose (HPMC, hypromellose such as e.g. hypromellose 2910 with nominal viscosity of 3, 5, 6, 15 and/or 50 cP, Methocel E5, Methocel E15, Pharmacoat 603, Pharmacoat 606, and/or Pharmacoat 615), polyvinyl alcohol (PVA), ethyl cellulose, hydroxypropyl cellulose, polydextrose, methacrylic and/or acrylic polymer, or mixtures thereof (e.g. a mixture of one or more HPMC and polydextrose).

In a particular embodiment of the film coating layers of this invention, the film-coating agent may be one or more hydroxypropyl methylcellulose (HPMC, hypromellose such as e.g. hypromellose 2910 with nominal viscosity of 3, 5, 6, 15 and/or 50 cP, Methocel E5, Methocel E15, Pharmacoat 603, Pharmacoat 606, and/or Pharmacoat 615).

In another particular embodiment of the film coating layers of this invention, the film-coating agent may be polyvinyl alcohol (PVA).

In another particular embodiment of the film coating layers of this invention, the film-coating agent may be a mixture of one or more hydroxypropyl methylcellulose (HPMC, hypromellose such as e.g. hypromellose 2910 with nominal viscosity of 3, 5, 6, 15 and/or 50 cP, Methocel E5, Methocel E15, Pharmacoat 603, Pharmacoat 606, and/or Pharmacoat 615) and polydextrose.

In further embodiments of the film coating layers of this invention, the plasticizer may be one or more of polyethylene glycol (such as e.g. Macrogol 400, 3000, 4000, 6000 and/or 8000), propylene glycol, diethyl phthalate, tributyl sebacate and/or triacetin, or mixtures thereof (e.g. a mixture of polyethylene glycol and triacetin).

In a particular embodiment of the film coating layers of this invention, the plasticizer may be one or more polyethylene glycol (such as e.g. Macrogol 400, 3000, 4000, 6000 and/or 8000).

In another particular embodiment of the film coating layers of this invention, the plasticizer may be triacetin.

In further embodiments of the film coating layers of this invention, the glidant may be one or more of talc, magnesium stearate and/or fumed silica, or mixtures thereof.

In a particular embodiment of the film coating layers of this invention, the glidant may be talc.

In certain embodiments of the film coating layers of this invention, the film-coating agent may be hydroxypropyl methylcellulose (HPMC, hypromellose such as e.g. hypromellose 2910 with nominal viscosity of 3, 5, 6, 15 and/or 50 cP, Methocel E5, Methocel E15, Pharmacoat 603, Pharmacoat 606, and/or Pharmacoat 615), and the plasticizer may be polyethylene glycol (such as e.g. Macrogol 400, 3000, 4000, 6000 or 8000).

In certain embodiments of the film coating layers of this invention, the film-coating agent may be hydroxypropyl methylcellulose (HPMC, hypromellose such as e.g. hypromellose 2910 with nominal viscosity of 3, 5, 6, 15 and/or 50 cP, Methocel E5, Methocel E15, Pharmacoat 603, Pharmacoat 606, and/or Pharmacoat 615), and the plasticizer may be triacetin.

In certain embodiments of the film coating layers of this invention, the film-coating agent may be a mixture of one or more hydroxypropyl methylcellulose (HPMC, hypromellose such as e.g. hypromellose 2910 with nominal viscosity of 3, 5, 6, 15 and/or 50 cP, Methocel E5, Methocel E15, Pharmacoat 603, Pharmacoat 606, and/or Pharmacoat 615) and polydextrose, and the plasticizer may be polyethylene glycol (such as e.g. Macrogol 400, 3000, 4000, 6000 or 8000).

In certain embodiments of the film coating layers of this invention, the film-coating agent may be polyvinyl alcohol (PVA), and the plasticizer may be polyethylene glycol (such as e.g. Macrogol 400, 3000, 4000, 6000 or 8000).

In certain embodiments of the film coating layers of this invention, the film-coating agent may be polyvinyl alcohol (PVA), and the plasticizer may be triacetin.

In a further embodiment of this invention, a film coat according to this invention may comprise or consist essentially of one or more film-coating agents, e.g. selected from hydroxypropyl methylcellulose (HPMC, hypromellose such as e.g. hypromellose 2910 with nominal viscosity of 3, 5, 6, 15 and/or 50 cP, Methocel E5, Methocel E15, Pharmacoat 603, Pharmacoat 606, and/or Pharmacoat 615), polyvinyl alcohol (PVA), ethyl cellulose, hydroxypropyl cellulose, polydextrose, methacrylic and/or acrylic polymer, or a mixture thereof, optionally one or more plasticizers, e.g. selected from polyethylene glycol (such as e.g. Macrogol 400, 3000, 4000, 6000 and/or 8000), propylene glycol, diethyl phthalate, tributyl sebacate and triacetin, or a mixture thereof, optionally a glidant, e.g. talc, magnesium stearate or fumed silica, and optionally one or more pigments (e.g. titanium dioxide) and/or colors (e.g. based on iron oxides).

Accordingly, the film coating layers according to this invention may comprise one or more of the following:

at least one film-coating agent, such as e.g. hydroxypropyl methylcellulose (HPMC, hypromellose such as e.g. hypromellose 2910 with nominal viscosity of 3, 5, 6, 15 or 50 cP, Methocel E5, Methocel E15, Pharmacoat 603, Pharmacoat 606, or Pharmacoat 615), polyvinyl alcohol (PVA), ethyl cellulose, hydroxypropyl cellulose, polydextrose, or a methacrylic or acrylic polymer, at least one plasticizer, such as e.g. polyethylene glycol (such as e.g. Macrogol 400, 3000, 4000, 6000 or 8000), propylene glycol, diethyl phthalate, tributyl sebacate or triacetin, at least one glidant or anti-adherent, such as e.g. talc, magnesium stearate or fumed silica, and at least one pigment, such as e.g. titanium dioxide, and/or colorant (such as e.g. based on an iron oxide).

In certain embodiments, the hydroxypropyl methylcellulose (HPMC) as film-coating agent is hypromellose having viscosity from about 3 centipoise to about 15 centipoise or up to 40-60 centipoise, measured as aqueous 2% solution at 20° C., e.g. 3, 5, 6, 15 or 50 cP, such as e.g. hypromellose 2910 with nominal viscosity of 3 cP, hypromellose 2910 with nominal viscosity of 5 cP, hypromellose 2910 with nominal viscosity of 6 cP, hypromellose 2910 with nominal viscosity of 15 cP, hypromellose 2910 with nominal viscosity of 50 cP, Methocel E5, Methocel E15, Pharmacoat 603, Pharmacoat 606, or Pharmacoat 615.

In certain embodiments, the polyethylene glycol (PEG) as plasticizer is macrogol having average molecular weight from about 400 to about 8000 daltons, e.g. 400, 1500, 3000, 4000, 6000 or 8000 D, such as e.g. Marcrogol 400, Marcrogol 6000 or Marcrogol 8000.

In certain embodiments, the coating material is commercially available under the trade name Opadry®, Opadry II® or other Opadry® film coat.

The pharmaceutical tablet compositions of the present invention may also contain one or more additional formulation ingredients selected from a wide variety of excipients known in the pharmaceutical formulation art. According to the desired properties of the pharmaceutical composition, any number of ingredients may be selected, alone or in combination, based upon their known uses in preparing tablet compositions. Such ingredients include, but are not limited to, diluents, compression aids, glidants, disintegrants, lubricants, flavors, flavor enhancers, sweeteners, and preservatives.

The term "tablet" as used herein is intended to encompass compressed pharmaceutical dosage formulations of all shapes and sizes.

The pharmaceutical compositions (or formulations) may be packaged in a variety of ways. Generally, an article for distribution includes a container that contains the pharmaceutical composition in an appropriate form. Tablets are typically packed in an appropriate primary package for easy handling, distribution and storage and for assurance of proper stability of the composition at prolonged contact with the environment during storage. Primary containers for tablets may be bottles or blister packs, optionally with desiccant.

A suitable bottle may be made from glass or polymer (preferably polypropylene (PP) or high density polyethylene (HD-PE)) and sealed with a screw cap. The screw cap may be provided with a child resistant safety closure (e.g. press-and-twist closure) for preventing or hampering access to the contents by children. If required (e.g. in regions with high humidity), by the additional use of a desiccant (such as e.g. bentonite clay, molecular sieves, or, preferably, silica gel) the shelf life of the packaged composition can be prolonged.

A suitable blister pack comprises or is formed of a top foil (which is breachable by the tablets) and a bottom part (which contains pockets for the tablets). The top foil may contain a metalic foil, particularly an aluminium or aluminium alloy foil (e.g. having a thickness of 20 μm to 45 μm, preferably 20 μm to 25 μm) that is coated with a heat-sealing polymer layer on its inner side (sealing side). The bottom part may contain a multi-layer polymer foil (such as e.g. poly(vinyl chloride) (PVC) coated with poly(vinylidene chloride) (PVDC); or a PVC foil laminated with poly(chlorotrifluoroethylene) (PCTFE)) or a multi-layer polymer-metal-polymer foil (such as e.g. a cold-formable laminated PVC/aluminium/polyamide composition).

To ensure a long storage period especially under hot and wet climate conditions an additional overwrap or pouch made of a multi-layer polymer-metal-polymer foil (e.g. a laminated polyethylen/aluminium/polyester composition) may be used for the blister packs. Supplementary desiccant (such as e.g. bentonite clay, molecular sieves, or, preferably, silica gel) in this pouch package may prolong the shelf life even more under such harsh conditions.

The article may further comprise a label or package insert, which refer to instructions customarily included in commercial packages of therapeutic products, that may contain information about the indications, usage, dosage, administration, contraindications and/or warnings concerning the use of such therapeutic products. In one embodiment, the label or package inserts indicates that the composition can be used for any of the purposes described herein.

The present invention also provides methods particularly for treating Type 2 diabetes by orally administering to a host in need of such treatment a therapeutically effective amount of one of the fixed-dose combination pharmaceutical compositions of the present invention. In one embodiment the host in need of such treatment is a human. In another embodiment the pharmaceutical composition is in the dosage form of a tablet. The pharmaceutical compositions comprising the fixed-dose combination may be administered once-daily (QD), twice-daily (BID), thrice-daily (TID), or four-times daily.

Further, illustrative effects of the compositions according to the present invention are provided as follows, for example:

Five batches of linagliptin/metformin (e.g. 2.5/1000 mg) and different ratios (w/w) of linagliptin:arginine (1:1 to 1:5) are stored open/closed at 40° C./75% r.h. over 3 months. Overall, under closed storage conditions, no significant change in linagliptin assay results in all arginine-containing batches observed. Likewise, under closed storage conditions, no significant changes in linagliptin and metformin dissolution results are observed in the arginine-containing batches. Under open storage conditions, a correlation between arginine content and linagliptin assay results can be observed; based thereon, a linagliptin/arginine ratio of 1:4 (w/w) is selected as optimum.

In an embodiment, pharmaceutical dosage forms of this invention (preferably containing metformin XR and linagliptin as API) preferably have dissolution properties such that, for example, after 2 hours 31-54% by weight of the metformin HCl active ingredient is dissolved, and/or after 4 hours 51-74% by weight of the metformin HCl active ingredient is dissolved, and/or after 12 hours not less than 80% by weight of the metformin HCl active ingredient is dissolved.

In a further embodiment, pharmaceutical dosage forms of this invention (preferably containing metformin XR and linagliptin as API) preferably have dissolution properties such that after 45 minutes at least 75%, or at least 80%, or at least 90% by weight of linagliptin is dissolved. In a particular embodiment, after 30 minutes for linagliptin at least 70-80 (preferably not less than 75%) by weight of linagliptin is dissolved.

The dissolution properties can be determined in standard dissolution tests, e.g. according to standard pharmacopeias (such as e.g. using paddle/basket method with agitation speed of 50 rpm or 100 rpm, pH1.0 (HCl/SGF), and HPLC (linagliptin) and UV (metformin) analysis of the samples).

For illustrative example, in a certain embodiment, at pH 1 (HCl/SGF) the dissolution profiles of a linagliptin+metformin XR FDC of this invention (such as e.g. FDC 2.5/750 mg, FDC 5/1000 mg, FDC 2.5/1000 mg) and the respective reference innovator products (Trajenta® and Glumetza®) are preferably similar (f2≥50) or in the same range, using e.g. the innovator dissolution method (metformin: 100 rpm basket, linagliptin: 50 rpm basket; pH 1).

Manufacture and Polymorph

The term "linagliptin" as employed herein refers to linagliptin, a pharmaceutically acceptable salt thereof, a hydrate or solvate thereof, or a polymorphic form thereof. Crystalline forms are described in WO 2007/128721. Preferred crystalline forms are the polymorphs A and B described therein. In particular, linagliptin is the free base 1-[(4-methyl-quinazolin-2-yl)methyl]-3-methyl-7-(2-butyn-1-yl)-8-(3-(R)-amino-piperidin-1-yl)-xanthine. As linagliptin or a pharmaceutically acceptable salt thereof, linagliptin is preferred. Methods for the manufacture of linagliptin are described in the patent applications WO 2004/018468 and WO 2006/048427 for example. A therapeutic dose of linagliptin may be 5 mg per patient per day.

1-[(4-Methyl-quinazolin-2-yl)methyl]-3-methyl-7-(2-butyn-1-yl)-8-(3-(R)-amino-piperidin-1-yl)-xanthine (linagliptin)

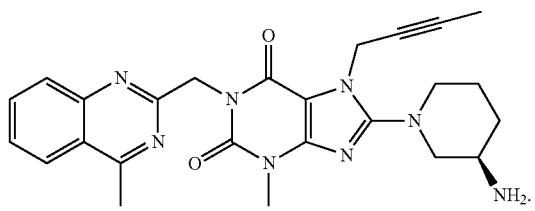 [SMILES: CC#CCn1c(N2CCC[C@@H](N)C2)nc2c1c(=O)n(Cc1nc(C)c3ccccc3n1)c(=O)n2C]

According to this invention, it is to be understood that the definition of the SGLT2 inhibitor, in particular 1-chloro-4-(β-D-glucopyranos-1-yl)-2-[4-((S)-tetrahydrofuran-3-yloxy)-benzyl]-benzene (Compound "A"), also comprises its hydrates, solvates and polymorphic forms thereof, and prodrugs thereof. With regard to the preferred 1-chloro-4-(β-D-glucopyranos-1-yl)-2-[4-((S)-tetrahydrofuran-3-yloxy)-benzyl]-benzene an advantageous crystalline form is described in the international patent application WO 2006/117359 which hereby is incorporated herein in its entirety. This crystalline form possesses good solubility properties which enable a good bioavailability of the SGLT2 inhibitor. Furthermore, the crystalline form is physico-chemically stable and thus provides a good shelf-life stability of the pharmaceutical composition.

1-Chloro-4-(β-D-glucopyranos-1-yl)-2-[4-((S)-tetra-hydrofuran-3-yloxy)-benzyl]-benzene (Compound "A")

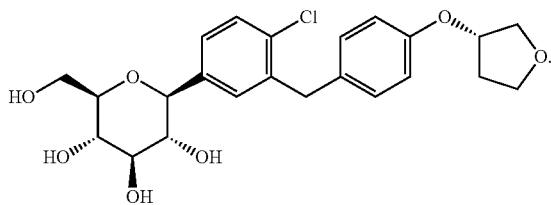 [SMILES: OC[C@H]1O[C@@H](c2ccc(Cl)c(Cc3ccc(O[C@H]4CCOC4)cc3)c2)[C@H](O)[C@@H](O)[C@@H]1O]

Methods for the manufacture of SGLT2 inhibitors according to this invention and of prodrugs thereof are known to the one skilled in the art. Advantageously, the compounds according to this invention can be prepared using synthetic methods as described in the literature, including patent applications as cited hereinbefore. Preferred methods of manufacture, in particular of 1-chloro-4-(β-D-glucopyranos-1-yl)-2-[4-((S)-tetrahydrofuran-3-yloxy)-benzyl]-benzene, are described in the WO 2006/120208.

For avoidance of any doubt, the disclosure of each of the foregoing documents cited above in connection with the specified SGLT2 or DPP-4 inhibitors is specifically incorporated herein by reference in its entirety.

Indications

As described herein by the administration of the pharmaceutical composition according to this invention, therapeutic effects can be achieved, which make it useful for treating and/or preventing certain diseases, disorders or conditions, such as e.g. those described herein.

Therefore, a treatment or prophylaxis according to this invention is advantageously suitable in those patients in need of such treatment or prophylaxis who are diagnosed of one or more of the conditions selected from the group consisting of overweight and obesity, in particular class I obesity, class II obesity, class III obesity, visceral obesity and abdominal obesity. In addition a treatment or prophylaxis according to this invention is advantageously suitable in those patients in which a weight increase is contraindicated. The pharmaceutical composition as well as the methods according to the present invention allow a reduction of the HbA1c value to a desired target range, for example <7% and preferably <6.5%, for a higher number of patients and for a longer time of therapeutic treatment compared with a corresponding monotherapy.

The pharmaceutical composition according to this invention and in particular the active ingredients therein exhibits a very good efficacy with regard to glycemic control, in particular in view of a reduction of fasting plasma glucose, postprandial plasma glucose and/or glycosylated hemoglobin (HbA1c). By administering a pharmaceutical composition according to this invention, a reduction of HbA1c equal to or greater than preferably 0.5%, even more preferably equal to or greater than 1.0% can be achieved and the reduction is particularly in the range from 1.0% to 2.0%.

Furthermore, the method and/or use according to this invention is advantageously applicable in those patients who show one, two or more of the following conditions:
(a) a fasting blood glucose or serum glucose concentration greater than 110 mg/dL, in particular greater than 125 mg/dL;
(b) a postprandial plasma glucose equal to or greater than 140 mg/dL;
(c) an HbA1c value equal to or greater than 6.5%, in particular equal to or greater than 7.0%, especially equal to or greater than 7.5%, even more particularly equal to or greater than 8.0%.

The present invention also discloses the use of the pharmaceutical composition for improving glycemic control in patients having type 2 diabetes or showing first signs of pre-diabetes. Thus, the invention also includes diabetes prevention. If therefore a pharmaceutical composition according to this invention is used to improve the glycemic control as soon as one of the above-mentioned signs of pre-diabetes is present, the onset of manifest type 2 diabetes mellitus can be delayed or prevented.

Furthermore, the pharmaceutical composition according to this invention is particularly suitable in the treatment of patients with insulin dependency, i.e. in patients who are treated or otherwise would be treated or need treatment with an insulin or a derivative of insulin or a substitute of insulin or a formulation comprising an insulin or a derivative or substitute thereof. These patients include patients with diabetes type 2 and patients with diabetes type 1.

Therefore, according to a preferred embodiment of the present invention, there is provided a method for improving glycemic control and/or for reducing of fasting plasma glucose, of postprandial plasma glucose and/or of glycosylated hemoglobin HbA1c in a patient in need thereof who is diagnosed with impaired glucose tolerance (IGT), impaired fasting blood glucose (IFG) with insulin resistance, with metabolic syndrome and/or with type 2 or type 1 diabetes mellitus characterized in that a pharmaceutical composition as defined hereinbefore and hereinafter is administered to the patient.

According to another preferred embodiment of the present invention, there is provided a method for improving glycemic control in patients, in particular in adult patients, with type 2 diabetes mellitus as an adjunct to diet and exercise.

Therefore, the method and/or use according to this invention is advantageously applicable in those patients who show one, two or more of the following conditions:
(a) insufficient glycemic control with diet and exercise alone;
(b) insufficient glycemic control despite oral monotherapy with metformin, in particular despite oral monotherapy at a maximal tolerated dose of metformin;
(c) insufficient glycemic control despite oral monotherapy with another antidiabetic agent, in particular despite oral monotherapy at a maximal tolerated dose of the other antidiabetic agent.

The lowering of the blood glucose level by the administration of a pharmaceutical composition according to this invention is insulin-independent. Therefore, a pharmaceutical composition according to this invention is particularly suitable in the treatment of patients who are diagnosed having one or more of the following conditions
  insulin resistance,
  hyperinsulinemia,
  pre-diabetes,
  type 2 diabetes mellitus, particular having a late stage type 2 diabetes mellitus,
  type 1 diabetes mellitus.

Furthermore, a pharmaceutical composition according to this invention is particularly suitable in the treatment of patients who are diagnosed having one or more of the following conditions
(a) obesity (including class I, II and/or III obesity), visceral obesity and/or abdominal obesity,
(b) triglyceride blood level ≥150 mg/dL, (c) HDL-cholesterol blood level <40 mg/dL in female patients and <50 mg/dL in male patients,
(d) a systolic blood pressure ≥130 mm Hg and a diastolic blood pressure ≥85 mm Hg,
(e) a fasting blood glucose level ≥110 mg/dL.

It is assumed that patients diagnosed with impaired glucose tolerance (IGT), impaired fasting blood glucose (IFG), with insulin resistance and/or with metabolic syndrome suffer from an increased risk of developing a cardiovascular disease, such as for example myocardial infarction, coronary heart disease, heart insufficiency, thromboembolic events. A glycemic control according to this invention may result in a reduction of the cardiovascular risks.

A pharmaceutical composition according to this invention exhibits a good safety profile. Therefore, a treatment or prophylaxis according to this invention is advantageously possible in those patients for which the mono-therapy with another antidiabetic drug is contraindicated and/or who have an intolerance against such drugs at therapeutic doses. In particular, a treatment or prophylaxis according to this invention may be advantageously possible in those patients showing or having an increased risk for one or more of the following disorders: renal insufficiency or diseases, cardiac diseases, cardiac failure, hepatic diseases, pulmonal diseases, catabolytic states and/or danger of lactate acidosis, or female patients being pregnant or during lactation.

Furthermore, it can be found that the administration of a pharmaceutical composition according to this invention results in no risk or in a low risk of hypoglycemia. Therefore, a treatment or prophylaxis according to this invention is also advantageously possible in those patients showing or having an increased risk for hypoglycemia.

A pharmaceutical composition according to this invention is particularly suitable in the long term treatment or prophylaxis of the diseases and/or conditions as described hereinbefore and hereinafter, in particular in the long term glycemic control in patients with type 2 diabetes mellitus.

The term "long term" as used hereinbefore and hereinafter indicates a treatment of or administration in a patient within a period of time longer than 12 weeks, preferably longer than 25 weeks, even more preferably longer than 1 year.

Therefore, a particularly preferred embodiment of the present invention provides a method for therapy, preferably oral therapy, for improvement, especially long term improvement, of glycemic control in patients with type 2 diabetes mellitus, especially in patients with late stage type 2 diabetes mellitus, in particular in patients additionally diagnosed of overweight, obesity (including class I, class II and/or class III obesity), visceral obesity and/or abdominal obesity.

According to another aspect of the invention, there is provided a method for preventing, slowing the progression of, delaying or treating of a condition or disorder selected from the group consisting of complications of diabetes mellitus such as cataracts and micro- and macrovascular diseases, such as dyslipidemia, nephropathy, retinopathy, neuropathy, tissue ischaemia, diabetic foot, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis, in a patient in need thereof characterized in that a pharmaceutical composition according to the invention is administered to the patient. In particular one or more aspects of diabetic nephropathy such as hyperperfusion, proteinuria and albuminuria may be treated, their progression slowed or their onset delayed or prevented. The term "tissue ischaemia" particularly comprises diabetic macroangiopathy, diabetic microangiopathy, impaired wound healing and diabetic ulcer. The terms "micro- and macrovascular diseases" and "micro- and macrovascular complications" are used interchangeably in this application.

According to another aspect of the invention, there is provided a method for preventing, slowing the progression of, delaying or treating a metabolic disorder selected from the group consisting of type 2 diabetes mellitus, impaired glucose tolerance (IGT), impaired fasting blood glucose (IFG), hyperglycemia, postprandial hyperglycemia, overweight, obesity, metabolic syndrome, gestational diabetes and diabetes related to cystic fibrosis in a patient in need thereof characterized in that a pharmaceutical composition according to the invention is administered to the patient.

According to another aspect of the invention, there is provided a method for improving glycemic control and/or for reducing of fasting plasma glucose, of postprandial plasma glucose and/or of glycosylated hemoglobin HbA1c in a patient in need thereof characterized in that a pharmaceutical composition according to the invention is administered to the patient.

The pharmaceutical composition according to this invention may also have valuable disease-modifying properties with respect to diseases or conditions related to impaired glucose tolerance (IGT), impaired fasting blood glucose (IFG), insulin resistance and/or metabolic syndrome.

According to another aspect of the invention, there is provided a method for preventing, slowing, delaying or reversing progression from impaired glucose tolerance (IGT), impaired fasting blood glucose (IFG), insulin resistance and/or from metabolic syndrome to type 2 diabetes mellitus in a patient in need thereof characterized in that a pharmaceutical composition according to the invention is administered to the patient.

As by the use of a pharmaceutical composition according to this invention, an improvement of the glycemic control in patients in need thereof is obtainable, also those conditions and/or diseases related to or caused by an increased blood glucose level may be treated.

By the administration of a pharmaceutical composition according to this invention excessive blood glucose levels are not converted to insoluble storage forms, like fat, but excreted through the urine of the patient. It can be seen that loss of fat may account for the majority of the observed weight loss whereas no significant changes in body water or protein content are observed. Therefore, no gain in weight or even a reduction in body weight is the result.

According to another aspect of the invention, there is provided a method for reducing body weight and/or body fat or preventing an increase in body weight and/or body fat or facilitating a reduction in body weight and/or body fat in a patient in need thereof characterized in that a pharmaceutical composition according to the invention is administered to the patient.

By the administration of a combination or pharmaceutical composition according to the present invention, an abnormal accumulation of ectopic fat, in particular of the liver, may be reduced or inhibited. Therefore, according to another aspect of the present invention, there is provided a method for preventing, slowing, delaying or treating diseases or conditions attributed to an abnormal accumulation of ectopic fat, in particular of the liver, in a patient in need thereof characterized in that a pharmaceutical composition according to the invention is administered to the patient. Diseases or conditions which are attributed to an abnormal accumulation of liver fat are particularly selected from the group consisting of general fatty liver, non-alcoholic fatty liver (NAFL), non-alcoholic steatohepatitis (NASH), hyperalimen-tation-induced fatty liver, diabetic fatty liver, alcoholic-induced fatty liver or toxic fatty liver.

Another aspect of the invention provides a method for maintaining and/or improving the insulin sensitivity and/or for treating or preventing hyperinsulinemia and/or insulin resistance in a patient in need thereof characterized in that a pharmaceutical composition according to the invention is administered to the patient.

According to another aspect of the invention, there is provided a method for preventing, slowing progression of, delaying, or treating new onset diabetes after transplantation (NODAT) and/or post-transplant metabolic syndrome (PTMS) in a patient in need thereof characterized in that a pharmaceutical composition according to the invention is administered to the patient.

According to a further aspect of the invention, there is provided a method for preventing, delaying, or reducing NODAT and/or PTMS associated complications including micro- and macrovascular diseases and events, graft rejection, infection, and death in a patient in need thereof characterized in that a pharmaceutical composition according to the invention is administered to the patient.

The pharmaceutical composition according to the invention is capable of facilitating the lowering of serum total urate levels in the patient. Therefore according to another aspect of the invention, there is provided a method for treating hyperuricemia and hyperuricemia-associated conditions, such as for example gout, hypertension and renal failure, in a patient in need thereof characterized in that a pharmaceutical composition according to the invention is administered to the patient.

The administration of a pharmaceutical composition increases the urine excretion of glucose. This increase in osmotic excretion and water release and the lowering of urate levels are beneficial as a treatment or prevention for kidney stones. Therefore in a further aspect of the invention, there is provided a method for treating or preventing kidney stones in a patient in need thereof characterized in that a pharmaceutical composition according to the invention is administered to the patient.

The invention also relates to a pharmaceutical composition according to this invention for use in a method as described hereinbefore and hereinafter.

The invention also relates to a use of a pharmaceutical composition according to this invention for the manufacture of a medicament for use in a method as described hereinbefore and hereinafter.

Definitions

The term "active ingredient" of a pharmaceutical composition according to the present invention means the SGLT2 inhibitor, the DPP-4 inhibitor and/or metformin according to the present invention.

The term "body mass index" or "BMI" of a human patient is defined as the weight in kilograms divided by the square of the height in meters, such that BMI has units of $kg/m^2$.

The term "overweight" is defined as the condition wherein the individual has a BMI greater than or 25 $kg/m^2$ and less than 30 $kg/m^2$. The terms "overweight" and "pre-obese" are used interchangeably.

The term "obesity" is defined as the condition wherein the individual has a BMI equal to or greater than 30 $kg/m^2$. According to a WHO definition the term obesity may be categorized as follows: the term "class|obesity" is the condition wherein the BMI is equal to or greater than 30 $kg/m^2$ but lower than 35 $kg/m^2$; the term "class II obesity" is the condition wherein the BMI is equal to or greater than 35 $kg/m^2$ but lower than 40 $kg/m^2$; the term "class III obesity" is the condition wherein the BMI is equal to or greater than 40 $kg/m^2$.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "hypoglycemia" is defined as the condition in which a subject has a blood glucose concentration below the normal range, in particular below 70 mg/dL (3.89 mmol/L) or even below 60 mg/dl.

The term "postprandial hyperglycemia" is defined as the condition in which a subject has a 2 hour postprandial blood glucose or serum glucose concentration greater than 200 mg/dL (11.1 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.8 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.8 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio<1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28:412-19), of the ratio of intact proinsulin to insulin (Forst et al., *Diabetes* 2003, 52(Suppl. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

$$\text{HOMA-IR} = [\text{fasting serum insulin}(\mu U/mL)] \times [\text{fasting plasma glucose}(mmol/L)/22.5]$$

As a rule, other parameters are used in everyday clinical practice to assess insulin resistance. Preferably, the patient's triglyceride concentration is used, for example, as increased triglyceride levels correlate significantly with the presence of insulin resistance.

Patients with a predisposition for the development of IGT or IFG or type 2 diabetes are those having euglycemia with hyperinsulinemia and are by definition, insulin resistant. A typical patient with insulin resistance is usually overweight or obese, but this is not always the case. If insulin resistance can be detected, this is a particularly strong indication of the presence of pre-diabetes. Thus, it may be that in order to maintain glucose homoeostasis a person have e.g. 2-3 times as high endogenous insulin production as a healthy person, without this resulting in any clinical symptoms.

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28:412-19), the ratio of intact proinsulin to insulin (Forst et al., *Diabetes* 2003, 52(Suppl. 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "pre-diabetes" is the condition wherein an individual is pre-disposed to the development of type 2 diabetes. Pre-diabetes extends the definition of impaired glucose tolerance to include individuals with a fasting blood glucose within the high normal range ≥100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or IFG or type 2 diabetes. Insulin resistance can be confirmed in these individuals by calculating the HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

The term "type 1 diabetes" is defined as the condition in which a subject has, in the presence of autoimmunity towards the pancreatic beta-cell or insulin, a fasting blood glucose or serum glucose concentration greater than 125 mg/dL (6.94 mmol/L). If a glucose tolerance test is carried out, the blood sugar level of a diabetic will be in excess of 200 mg of glucose per dL (11.1 mmol/l) of plasma 2 hours after 75 g of glucose have been taken on an empty stomach, in the presence of autoimmunity towards the pancreatic beta cell or insulin. In a glucose tolerance test 75 g of glucose are administered orally to the patient being tested after 10-12 hours of fasting and the blood sugar level is recorded immediately before taking the glucose and 1 and 2 hours after taking it. The presence of autoimmunity towards the pancreatic beta-cell may be observed by detection of circulating islet cell autoantibodies ["type 1A diabetes mellitus"], i.e., at least one of: GAD65 [glutamic acid decarboxylase-65], ICA [islet-cell cytoplasm], IA-2 [intracytoplasmatic domain of the tyrosine phosphatase-like protein IA-2], ZnT8 [zinc-transporter-8] or anti-insulin; or other signs of autoimmunity without the presence of typical circulating autoantibodies [type 1B diabetes], i.e. as detected through pancreatic biopsy or imaging). Typically a genetic predisposition is present (e.g. HLA, INS VNTR and PTPN22), but this is not always the case.

The term "type 2 diabetes" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference ≥85 cm in men and ≥90 cm in women;
2. Triglycerides: ≥150 mg/dL
3. HDL-cholesterol <40 mg/dL in men
4. Blood pressure ≥130/85 mm Hg (SBP ≥130 or DBP ≥85)
5. Fasting blood glucose ≥100 mg/dL The NCEP definitions have been validated (Laaksonen D E, et al. *Am J. Epidemiol.* (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The definitions of NODAT (new onset diabetes after transplantation) and PTMS (post-transplant metabolic syndrome) follow closely that of the American Diabetes Association diagnostic criteria for type 2 diabetes, and that of the International Diabetes Federation (IDF) and the American Heart Association/National Heart, Lung, and Blood Institute, for the metabolic syndrome. NODAT and/or PTMS are associated with an increased risk of micro- and macrovascular disease and events, graft rejection, infection, and death. A number of predictors have been identified as potential risk factors related to NODAT and/or PTMS including a higher age at transplant, male gender, the pre-transplant body mass index, pre-transplant diabetes, and immunosuppression.

The term "gestational diabetes" (diabetes of pregnancy) denotes a form of the diabetes which develops during pregnancy and usually ceases again immediately after the birth. Gestational diabetes is diagnosed by a screening test which is carried out between the 24th and 28th weeks of pregnancy. It is usually a simple test in which the blood sugar level is measured one hour after the administration of 50 g of glucose solution. If this 1 h level is above 140 mg/dl, gestational diabetes is suspected. Final confirmation may be obtained by a standard glucose tolerance test, for example with 75 g of glucose.

The term "hyperuricemia" denotes a condition of high serum total urate levels. In human blood, uric acid concentrations between 3.6 mg/dL (ca. 214 μmol/L) and 8.3 mg/dL (ca. 494 μmol/L) are considered normal by the American Medical Association. High serum total urate levels, or hyperuricemia, are often associated with several maladies. For example, high serum total urate levels can lead to a type of arthritis in the joints kown as gout. Gout is a condition created by a build up of monosodium urate or uric acid crystals on the articular cartilage of joints, tendons and surrounding tissues due to elevated concentrations of total urate levels in the blood stream. The build up of urate or uric acid on these tissues provokes an inflammatory reaction of these tissues. Saturation levels of uric acid in urine may result in kidney stone formation when the uric acid or urate crystallizes in the kidney. Additionally, high serum total urate levels are often associated with the so-called metabolic syndrome, including cardiovascular disease and hypertension.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

The terms "prophylactically treating", "preventivally treating" and "preventing" are used interchangeably and comprise a treatment of patients at risk to develop a condition mentioned hereinbefore, thus reducing said risk.

Other or further features and advantages of the present invention will become apparent from the following examples. The following examples serve to illustrate, by way of example, the principles of the invention without restricting it.

The following examples (as well as the features or aspects included therein) relate to particularly interesting embodiments or aspects of the present invention.

EXAMPLES

Linagliptin/Metformin HCl extended-release fixed-dose-combination tablets are film-coated tablets manufactured using typical processes and equipment for wet-granulation, tableting and film-coating. The core tablet contains metformin HCl for extended-release and may be based on an expandable polymeric swelling formulation that increases gastric retention and extends drug release from the matrix. This metformin HCl core tablet may be film-coated (spray-coated) with up to four layers (e.g. barrier coat layer, immediate-release active coat layer, color coat layer, final coat layer), one of which (active coat layer) contains the active pharmaceutical ingredient linagliptin to add the immediate-release active component.

Tablet Coating—Barrier Coat

Purified water is charged into a stainless steel mixing vessel equipped with a suitable mixer. While mixing at a speed that ensures vortex formation, the Film Forming System is added and mixed for at least 20 minutes. Mixing of the coating solution is continued throughout the coating operation. An appropriate quantity of metformin HCl extended release cores are charged to the coating pan of the perforated coating system equipped with a peristaltic pump and two spray nozzles. After the cores are preheated, pan rotation and spraying of the coating suspension begin. A fixed amount of the barrier coating suspension, which incorporates approximately 15% excess to account for losses during spraying, is applied to the cores. For example, the cores are coated to obtain a weight gain of 6%; to account for losses during spraying, an amount of coating solution equivalent to approximately 6.9% weight gain is used for spraying. Upon completion of the application of the coating solution, the cores are dried (target pan speed 3 rpm, target inlet air temperature 55° C.) for 15 minutes. The barrier-coated cores are then allowed to cool (product temperature not more than 35° C.).

Tablet Coating—Linagliptin Active Coat

Purified water is charged into a stainless steel mixing vessel equipped with a suitable mixer. While mixing at a speed that ensures vortex formation, each component polyethylene glycol (PEG 6000), L-arginine, linagliptin, talc and the Film Forming System (HPMC 2910-3 and PEG 8000) is added. The coating suspension is mixed for at least 20 minutes or until the last component added is homogenized. An appropriate quantity of barrier-coated tablet cores are charged to the coating pan of the perforated coating system equipped with a peristaltic pump and two spray nozzles. After the cores are preheated, pan rotation and spraying of the coating suspension begin. A fixed amount of the active coating suspension, which incorporates approximately 10% excess to account for losses during spraying, is applied. For example, the cores are coated to obtain a weight gain of 4.7%; to account for losses during spraying, an amount of coating solution equivalent to approximately 5.4% weight gain is used for spraying. Upon completion of the application of the coating solution, the cores are dried (target pan speed 3 rpm, target inlet air temperature 55° C.) for 15 minutes. The active-coated cores are then allowed to cool (product temperature not more than 35° C.).

The following compositions can be obtained.

TABLE A

Linagliptin/Metformin HCl extended release formulation, FDC 2.5 mg/750 mg

| Component | mg/tablet |
|---|---|
| Extended release core | |
| Metformin hydrochloride (Metformin HCl) | 750 |
| Polyethylene Oxide | 355.2 |
| (e.g. high molecular weight such as about 7,000,000, such as WSR-303) | |
| Hydroxypropyl methylcellulose (Hypromellose) | 25.5 |
| (e.g. viscosity about 5 mPas for a 2% solution in water at 20° C., such as HPMC 2910-5 (Methocel E5)) | |
| Magnesium Stearate | 11.3 |

TABLE A-continued

Linagliptin/Metformin HCl extended release formulation, FDC 2.5 mg/750 mg

| Component | mg/tablet |
|---|---|
| Barrier coat: | |
| Film Forming System: | 68.2 |
| Hydroxypropyl methylcellulose (e.g. HPMCs of 3 cP, 6 cP and 50 cP, such as | |
| HPMC 2910-3 (e.g. 19.46% w/w), | |
| HPMC 2910-6 (e.g. 16.68% w/w) and | |
| HPMC 2910-50 (e.g. 2.79% w/w)), | |
| Polydextrose (e.g. 25.94% w/w), | |
| Polyethylene glycol (e.g. PEG 8000, e.g. 2.70% w/w), | |
| Titanium dioxide (e.g. 32.43% w/w), | |
| Purified water | —* |
| Active (API) coat: | |
| Linagliptin (as API) | 2.5 |
| Film Forming System: | 40.0 |
| Hydroxypropyl methylcellulose (e.g. HPMC of 3 cP, such as HPMC 2910-3, e.g. 95% w/w) | |
| Polyethylene glycol (e.g. PEG 8000, e.g. 5% w/w) | |
| L-Arginine | 10.0 |
| Polyethylene glycol (e.g. PEG 6000) | 10.0 |
| Talc | 9.0 |
| Purified water | —* |

*Processing agent water used in manufacturing and removed by drying

TABLE B

Linagliptin/Metformin HCl extended release formulation, FDC 2.5 mg/1000 mg

| Component | mg/tablet |
|---|---|
| Extended release core | |
| Metformin hydrochloride (Metformin HCl) | 1000 |
| Polyethylene Oxide | 370 |
| (e.g. high molecular weight such as about 7,000,000, such as WSR-303) | |
| Hydroxypropyl methylcellulose (Hypromellose) | 34.0 |
| (e.g. viscosity about 5 mPas for a 2% solution in water at 20° C., such as HPMC 2910-5 (Methocel E5)) | |
| Magnesium Stearate | 15.0 |
| Barrier coat: | |
| Film Forming System: | 85.0 |
| Hydroxypropyl methylcellulose (e.g. HPMCs of 3 cP, 6 cP and 50 cP, such as | |
| HPMC 2910-3 (e.g. 19.46% w/w), | |
| HPMC 2910-6 (e.g. 16.68% w/w) and | |
| HPMC 2910-50 (e.g. 2.79% w/w)), | |
| Polydextrose (e.g. 25.94% w/w), | |
| Polyethylene glycol (e.g. PEG 8000, e.g. 2.70% w/w), | |
| Titanium dioxide (e.g. 32.43% w/w), | |
| Purified water | —* |
| Active (API) coat: | |
| Linagliptin (as API) | 2.5 |
| Film Forming System: | 40.0 |
| Hydroxypropyl methylcellulose (e.g. HPMC of 3 cP, such as HPMC 2910-3, e.g. 95% w/w) | |
| Polyethylene glycol (e.g. PEG 8000, e.g. 5% w/w) | |
| L-Arginine | 10.0 |
| Polyethylene glycol (e.g. PEG 6000) | 10.0 |
| Talc | 9.0 |
| Purified water | —* |

*Processing agent water used in manufacturing and removed by drying

TABLE C

Linagliptin/Metformin HCl extended release formulation, FDC 5 mg/1000 mg

| Component | mg/tablet |
|---|---|
| Extended release core | |
| Metformin hydrochloride (Metformin HCl) | 1000 |
| Polyethylene Oxide | 370 |
| (e.g. high molecular weight such as about 7,000,000, such as WSR-303) | |
| Hydroxypropyl methylcellulose (Hypromellose) | 34.0 |
| (e.g. viscosity about 5 mPas for a 2% solution in water at 20° C., such as HPMC 2910-5 (Methocel E5)) | |
| Magnesium Stearate | 15.0 |
| Barrier coat: | |
| Film Forming System: | 85.0 |
| Hydroxypropyl methylcellulose (e.g. HPMCs of 3 cP, 6 cP and 50 cP, such as | |
| HPMC 2910-3 (e.g. 19.46% w/w), | |
| HPMC 2910-6 (e.g. 16.68% w/w) and | |
| HPMC 2910-50 (e.g. 2.79% w/w)), | |
| Polydextrose (e.g. 25.94% w/w), | |
| Polyethylene glycol (e.g. PEG 8000, e.g. 2.70% w/w), | |
| Titanium dioxide (e.g. 32.43% w/w), | |
| Purified water | —* |
| Active (API) coat: | |
| Linagliptin (as API) | 5.0 |
| Film Forming System: | 40.0 |
| Hydroxypropyl methylcellulose (e.g. HPMC of 3 cP, such as HPMC 2910-3, e.g. 95% w/w) | |
| Polyethylene glycol (e.g. PEG 8000, e.g. 5% w/w) | |
| L-Arginine | 20.0 |
| Polyethylene glycol (e.g. PEG 6000) | 10.0 |
| Talc | 9.0 |
| Purified water | —* |

*Processing agent water used in manufacturing and removed by drying

Optionally, the above compositions may be further coated by a color coat layer and/or a clear final coat. Typically, the color coat and the final coat may represent 1-4% w/w (preferably 1-2% w/w) of the total composition and each comprise one or more film-forming agents, one or more plasticizers, one or more optional glidants, and one or more optional pigments and/or colors. For example, a color coat may comprise hydroxypropyl methylcellulose (e.g. HPMC of 3 cP and/or HPMC of 6 cP), polyethylene glycol (e.g. PEG 8000), titanium dioxide and a color or lake. For example, a final coat may comprise hydroxypropyl methylcellulose (e.g. HPMC of 3 cP) and polyethylene glycol (e.g. PEG 8000) as well as a polishing wax (e.g. carnauba wax).

The invention claimed is:

1. A pharmaceutical composition comprising:
   a) an extended release core comprising metformin hydrochloride, poly(ethylene oxide) as a swellable and/or extended release polymer, and one or more excipients;
   b) a barrier coating comprising a mixture of hydroxypropyl cellulose and hydroxypropyl methylcellulose as film-coating agent, and
   c) an immediate release coating consisting of
      linagliptin,
      L-arginine,
      polyethylene glycol,
      hydroxypropyl methylcellulose, and
      talc.

2. The pharmaceutical composition according to claim 1, wherein the weight ratio of the L-arginine to linagliptin is within the range from about 4:1 to about 2:1.

3. The pharmaceutical composition according to claim 1, wherein the immediate release coating c) contains:
   polyethylene glycol of molecular weight of about 6000 in an amount of 8-20% w/w linagliptin in an amount of 1-10% w/w,
   L-arginine in an amount of 4-40% w/w,
   hydroxypropyl methylcellulose in an amount of 40-70% w/w,
   polyethylene glycol of molecular weight of about 8000 in an amount of 0-5% w/w, and talc in an amount of 5-20% w/w,
   wherein % w/w relate to the weight of the immediate release coating, and
   wherein the content of linagliptin is in the range from 1 to 10 mg.

4. The pharmaceutical composition according to claim 1, wherein the barrier coating is a film coat formulation further comprising:
   one or more plasticizers selected from polyethylene glycol, propylene glycol, diethyl phthalate, tributyl sebacate and/or triacetin, or a mixture thereof,
   optionally a glidant selected from talc, magnesium stearate and fumed silica, and
   optionally one or more pigments and/or colorants.

5. The pharmaceutical composition according to claim 1, wherein the barrier coating is a film coat formulation further comprising a plasticizer, and
   optionally, a glidant, one or more pigments and/or colors.

6. The pharmaceutical composition according to claim 1, wherein the metformin hydrochloride is present in an unit dosage strength of 500, 750, 850, 1000 or 1500 mg.

7. The pharmaceutical composition according to claim 1, wherein the linagliptin is present in an unit dosage strength of 0.5, 1, 2.5 or 5 mg.

8. The pharmaceutical composition according to claim 1, wherein said pharmaceutical composition is a tablet for oral administration.

9. The pharmaceutical composition according to claim 8 further comprising a color and/or final coating.

10. The pharmaceutical composition according to claim 9, wherein the color and/or final coating is each a film coat formulation independently comprising:
   one or more film-coating agents selected from hydroxypropyl methylcellulose (HPMC), polyvinyl alcohol (PVA), ethyl cellulose, hydroxypropyl cellulose, polydextrose, methacrylic and/or acrylic polymer, or a mixture thereof,
   optionally one or more plasticizers selected from polyethylene glycol, propylene glycol, diethyl phthalate, tributyl sebacate and/or triacetin, or a mixture thereof,
   optionally a glidant selected from talc, magnesium stearate and fumed silica, and
   optionally one or more pigments and/or colorants.

11. The pharmaceutical composition according to claim 9, wherein the color and/or final coating is each a film coat formulation independently comprising a film-coating agent, a plasticizer, and, optionally, a glidant, one or more pigments and/or colors.

12. A method of treating and/or preventing a metabolic disease comprising administering a pharmaceutical composition according to claim 1:
   either in type 2 diabetes patients who have not been previously treated with an antihyperglycemic agent,
   or in type 2 diabetes patients with insufficient glycemic control despite therapy with one or two conventional antihyperglycemic agents selected from the group consisting of metformin, sulphonylureas, thiazolidindiones, glinides, alpha-glucosidase blockers, GLP-1 or GLP-1 analogues, and insulin or insulin analogues.

13. The method according to claim 12, wherein linagliptin is comprised in an amount of 2.5 mg, and metformin hydrochloride is comprised in an amount of 750 mg or 1000 mg.

14. The method according to claim 13, wherein the composition is administered as two tablets once daily to the patients.

15. The method according to claim 12, wherein linagliptin is comprised in an amount of 5 mg, and metformin hydrochloride is comprised in an amount of 1000 mg.

16. The method according to claim 15, wherein the composition is administered as one tablet once daily to the patients.

17. The pharmaceutical composition according to claim 1, wherein the weight ratio of the L-arginine to linagliptin is about 4:1.

* * * * *